(12) United States Patent
Shyur et al.

(10) Patent No.: US 10,238,631 B2
(45) Date of Patent: Mar. 26, 2019

(54) SESQUITERPENE DERIVATIVES AND THEIR USE IN INFLAMMATION OR CANCER TREATMENT

(71) Applicant: Academia Sinica, Taipei (TW)

(72) Inventors: Lie-Fen Shyur, Taipei (TW); Kuo-Hsiung Lee, Chapel Hill, NC (US); Kyoko Nakagawa-Goto, Ishikawa (JP); Jia-Hua Feng, Taipei (TW); Jo-Yu Chen, New Taipei (TW); Wai-Leng Lee, Taichung (TW); Yu-Ting Cheng, Taichung (TW); Jing-Ying Huang, Taipei (TW)

(73) Assignee: Academia Sinica, Taipei (TW)

( * ) Notice: Subject to any disclaimer, the term of this patent is extended or adjusted under 35 U.S.C. 154(b) by 76 days.

(21) Appl. No.: 15/316,700

(22) PCT Filed: Jun. 5, 2015

(86) PCT No.: PCT/US2015/034589
§ 371 (c)(1),
(2) Date: Dec. 6, 2016

(87) PCT Pub. No.: WO2015/188169
PCT Pub. Date: Dec. 10, 2015

(65) Prior Publication Data
US 2017/0182001 A1    Jun. 29, 2017

Related U.S. Application Data

(60) Provisional application No. 62/009,215, filed on Jun. 7, 2014.

(51) Int. Cl.
*A61K 31/365* (2006.01)
*A61K 45/06* (2006.01)
*A61K 31/337* (2006.01)
*A61K 31/437* (2006.01)
*C07D 493/18* (2006.01)
*A61K 31/198* (2006.01)
*A61K 31/655* (2006.01)

(52) U.S. Cl.
CPC .......... *A61K 31/365* (2013.01); *A61K 31/198* (2013.01); *A61K 31/337* (2013.01); *A61K 31/437* (2013.01); *A61K 31/655* (2013.01); *A61K 45/06* (2013.01); *C07D 493/18* (2013.01)

(58) Field of Classification Search
None
See application file for complete search history.

(56) References Cited

U.S. PATENT DOCUMENTS 8,754,121 B2 * 6/2014 Shyur .................. A61K 31/365
424/623
2012/0045519 A1  2/2012 Shyur et al.

OTHER PUBLICATIONS

Marcus T. Scotti et al "Quantitative structure-activity relationship of sesquiterpene lactones with cytotoxic activity" Bioorganic & Medicinal Chemistry (2007) vol. 15, No. 8, pp. 2927-2934.
Thomas J. Schmidt et al "Quantitative Structure-Cytotoxicity Relationships of Sesquitetpene Lactones derived from partial charge (Q)-based fractional Accessible Surface Area Descriptors (Q_frASAs)" (2002) vol. 21, No. 3, pp. 276-287.
Kupchan S.M. et al "Tumor inhibitors. XL. Isolation and structural elucidation of elephantin and elephantopin, two novel sesquiterpenoid tumor inhibitors from Elephantopus elatus" (1969) J. Org. Chem. 34 (12), pp. 3867-3875.
Zou G et al "Deoxyelephantopin inhibits cancer cell proliferation and functions as a selective partial agonist against PPARgamma" (2008) Biochem Pharmacol, 75(6):1381-92.
Lee WL et al "Deoxyelephantopin impedes mammary adenocarcinoma cell motility by inhibiting calpain-mediated adhesion dynamics and inducing reactive oxygen species and aggresome formation" Free Radic Biol Med. (2012); 52(8):1423-36.
International Search Report for PCT/US2015/034589, dated Aug. 21, 2015.
Written Opinion of International Search Authority for PCT/US2015/034589, dated Aug. 21, 2015.

* cited by examiner

*Primary Examiner* — Heidi Reese
(74) *Attorney, Agent, or Firm* — Hsiu-Ming Saunders; Intellectual Property Connections, Inc.

(57) ABSTRACT

A new class of sesquiterpene derivative useful for treating cancerous and inflammatory diseases are disclosed. These deoxyelephantopin derivatives are effective in suppressing proliferation, migration, mobility, invasion, growth, and/or metastasis of cancer cells in a patient, or useful for enhancing an anti-proliferative effect of another anti-cancer drug on cancer cells when treating a patient, or for sensitizing and/or enhancing an anti-cancer effect of a gluthathione synthesis blocker on inhibition of triple negative breast cancer cell activity, or for treatment and/or prophylaxis of lipopolysaccharide-stimulated inflammatory response in a patient, or for all of the above. Also disclosed are methods of preparing the deoxyelephantopin derivatives.

20 Claims, 11 Drawing Sheets

FIG. 2B
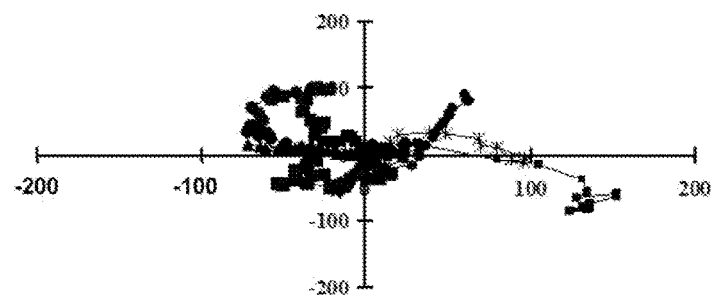
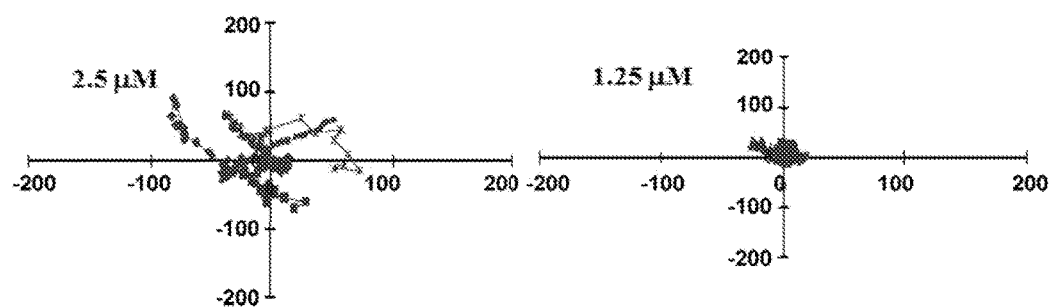
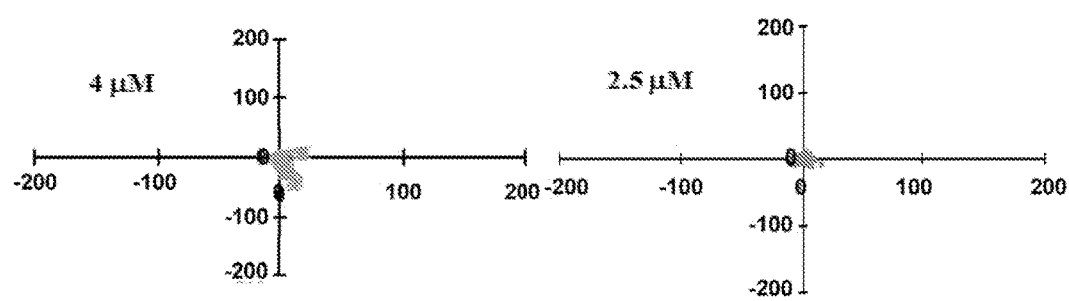
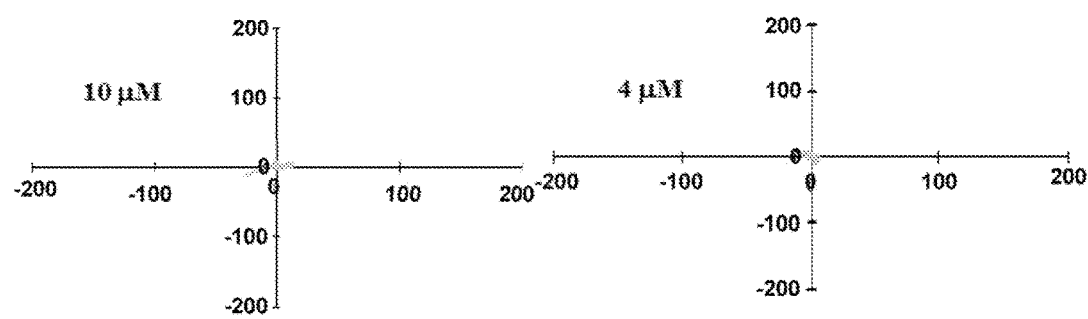

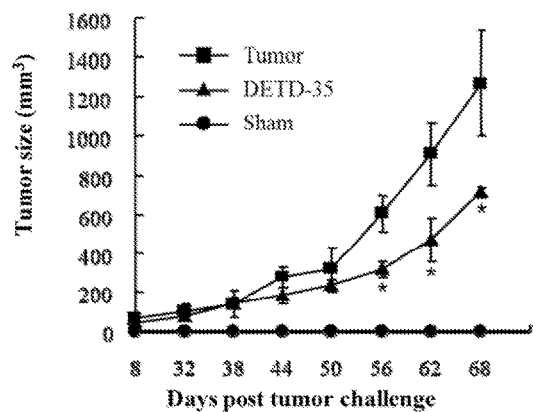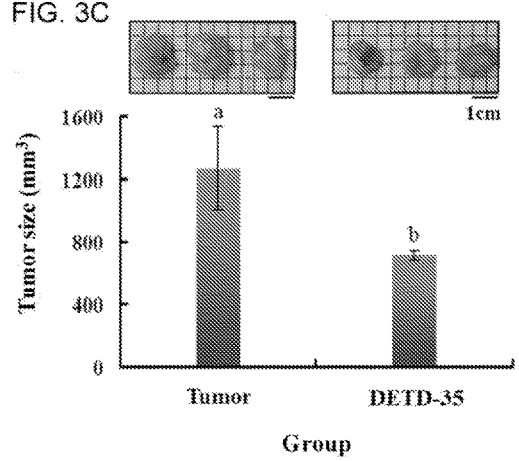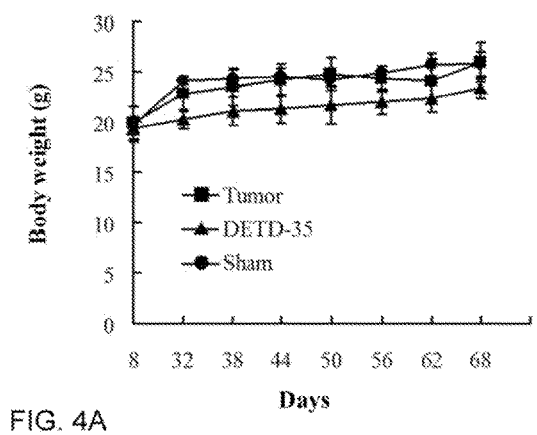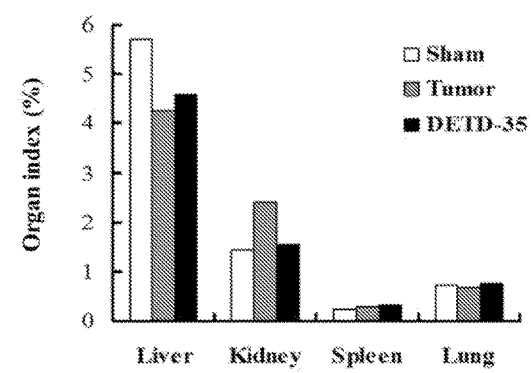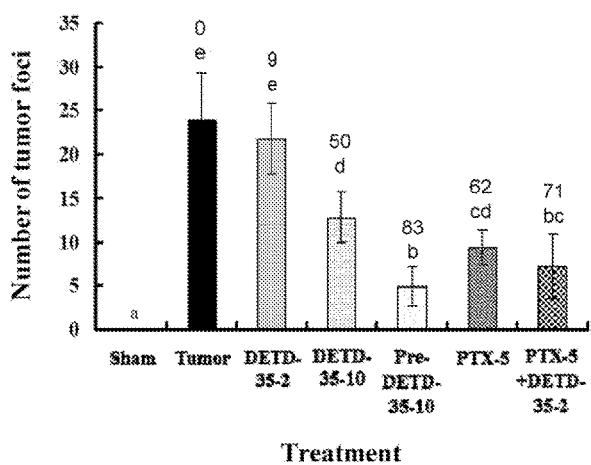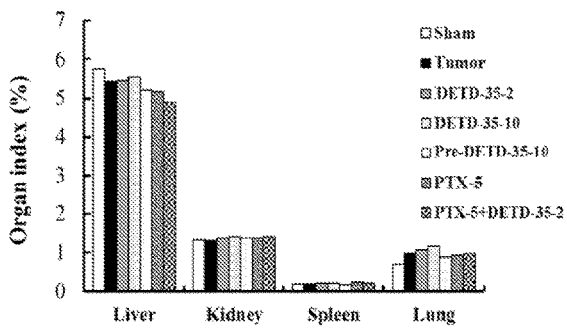

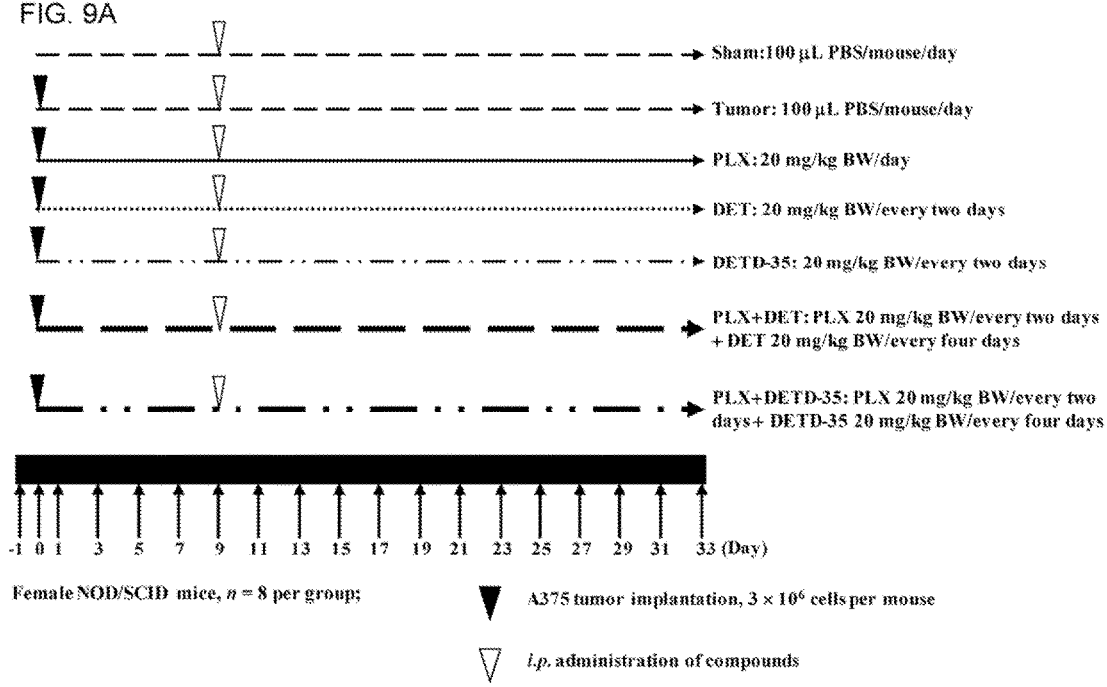
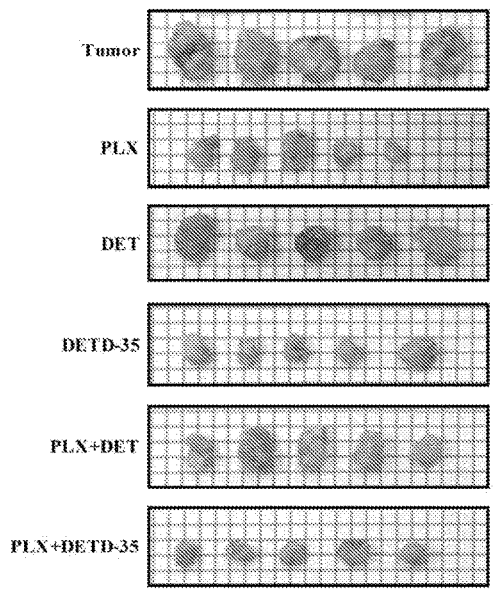
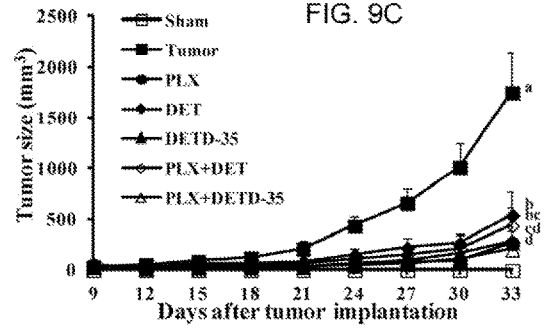
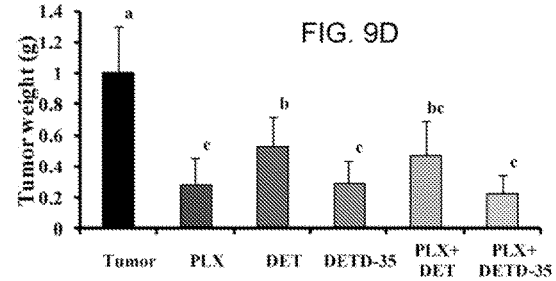

SESQUITERPENE DERIVATIVES AND THEIR USE IN INFLAMMATION OR CANCER TREATMENT

REFERENCE TO RELATED APPLICATION

This application is a national stage application (under 35 U.S.C. 371) of PCT/US2015/034589 filed on 5 Jun. 2015, which claims priority to US provisional application 62/009,215 filed on 7 Jun. 2014, all of which are herein incorporated by reference in their entireties.

FIELD OF THE INVENTION

The present invention relates generally to sesquiterpene derivatives, and more specifically to deoxyelephantopin derivatives.

BACKGROUND OF THE INVENTION

The identification and validation of the potential benefits of phytocompounds with low toxicity, but effective for cancer inhibition, has thus become an important area of pharmaceutical science. The pressing need for development of new therapeutic or preventive agents for cancer diseases has spurred the search for bioactive phytocompounds or their derived analogs with novel modes of action or improved efficacy.

U.S. Pat. No. 8,754,121 discloses use of deoxyelephantopin (DET) and analogues thereof for treatment of melanoma.

SUMMARY OF THE INVENTION

In one aspect, the invention relates to a compound of Formula (I)

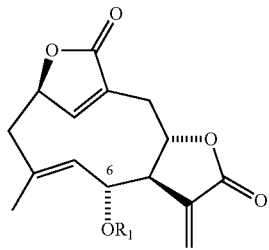

(I)

or a pharmaceutically acceptable salt thereof,
wherein $R_1$ is selected from the group consisting of hydrogen, -carbonyl($C_1$-$C_8$)alkyl($C_1$-$C_8$)alkenyl, -carbonyl($C_1$-$C_8$)alkyl($C_1$-$C_8$)alkenyl($C_1$-$C_8$)alkyl, -carbonyl($C_1$-$C_8$)alkenyl($C_6$-$C_{20}$)aryl, -carbonyl($C_1$-$C_8$)alkenyl($C_1$-$C_8$)alkoxy($C_6$-$C_{20}$)aryl, -carbonyl($C_1$-$C_8$)alkenyl, -carbonyl($C_1$-$C_8$)haloalkyl, -carbonyl($C_1$-$C_8$)alkyl, -carbonyl($C_1$-$C_8$)alkylOCO($C_1$-$C_8$)alkyl, -carbonyl($C_1$-$C_8$)alkenyl($C_1$-$C_8$)alkyl($C_1$-$C_8$)alkenyl, -carbonyl($C_1$-$C_8$)alkanol($C_1$-$C_8$)alkyl, -carbonyl($C_1$-$C_8$)alkenyl($C_1$-$C_8$)alkyl($C_6$-$C_{20}$)aryl, -carbonyl($C_1$-$C_8$)alkenyl($C_6$-$C_{20}$)haloaryl, -carbonyl($C_1$-$C_8$)alkenyl($C_3$-$C_8$)heteroaryl, -carbonyl($C_6$-$C_{20}$)aryl, -carbonyl($C_1$-$C_8$)alkoxy($C_6$-$C_{20}$)aryl, -carbonyl($C_1$-$C_8$)alkyl($C_6$-$C_{20}$)aryl, -carbonylhalo($C_6$-$C_{20}$)aryl, -carbonyl($C_3$-$C_8$)cycloalkyl, -carbonyl($C_1$-$C_8$)alkenyl($C_1$-$C_8$)haloalkyl($C_6$-$C_{20}$)aryl, and -carbonyl($C_1$-$C_8$)alkyl($C_1$-$C_8$)alkoxy($C_6$-$C_{20}$)aryl.

In one embodiment of the invention. $R_1$ is hydrogen, —CO—C(CH$_3$)=CH$_2$, —CO-(E)C(CH$_3$)=CHCH$_2$CH$_3$, —CO-(E)CH=CH-phenyl, —CO-(E)CH=CH-(3,4,5-trimethoxy)phenyl, —CO—CH=C(CH$_3$)$_2$, —CO—CH(Cl)$_2$, —CO—CH$_2$—CH(CH$_3$)$_2$, —CO—CH$_2$C(CH$_3$)(CH$_2$CH$_3$)(OCOCH$_3$), —CO-(E)CH=C(CH$_3$)CH(CH$_3$)$_2$, —CO—CH(CH$_3$)CH$_2$CH$_3$, —CO-(E)CH=C(CH$_3$)CH$_2$CH$_2$CH=C(CH$_3$)$_2$, —CO—CH(CH$_2$CH$_3$)$_2$, —CO—CH$_3$, —CO—CH$_2$C(CH$_3$)CH$_2$CH$_3$, —CO—C(CH$_2$CH$_3$)=CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$, —CO-(E)CH=CHCH$_3$, —CO-(E)CH=CHCH$_2$CH$_3$, —CO-(E)CH=CH-(4-methoxyphenyl), —CO-(E)CH=CH-(4-methylphenyl), —CO-(E)CH=CH-(4-chlorophenyl), —CO-(E)CH=CH(furan-2-yl), —CO-2-thiofuranyl, —CO-phenyl, —CO-(4-methoxyphenyl), —CO-(4-methylphenyl), —CO-(4-bromophenyl), —CO—CH$_2$-naphthalene-1-yl, —CO-cyclopropyl, —CO-cyclopentyl, —CO-cyclohexyl, —CO-(E)CH=CH(3-methoxyphenyl), —CO-benzofuran-2-yl, —CO-benzothiofuran-2-yl, —CO-(E)(CH=CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)(CH=CH-(3-trifluromethoxyphenyl), —CO-(E)CH=CH-(3-trifluromethylphenyl), —CO-(E)CH=CH-(3,4-dimethoxyphenyl), —CO-(E)CH=CH-(3-ethoxyphenyl), —CO—(CH$_2$)$_2$-(naphthalene-1-yl), —CO—CH$_2$-(quinolin-8-yl), —CO—CH—(S—CH$_3$)(6-methoxylnaphthalene-2-yl), —CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH=CH-(4-ethoxyphenyl), —CO-(E)CH=CH-(1,3-benzodioxane-5-yl), or —CO—CH$_2$-(napthalene-1-yl).

In another embodiment of the invention, the compound is selected from the group consisting of 59 compounds as listed in Tables 2 and 6.

In another aspect, the invention relates to a method of preparing the compound of Formula (I)

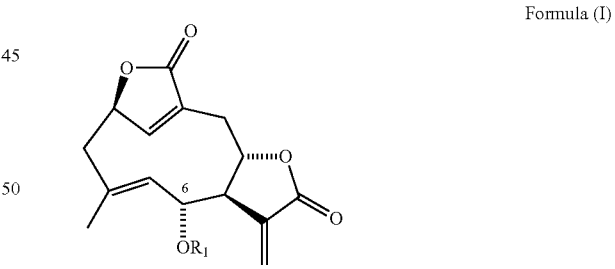

Formula (I)

or a pharmaceutically acceptable salt thereof,
wherein $R_1$ is selected from the group consisting of hydrogen, —CO—C(CH$_3$)=CH$_2$, —CO-(E)C(CH$_3$)=CHCH$_2$CH$_3$, —CO-(E)CH=CH-phenyl, —CO-(E)CH=CH-(3,4,5-trimethoxy)phenyl, —CO—CH=C(CH$_3$)$_2$, —CO—CH(Cl)$_2$, —CO—CH$_2$—CH(CH$_3$)$_2$, —CO—CH$_2$C(CH$_3$)(CH$_2$CH$_3$)(OCOCH$_3$), —CO-(E)CH=C(CH$_3$)CH(CH$_3$)$_2$, —CO—CH(CH$_3$)CH$_2$CH$_3$, —CO-(E)CH=C(CH$_3$)CH$_2$CH$_2$CH=C(CH$_3$)$_2$, —CO—CH(CH$_2$CH$_3$)$_2$, —CO—CH$_3$, —CO—CH$_2$C(CH$_3$)CH$_2$CH$_3$, —CO—C(CH$_2$CH$_3$)=CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$, —CO-(E)CH=CHCH$_3$, —CO-(E)CH=CHCH$_2$CH$_3$, —CO-(E)CH=CH-(4-methoxyphenyl), —CO-(E)CH=CH-(4-methylphenyl), —CO-(E)CH=CH-(4-chlorophenyl), —CO-(E)CH=CH(furan-2-yl), —CO-2-thiofuranyl, —CO-phenyl, —CO-(4-methoxyphenyl), —CO-(4-methylphenyl), —CO-(4-bromophenyl), —CO—CH$_2$-naphthalene-1-yl, —CO-cyclopropyl, —CO-cyclopentyl, —CO-cyclohexyl, —CO-(E)CH=CH(3-methoxyphenyl), —CO-benzofuran-2-yl, —CO-benzothiofuran-2-yl, —CO-(E)CH=CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)CH=CH-(3-trifluromethoxyphenyl), —CO-(E)CH=CH-(3-trifluromethylphenyl), —CO-(E)CH=CH-(3,4-dimethoxyphenyl), —CO-(E)CH=CH-(3-ethoxyphenyl), —CO—(CH$_2$)$_2$-(naphthalene-1-yl), —CO—CH$_2$-(quinolin-8-yl), —CO—CH(S—CH$_3$)(6-methoxylnaphthalene-2-yl), —CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH=CH-(4-ethoxyphenyl), —CO-(E)CH=CH-(1,3-benzodioxane-5-yl), and —CO—CH$_2$-(napthalene-1-yl), the method comprising the steps of:

(1) reacting the compound of Formula (II)

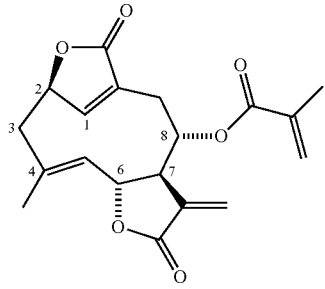

Formula (II)

with aqueous sodium hydroxide to obtain the compound of Formula (I),

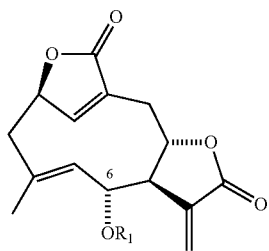

Formula (I)

wherein R$_1$ is hydrogen; and (2) reacting the compound of Formula (I), wherein R$_1$, is hydrogen, with 1-naphthylacetic acid, diethyl azodicarboxylate (DEAD) and triphenylphosphine (PPh3) to afford the compound of Formula (I), wherein R$_1$ is —CO—CH$_2$-(napthalene-1-yl); or (3) reacting the compound of Formula (I), wherein R$_1$ is hydrogen, with 1-(3-dimethylaminopropyl)-3-ethylcarbodiimide hydrochloride (EDCl), dimethylaminopyridine (DMAP), and a compound of Formula (III)

R$_2$COOH            Formula (III), wherein R$_2$ is selected from the group consisting of —CO—C(CH$_3$)=CH$_2$, —CO-(E)C(CH$_3$)=CHCH$_2$CH$_3$, —CO-(E)CH=CH-phenyl, —CO-(E)CH=CH-(3,4,5-trimethoxy)phenyl, —CO—CH=C(CH$_3$)$_2$, —CO—CH(Cl)$_2$, —CO—CH$_2$—CH(CH$_3$)$_2$, —CO—CH$_2$C(CH$_3$)(CH$_2$CH$_3$)(OCOCH$_3$), —CO-(E)CH=C(CH$_3$)CH(CH$_3$)$_2$, —CO—C(CH$_3$)CH$_2$CH$_3$, —CO-(E)CH=C(CH$_3$)CH$_2$CH$_2$CH=C(CH$_3$)$_2$, —CO—CH(CH$_2$CH$_3$)$_2$, —CO—CH$_3$, —CO—CH$_2$C(CH$_3$)CH$_2$CH$_3$, —CO—C(CH$_2$CH$_3$)=CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$, —CO-(E)CH=CHCH$_3$, —CO-(E)CH=CHCH$_2$CH$_3$, —CO-(E)CH=CH-(4-methoxyphenyl), —CO-(E)CH=CH-(4-methylphenyl), —CO-(E)CH=CH(4-chlorophenyl), —CO-(E)CH=CH(furan-2-yl), —CO-2-thiofuranyl, —CO-phenyl, —CO—CH$_2$-naphthalene-1-yl, —CO-(E)CH=CH(3-methoxyphenyl), —CO-benzofuran-2-yl, —CO-benzothiofuran-2-yl, —CO-(E)CH=CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)CH=CH-(3-trifluromethoxyphenyl), —CO-(E)CH=CH-(3-trifluromethylphenyl), —CO-(E)CH=CH-(3,4-dimethoxyphenyl), —CO-(E)CH=CH-(3-ethoxyphenyl), —CO—(CH$_2$)$_2$-(naphthalene-1-yl), —CO—CH$_2$-(quinolin-8-yl), —CO—CH(S—CH$_3$)(6-methoxylnaphthalene-2-yl), —(CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH=CH-(4-ethoxyphenyl), or —CO-(E)CH=CH-(1,3-benzodioxane-5-yl), and —CO—CH$_2$-(napthalene-1-yl), to obtain the compound of Formula (I), wherein R$_1$ is selected from the group consisting of —CO—C(CH$_3$)=CH$_2$, —CO-(E)C(CH$_3$)=CHCH$_2$CH$_3$, —CO-(E)CH=CH-phenyl, —CO-(E)CH=CH-(3,4,5-trimethoxy)phenyl, —CO—CH=C(CH$_3$)$_2$, —CO—CH(Cl$_2$), —CO—CH$_2$—CH(CH$_3$)$_2$, —CO—CH$_2$C(CH$_3$)(CH$_2$CH$_3$)(OCOCH$_3$), —CO-(E)CH=C(CH$_3$)CH(CH$_3$)$_2$, —CO—CH(CH$_3$)CH$_2$CH$_3$, —CO-(E)CH=C(CH$_3$)CH$_2$CH$_2$CH=C(CH$_3$)$_2$, —CO—CH—(CH$_2$CH$_3$)$_2$, —CO—CH$_3$, —CO—CH$_2$C(CH$_3$)CH$_2$CH$_3$, —CO—C(CH$_2$CH$_3$)=CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$, —CO-(E)CH=CHCH$_3$, —CO-(E)CH=CHCH$_2$CH$_3$, —CO-(E)CH=CH-(4-methoxyphenyl), —CO-(E)CH=CH-(4-methylphenyl), —CO-(E)CH=CH-(4-chlorophenyl), —CO-(E)CH=CH(furan-2-yl), —CO-2-thiofuranyl, —CO-phenyl, —CO—CH$_2$-naphthalene-1-yl, —CO-(E)CH=CH(3-methoxyphenyl), —CO-benzofuran-2-yl, —CO-benzothiofuran-2-yl, —CO-(E)CH=CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)CH=CH-(3-trifluromethoxyphenyl), —CO-(E)CH=CH-(3-trifluromethylphenyl), —CO-(E)CH=CH-(3,4-dimethoxyphenyl), —CO-(E)CH=CH-(3-ethoxyphenyl), —CO—(CH$_2$)$_2$-(naphthalene-1-yl), —CO—CH$_2$-(quinolin-8-yl), —CO—CH(S—CH$_3$)(6-methoxylnaphthalene-2-yl), —CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH═CH-(4-ethoxyphenyl), —CO-(E)CH═CH-(1,3-benzodioxane-5-yl), and —CO—CH$_2$-(napthalene-1-yl); or (4) reacting the compound of Formula (I), wherein R$_1$ is hydrogen, with triethylamine and a compound of Formula (IV)

R$_3$COCl                                        Formula (IV), wherein R$_3$ is -(4-methoxyphenyl), -(4-methylphenyl), -(4-bromophenyl), -cyclopropyl, -cyclopentyl, or cyclohexyl to obtain the compound of Formula (I), wherein R$_1$ is —CO-(4-methoxyphenyl), —CO-(4-methylphenyl), —CO-(4-bromophenyl), —CO-cyclopropyl, —CO-cyclopentyl, or —CO-cyclohexyl.

Further in another aspect, the invention relates to a composition comprising an effective amount of a compound as aforementioned or a pharmaceutically acceptable salt thereof; and a pharmaceutically acceptable diluent or carrier.

Further in another aspect, the invention relates to use of a therapeutically effective amount of a compound or a pharmaceutically acceptable salt thereof as aforementioned in the manufacture of a medicament for inhibition of proliferation, migration, mobility, invasion, growth, and/or metastasis of cancer cells in a patient, or for enhancement of an anti-proliferative effect of another anti-cancer drug on cancer cells when treating a patient, or for sensitizing and/or enhancing an anti-cancer effect of a gluthathione synthesis blocker on inhibition of triple negative breast cancer cell activity, or for treatment and/or prophylaxis of lipopolysaccharide-stimulated inflammatory response in a patient, or for all of the above.

Alternatively, the invention relates to a therapeutically effective amount of a compound or a pharmaceutically acceptable salt thereof as aforementioned for use in inhibiting proliferation, migration, mobility, invasion, growth, and/or metastasis of cancer cells in a patient, or for enhancing an anti-proliferative effect of another anti-cancer drug on cancer cells when treating a patient, or for sensitizing and/or enhancing an anti-cancer effect of a gluthathione synthesis blocker on inhibition of triple negative breast cancer cell activity, or for treatment and/or prophylaxis of a lipopolysaccharide-stimulated inflammatory response in a patient, or for all of the above.

Further alternatively, the invention relates to a method of inhibiting proliferation, migration, mobility, invasion, growth, and/or metastasis of cancer cells in a patient, and/or a method of enhancing an anti-proliferative effect of another anti-cancer drug on cancer cells when treating a patient, and/or a method of sensitizing and/or enhancing an anti-cancer effect of a gluthathione synthesis blocker on inhibition of triple negative breast cancer cell activity, and/or a method for treatment and/or prophylaxis of a lipopolysaccharide-stimulated inflammatory response in a patient.

The method comprising administering to a patient a therapeutically effective amount of a compound or a pharmaceutically acceptable salt thereof as aforementioned. The administering step may further comprise administering to the patient an effective amount of another anti-cancer drug selected from the group consisting of PLX4032, buthionine sulfoximine, sulfasalazine paclitaxel, docetaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-PD-1 drug, ipilimumab, doxorubicin, MEK inhibitor, capecitabine, PARP inhibitor, and tamoxifen. The another anti-cancer drug may be co-administered or sequentially administered to the patient.

The lipopolysaccharide-stimulated inflammatory response may be associated with an inflammatory disease selected from the group consisting of inflammatory dermatoses, inflammatory bowel disease, hypersensitivity lung disease, asthma, allergic rhinitis, autoimmune diseases, acute and chronic inflammatory diseases, Sjogren's syndrome, human immunodeficiency virus infection, and cancer.

The gluthathione synthesis blocker may be a gamma-glutamylcysteine synthetase inhibitor or a cystine/glutamate transporter inhibitor.

The another anti-cancer drug may be selected from the group consisting of PLX4032, buthionine sulfoximine, sulfasalazine paclitaxel, docetaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-PD-1 drug, ipilimumab, doxorubicin, MEK inhibitor, capecitabine. PARP inhibitor, and tamoxifen.

In one embodiment of the invention, the medicament exhibits synergism with the another anti-cancer drug.

The cancer may be selected from the group consisting of breast cancer, melanoma, drug-resistant melanoma, brain tumor, lung cancer, lymphoma, neuroepithelioma, kidney cancer, prostate cancer, stomach cancer, colon cancer, and uterus cancer.

Yet in another aspect, the invention relates to use of a therapeutically effective amount of a compound or a pharmaceutically acceptable salt thereof as aforementioned and use of a therapeutically effective amount of one other anti-cancer agent selected from the group consisting of PLX4032, buthionine sulfoximine, sulfasalazine paclitaxel, docetaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-PD-1 drug, ipilimumab, doxorubicin, MEK inhibitor, capecitabine. PARP inhibitor, and tamoxifen in the manufacture of medicaments for combination therapy for inhibition of proliferation, migration, invasion, and/or metastasis of cancer cells in a patient.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 2A-D show the kinetic characteristics of the migration of MDA-MB-231 cells treated with DET and DETD-35. (A) Time-lapse sequence of video frames. (B) Individual trajectories of cells undergoing each treatment are displayed in diagrams. (C) Average migration velocities of cells undergoing each treatment shown at 30-min intervals throughout the observation period. (D) Total migration distances of cells undergoing each treatment after 12 h. Data are mean±SEM with n≥12. Bars labeled with different letters represent significant differences (P<0.05, one-way ANOVA).

FIGS. 3A-D show DET and DETD-35 inhibits orthotopic MDA-MB-231 mammary tumor growth in female NOD/SCID mice. (A) Animal body weights. (B) The measured MDA-MB-231 tumor growth in mice with or without DETD-35 (10 mg/kg body weight, i.p.) treatment. (C) Tumors and tumor size at day 71. (D) Organ index in different groups of mice was analyzed.

FIGS. 4A-B show the effect of DETD-35 on the lung metastasis of MDA-MB-231 triple negative mammary tumors in xenograft SCID mice. (A) Number of metastatic pulmonary foci in the lung organ in different treatment groups was calculated. (B) Organ index in different treatment groups were analyzed (P<0.05; one-way ANOVA).

FIGS. 9 A-D show in vivo anti-tumor activity of DET or DETD-35 alone, or in combination with PLX4032 against A375 melanoma. (A) Experimental design of the study. (B) Representative pictures of isolated tumor tissue from each treatment groups. (C) Mean tumor volume after a 33-day of tumor cell implantation with or without compound treatment. (D) Average tumor mass of each treatment groups. Data are mean±SEM, n=8. Means without a common letter differ, P<0.05 (ANOVA).

DETAILED DESCRIPTION OF THE INVENTION

Definitions

Figure 1A:
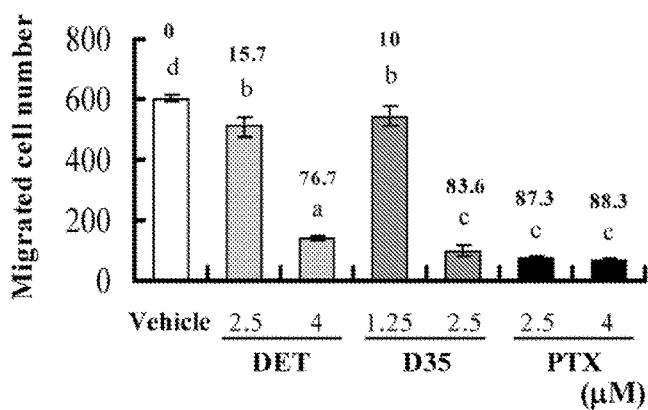
FIGS. 1A-B are representative photomicrographs showing Boyden chamber assay results of MDA-MB-231 cells treated with vehicle. DET, DETD-35 and PTX, respectively for 24 h. (A) migration assay and (B) invasion assay. Cells were stained with DAPI. Data are mean±SEM of three independent experiments. Different letters indicate significant differences (*P<0.05, one-way ANOVA).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around". "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or "treatment" refers to administration of an effective amount of a therapeutic agent to a subject in need thereof with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active agent that is required to confer a therapeutic effect on the treated subject. Effective doses will vary, as recognized by those skilled in the art, depending on routes of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

HED=animal dose in mg/kg×(animal weight in kg/human weight in kg)$^{0.33}$.

E and Z designate configuration of double bond. R and S designate position above and below the plane of the molecule.

The term "PLX4032" refers to "Vemurafenib".

The term "CTLA-4" refers to cytotoxic T-lymphocyte-associated protein 4. Anti-CTLA-4 drugs include, but are not limited to, Ipilimumab.

The term "PD-1" refers to "Programmed cell death protein I". Anti-PD-1 drugs include, but are not limited to, nivolumab.

A MEK inhibitor is a chemical or drug that inhibits the mitogen-activated protein kinase kinase enzymes MEK1 and/or MEK2. They can be used to affect the MAPK/ERK pathway which is often overactive in some cancers. MEK inhibitors include, but are not limited to, Trametinib, Selumetinib, Binimetinib, PD-325901, Cobimetinib CI-1040, and PD035901.

PARP inhibitors are inhibitors of the enzyme poly ADP ribose polymerase (PARP). They are developed for multiple indications; the most important is the treatment of cancer.

PARP inhibitors include, but are not limited to, Iniparib, Talazoparib, Olaparib, Rucaparib, Veliparib, CEP 9722, MK4827, and BGB-290.

The invention also relates to provision of adjuvant or alternative strategy and method for treating cancer and minimize chemotherapy resistance that are expected to prolong cancer patients' life span. For example, a combinational intervention of DET derivatives with anti-BRAF$^{V600E}$ or with the melanoma drug vemurafenib can overcome drug resistance or reduce side effects.

Examples

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods
Reagents 3-(4,5-Dimethylthiazol-2-yl)-2,5-diphenyltetrazolium bromide (MTT), dimethyl sulfoxide (DMSO) and lipopolysaccharide (LPS) were purchased from Sigma Chemical Co. (St. Louis, Mo.). Vemurafenib (PLX4032) and MEK inhibitor (PD0325901) were purchased from Selleckehem (Houston, Tex.). Sulfasalazine was purchased from Fluka (Buchs, Switzerland). Buthionine sulfoximine and other solvent or chemicals were purchased from Sigma-Aldrich or of reagent grade.

Preparation of Deoxyelephantopin (DET) Compound

The whole dry plant materials of *Elephantopus scaber* L. (Asteraceae) was extracted with 3 volume of acetone for 3 days and repeated 2~3 times, then the crude extract was partitioned with ethyl acetate (EA) to yield the EA fraction. The EA extract was chromatographed on a silica gel column with hexane (H)/EA eluting solvents (by H:E/3:1, H:E/1:1 and H:E/1:2, v/v). The DET containing fraction was confirmed by thin layer chromatography or by HPLC analysis. The HPLC condition for confirming DET fractions or DET purity was carried out by using RP-18 silica gel column (5μ, 150×4.6 mm) eluted with 55% MeOH. The enriched DET fractions were collected and chromatographed on a RP-C18 column in an MPLC system with the solvent elution conditions: 30% methanol (MeOH), 2.5 column volume (CV), 30-55% MeOH, 5 CV, and 55% MeOH, 9.5 CV. The enriched DET fractions were collected and evaporated to dry form by rotavapor. The dry chemical powder was dissolved in acetone to get DET crystals. The structure of DET was elucidated by electrospray ionization mass spectrometry (ThermoFinnigan LCQ, San Jose, Calif., USA) and $^1$H and $^{13}$C NMR (Brüker ADVANCE 500 AV) spectrometry and confirmed by comparison of the spectral data with previously published results.

Organic Synthesis of DET Derivatives
DETD-1:
DETD-1 was synthesized and the structure confirmed by following the method and data published elsewhere.

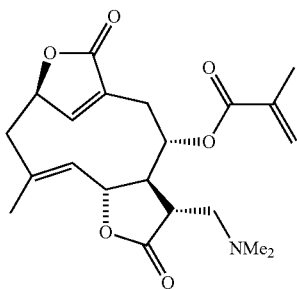

DETD-1

DETD-3 to DETD-62:

DETD-3 was derived from DET and DETD-4 to DETD-62 were derived from DETD-3 as shown in scheme 1.

centrated in vacuo. The residue was purified with column chromatography on $SiO_2$ to obtain the novel C-8 lactone DETD-3 (0.744 g, 91%)

Spectral Data of DETD-3:

High-Resolution Mass Spectroscopy: m/z calcd for $C_{15}H_{16}O_5$ (M$^+$+Na) 299.0890, found 299.0883. Proton Nuclear Magnetic Resonance ($^1$H-NMR, 400 MHz, 2% $CD_3OD/CDCl_3$) σ 6.94 (1H, s), 6.41 (1H, dd, J=2.9 and 1.2 Hz), 6.32 (1H, d, J=2.9 Hz), 5.47-5.43 (1H, m), 4.56 (1H, br d, J=10.0 Hz), 4.27 (1H, t, J=9.7 Hz), 4.10 (1H, ddd, J=10.7, 6.4 and 1.6 Hz), 3.19 (1H, ddd, J=13.1, 3.8 and 1.6 Hz), 2.89-2.82 (1H, m), 2.77 (1H, dd, J=13.5 and 4.7 Hz), 2.67 (1H, dd, J=13.1 and 10.7 Hz), 2.57 (1H, br d, J=13.5 Hz), 1.71 (3H, d, J=1.4 Hz). Carbon 13 Nuclear Magnetic Resonance ($^{13}$C-NMR, 400 MHz, DMSO-d$_6$) σ 172.9, 169.4, 155.2, 140.3, 136.3, 127.2, 126.2, 125.7, 80.9, 78.5, 67.7, 50.9, 40.5, 31.8, 19.0.

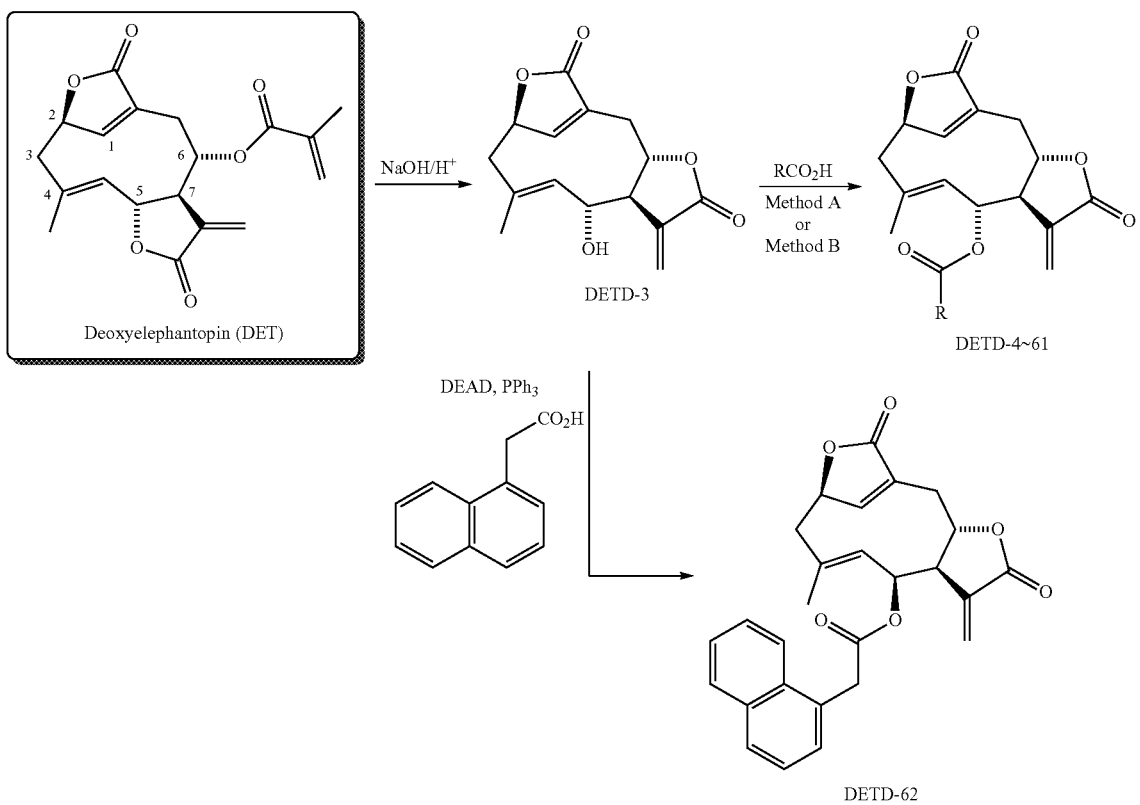

Scheme 1

DETD-3 is a novel C-8 lactonic DET. The synthesis of the novel C-8 lactonic derivative DETD-3 involves the hydrolysis of DET with strong base such as NaOH followed by an acidic treatment.

Figure 12:
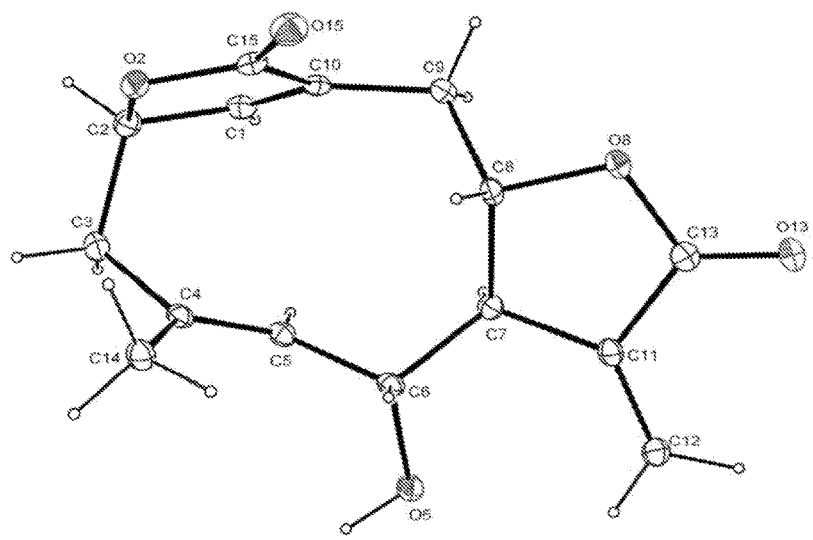
FIG. 12 shows the X ray crystal structure of DETD-3.

Procedure:

To a solution of DET (1.023 g) in dioxane (25 mL), aqueous 1N NaOH (25 mL) was added at 0° C. The mixture was stirred at room temperature overnight and cooled to 0° C. The mixture was acidified with aqueous 2N HCl and stirred for 30 min. The whole was extracted twice with AcOEt then 5% MeOH/AcOEt. The combined organic layers were washed with brine, dried over $Na_2SO_4$, and con- The X ray crystal structural analysis of DETD-3 was carried. FIG. 12 shows the X-ray structure of DETD-3. The crystal data and structure refinement parameters are shown in Table 1.

TABLE 1

| Parameters | |
|---|---|
| Empirical formula | $C_{15}H_{16}O_5$ |
| Formula weight | 276.28 |
| Temperature | 100.0(1) K |
| Wavelength | 0.71073 Å |
| Crystal system | Orthorhombic |
| Space group | P2(1)2(1)2(1) |

TABLE 1-continued

| Parameters | |
|---|---|
| Unit cell dimensions | a = 7.5941(3) Å  α = 90°. |
| | b = 8.0981(2) Å  β = 90°. |
| | c = 21.3331(7) Å  γ = 90°. |
| Volume | 1311.94(7) Å$^3$ |
| Z | 4 |
| Density (calculated) | 1.399 Mg/m$^3$ |
| Absorption coefficient | 0.105 mm$^{-1}$ |
| F(000) | 584 |
| Crystal size | 0.28 × 0.2 × 0.18 mm$^3$ |
| Theta range for data collection | 1.91 to 26.37° |
| Index ranges | −9 ≤ h ≤ 6, −10 ≤ k ≤ 6, −26 ≤ 1 ≤ 26 |
| Reflections collected | 6135 |
| Independent reflections | 2611 [R(int) = 0.0221] |
| Completeness to theta = 25.00° | 100.0% |
| Absorption correction | Semi-empirical from equivalents |
| Max. and min. transmission | 0.9703 and 0.8318 |
| Refinement method | Full-matrix least-squares on F$^2$ |
| Data/restraints/parameters | 2611/0/246 |
| Goodness-of-fit on F$^2$ | 1.042 |
| Final R indices [I > 2 sigma (I)] | R1 = 0.0302, wR2 = 0.0655 |
| R indices (all data) | R1 = 0.0352, wR2 = 0.0682 |
| Absolute structure parameter | 0.0 (9) |
| Extinction coefficient | 0.005 (1) |
| Largest diff. peak and hole | 0.195 and −0.147 e · Å$^{-3}$ |

Preparation of DET Derivatives (DETD) from DETD-3
Procedure:

Alcohol at C-6 on DETD-3 can be further esterified to afford various esters DETD-4 to DETD-62 by three kinds of standard methods.

[Method A]

To a solution of DETD-3 in methylene chloride, the related carboxylic acid (RCOOH), 1-(3-dimethylaminopropyl)-3-ethylcarbodiimide hydrochloride (EDCI) and dimethylaminopyridine (DMAP) were added. The mixture was stirred at room temperature overnight. Standard work-up was performed to obtain esters DETD-4 to DETD-31, DETD-35, and DETD-39 to DETD-61.

[Method B]

To a solution of DETD-3 in methylene chloride, the related acid chloride (RCOCl) and triethylamine were added. The mixture was stirred at room temperature overnight. Standard work-up was performed to obtain the related esters DETD-32 to DETD-34 and DETD-36 to DETD-38.

[Method C]

A solution of DETD-3 in tetrahydrofuran was treated with 1-naphthylacetic acid under standard Mitsunobu condition [diethyl azodicarboxylate (DEAD), triphenylphosphine (PPh$_3$)] at room temperature to provide DETD-62 (epi-DETD-35).

R group can be alkyl, brunched alkyl, cyclic alkyl, substituted alkyl, aromatic, substituted aromatic, hetero aromatic, substituted hetero aromatic, alkenyl, alkynyl, et al.

Spectra Data:

The Proton Nuclear Magnetic Resonance of DETDs compounds are shown below.

DETD-4 (Method A): ($^1$H-NMR, 400 MHz, CDCl$_3$) σ 6.93 (1H, s), 6.40 (1H, d, J=2.7 Hz), 7.516.10 (1H, d, J=9.6 Hz), 5.94 (1H, d, J=2.1 Hz), 5.65 (1H, s), 5.45 (1H, br s), 5.39 (1H, t, J=10.0 Hz), 4.57 (1H, d, J=10.0 Hz), 4.23 (1H, dd, J=10.1 and 6.5 Hz), 3.28 (1H, d, J=13.1 Hz), 3.15 (1H, ddd, J=10.0, 6.5 and 3.3 Hz), 2.79 (1H, dd, J=13.6 and 4.9 Hz), 2.68 (1H, dd, J=13.1 and 10.8 Hz), 2.54 (1H, d, J=13.6 Hz), 1.95 (3H, s), 1.87 (3H, s).

DETD-5 (Method A, including 2% of cis-isomer): ($^1$H-NMR, 400 MHz, CDCl$_3$) σ 6.91 (1H, s), 6.75 (1H, dt, J=7.4 and 1.2 Hz), 6.39 (1H, d, J=2.9 Hz), 7.515.93 (1H, d, J=2.9 Hz), 5.48-5.40 (1H, m), 5.39 (1H, t, J=10.0 Hz), 4.46 (1H, d, J=10.0 Hz), 4.23 (1H, ddd, J=10.7, 6.6 and 1.6 Hz), 3.32-3.22 (1H, m), 3.19-3.02 (2H, m), 2.78 (1H, dd, J=13.5 and 4.9 Hz), 2.68 (1H, dd, J=13.1 and 10.8 Hz), 2.53 (1H, d, J=13.5 Hz), 2.25-2.16 (2H, m), 1.86 (3H, d, J=1.4 Hz), 1.83 (3H, s), 1.06 (3H, t, =7.5 Hz).

DETD-6 (Method A): ($^1$H-NMR, 400 MHz, CDCl$_3$) σ 7.71 (1H, d, J=16.0 Hz), 7.55-7.50 (2H, m), 7.44-7.38 (3H, m), 6.94 (1H, s), 6.41 (1H, d, J=9.6 Hz), 7.516.40 (1H, d, J=16.0 Hz), 6.00 (1H, d, J=2.5 Hz), 5.50-5.44 (2H, m), 4.51 (1H, d, J=10.0 Hz), 4.25 (1H, ddd, J=10.5, 6.5 and 1.6 Hz), 3.33-3.26 (1H, m), 3.19-3.11 (1H, m), 2.80 (1H, dd, J=13.5 and 4.9 Hz), 2.69 (1H, dd, J=13.1 and 10.7 Hz), 2.55 (1H, d, J=13.5 Hz), 1.89 (3H, d, J=1.4 Hz).

DETD-7 (Method A): ($^1$H-NMR, 400 MHz, CDCl$_3$) σ 7.61 (1H, d, J=15.8 Hz), 6.93 (1H, s), 6.74 (2H, d, J=9.6 Hz), 7.516.41 (1H, d, J=2.8 Hz), 6.31 (1H, s), 6.27 (1H, s), 6.00 (1H, d, J=2.8 Hz), 5.52-5.43 (2H, m), 4.50 (1H, d, J=10.1 Hz), 4.26 (1H, ddd, =10.1, 6.6 and 1.7 Hz), 3.89 (9H, s), 3.29 (1H, dd, J=13.1 and 1.7 Hz), 3.14 (1H, ddd. J=13.1, 6.6 and 3.1 Hz), 2.81 (1H, dd, J=13.1 and 4.8 Hz), 2.69 (1H, dd, J=13.1 and 10.7 Hz), 2.54 (1H, d, J=13.1 Hz), 1.89 (3H, d, J=1.4 Hz).

DETD-8 (Method A): ($^1$H-NMR, 400 MHz, CDCl$_3$) σ 6.92 (1H, s), 7.516.39 (1H, d, J=2.9 Hz), 5.96 (1H, d, J=2.9 Hz), 5.69 (1H, s), 5.47-5.41 (1H, m), 5.52-5.43 (2H, m), 5.34 (1H, t, J=10.0 Hz), 4.45 (1H, d, J=9.6 Hz), 4.25-4.17 (1H, m), 3.26 (1H, d, J=13.1 Hz), 3.10-3.01 (1H, m), 2.78 (1H, dd, J=13.1 and 4.9 Hz), 2.66 (1H, dd, J=13.1 and 10.7 Hz), 2.53 (1H, d, J=13.1 Hz), 2.16 (3H, s), 1.92 (3H, s), 1.86 (3H, s).

DETD-9 (Method A): ($^1$H-NMR, 400 MHz, CDCl$_3$) σ 6.95 (1H, s), 6.50 (1H, d, =2.9 Hz), 6.19 (1H, d, J=2.9 Hz), 5.93 (1H, s), 5.50-5.44 (1H, m), 5.32 (1H, t, J=10.1 Hz), 4.20 (1H, ddd, J=10.1, 6.5, and 1.5 Hz), 3.28 (1H, br d, J=13.1 Hz), 3.21 (1H, ddd, J=13.1, 6.3, and 3.1 Hz), 2.83 (1H, dd, J=13.1 and 4.8 Hz), 2.69 (1H, dd, J=13.1 and 10.7 Hz), 2.57 (1H, d, J=13.1 Hz), 1.86 (3H, d, J=1.2 Hz).

DETD-10 (Method A): ($^1$H-NMR, 400 MHz, CDCl$_3$) σ 6.92 (1H, s), 6.42 (1H, d, J=2.8 Hz), 5.97 (1H, d, J=2.8 Hz), 5.46-5.42 (1H, m), 5.28 (1H, t, J=10.1 Hz), 4.42 (1H, d, J=10.0 Hz), 4.16 (1H, ddd, J=10.0, 6.5, and 1.6 Hz), 3.26 (1H, dd, J=13.1 and 1.6 Hz), 3.05 (1H, ddd, J=13.0, 6.2, and 3.2 Hz), 2.79 (1H, dd, J===13.1 and 4.8 Hz), 2.65 (1H, dd, J=13.1 and 10.7 Hz), 2.53 (1H, d, J=13.1 Hz), 2.24-2.14 (2H, m), 2.14-2.03 (1H, m), 1.84 (3H, d, J=1.2 Hz), 0.93 (6H, d, J=6.6 Hz).

DETD-11 (Method A): ($^1$H-NMR, 400 MHz, CDCl$_3$) σ 6.92 (1H, br s), 6.50-6.42 (1H, m), 6.17-5.95 (1H, m), 5.44 (1H, br s), 5.31-5.11 (1H, m), 4.46-4.32 (1H, m), 4.24-4.15 (1H, m), 3.26 (1H, br d, J=12.9 Hz), 3.14-3.02 (1H, m), 2.80 (1H, dd, J=13.5 and 4.9 Hz), 2.70-2.61 (1H, m), 2.60-2.51 (1H, m), 2.06 (3H, s), 1.84 (3H, br s), 0.88 (3H, t, J=7.6 Hz).

DETD-12 (Method A): ($^1$H-NMR, 400 MHz, CDCl$_3$) σ 6.91 (1H, s), 6.40 (1H, d, J=2.5 Hz), 5.96 (1H, d, J=2.5 Hz), 5.63 (1H, s), 5.46-5.41 (1H, m), 5.34 (1H, t, J=10.1 Hz), 4.46 (1H, d, J=10.1 Hz), 4.24-4.16 (1H, m), 3.30-3.22 (1H, m), 3.10-3.02 (1H, m), 2.78 (1H, dd, J=13.5 and 4.7 Hz), 2.66 (1H, dd, J=13.1 and 10.7 Hz), 2.53 (1H, d, J=13.5 Hz), 2.44-2.34 (1H, m), 2.12 (3H, d, J=1.3 Hz), 1.86 (3H, d, J=1.3 Hz), 1.07 (3H, t, J=6.8 Hz).

DETD-13 (Method A): ($^1$H-NMR, 400 MHz, CDCl$_3$) σ 6.92 (1H, s), 6.43 (1H, d, J=2.8 Hz), 6.0 and 5.98 (1H, d, J=2.8 Hz, 1:1), 5.46-5.41 (1H, m), 5.25 (1H, t. J=10.1 Hz), 4.41 (1H, d, J=10.3 Hz), 4.19 (1H, dd, J=10.3 and 6.3 Hz), 3.07 (1H, ddd, J=13.1, 6.4 and 3.3 Hz), 2.79 (1H, dd, J=13.5 and 4.9 Hz), 2.66 (1H, dd, J=13.1 and 10.5 Hz), 2.53 (1H, d, J=13.5 Hz), 2.40-2.30 (1H, m), 1.84 (3H, brs), 1.72-1.58 (1H, m), 1.55-1.40 (1H, m), 1.13 and 1.12 (3H, d, J=7.0 Hz, 1:1), 0.88 and 0.87 (3H, t, J=7.4 Hz, 1:1).

DETD-14 (Method A): ($^1$H-NMR, 400 MHz, CDCl$_3$) σ 6.93 (1H, s), 6.48-6.32 (1H, m), 6.06-5.88 (1H, m), 5.44 (1H, br s), 5.40-5.20 (1H, m), 5.16-5.01 (1H, m), 4.51-4.39 (1H, m), 4.24-4.13 (1H, m), 3.29-3.20 (1H, m), 3.14-3.00 (1H, m), 2.84-2.50 (4H, m), 2.17 and 2.14 (3H, br s), 1.86 and 1.83 (3H, br s), 1.99-1.56 (10H, m).

DETD-16 (Method A): ($^1$H-NMR 400 MHz, CDCl$_3$) σ 6.92 (1H, s), 6.44 (1H, dd, J=3.1 and 0.8 Hz), 6.02 (1H, dd, J=2.6 and 0.8 Hz), 5.46-5.41 (1H, m), 5.26 (1H, t, J=10.1 Hz), 4.40 (1H, br 4, J=10.1 Hz), 4.18 (1H, ddd, J=10.1, 6.3 and 1.7 Hz), 3.26 (1-1H, dd, J=13.0 and 2.2 Hz), 3.07 (1H, ddd, J=13.0, 6.1 and 3.0 Hz), 2.79 (1H, dd, J=13.5 and 4.6 Hz), 2.65 (1H, dd, J=13.0 and 10.7 Hz), 2.53 (1H, br d, J=13.5 Hz), 2.22-2.14 (1H, m), 1.85 (3H, d, J=1.4 Hz), 1.66-1.44 (41-1H, m), 0.86 (3H, t, J=1.4 Hz), 0.85 (3H, t, J=1.4 Hz).

DETD-17 (Method A): ($^1$H-NMR, 400 MHz, CDCl$_3$) σ 6.93 (1H, s), 6.43 (1H, dd, J=3.1 and 0.8 Hz), 5.96 (1H, dd, J=2.7 and 0.8 Hz), 5.47-5.42 (1H, m), 5.28 (1H, t. J=10.0 Hz), 4.44 (1H, br d, J=10.0 Hz), 4.18 (1H, ddd, J=10.7, 6.4 and 1.7 Hz), 3.27 (1H, ddd, J=13.3, 3.8 and 1.7 Hz), 3.05 (1H, ddd, J=13.0, 6.4 and 3.1 Hz), 2.79 (1H, dd, J=13.5 and 4.9 Hz), 2.65 (1H, dd. J=13.0 and 10.7 Hz), 2.53 (1H, br d, J=13.5 Hz), 2.06 (3H, s), 1.83 (3H, d, J=1.4 Hz).

DETD-18 (Method A): ($^1$H-NMR, 400 MHz, CDCl$_3$) σ 6.92 (1H, s), 6.43 (1H, d, J=3.1 Hz), 5.97 (1H, d, J=2.7 Hz), 5.46-5.41 (1H, m), 5.28 and 5.27 (1H, t, J=10.0 Hz, 1:1), 4.42 (1H, d, J=10.0 Hz), 4.18 (1H, dd, J=10.6 and 6.1 Hz), 3.26 (1H, br d, J=13.3 Hz), 3.09-3.01 (1H, m), 2.79 (1H, dd, J=13.5 and 4.8 Hz), 2.65 (1H, dd. J=13.1 and 10.7 Hz), 2.53 (1H, d, J=13.5 Hz), 2.32 and 2.28 (1H, dd, J=15.0 and 6.1 Hz, 1:1), 2.14-2.03 (1H, m), 1.92-1.80 (1H, m), 1.84 (3H, d, J=1.2 Hz), 1.39-1.15 (4H, m), 0.92-0.85 (6H, m).

DETD-19 (Method A): ($^1$H-NMR, 400 MHz, CDCl$_3$) σ 6.92 (1H, s), 6.40 (1H, d, J=3.1 Hz), 6.12 (1H, d, J=0.6 Hz), 5.93 (1H, d, J=2.7 Hz), 5.61 (1H, d, J=1.4 Hz), 5.47-5.42 (1H, m), 5.41 (1H, t, J=10.0 Hz), 4.47 (1H, d, J=10.0 Hz), 4.23 (1H, ddd, J=10.5, 6.5 and 1.7 Hz), 3.28 (1H, dd, J=13.3 and 1.8 Hz), 3.14 (1H, ddd, J=12.8, 6.5, and 3.3 Hz), 2.79 (1H, dd, J=13.5 and 4.9 Hz), 2.68 (1H, dd, J=13.1 and 10.6 Hz), 2.53 (1H, d, J=13.5 Hz), 2.38-2.26 (2H, m), 1.86 (3H, d, J=1.4 Hz), 1.07 (3H, t, J=7.4 Hz).

DETD-20 (Method A): ($^1$H-NMR, 400 MHz, CDCl$_3$) σ 6.92 (1H, br s), 6.44 (1H, d, J=3.1 Hz), 6.02-5.96 (1H, m), 5.46-5.42 (1H, m), 5.24 and 5.23 (1H, t, J=10.1 Hz, 1:1), 4.40 (1H, d, J=9.8 Hz), 4.18 (1H, dd. J=9.8 and 6.4 Hz), 3.27 (1H, dd, J=13.1 and 1.6 Hz), 3.12-3.04 (1H, m), 2.79 (1H, dd, J=13.6 and 4.8 Hz), 2.66 (1H, dd, J=13.1 and 10.7 Hz), 2.53 (1H, d, J=13.5 Hz), 2.48-2.36 (1H, m), 1.84 (3H, br s), 1.68-1.55 (1H, m), 1.44-1.22 (3H, m), 1.13 and 1.12 (3H, d, J=6.9 Hz, 1:1), 0.89 (3H, t, J=7.2 Hz).

DETD-21 (Method A): ($^1$H-NMR, 400 MHz, CDCl$_3$) σ 6.94 (1H, br s), 6.43 (1H, d, J=2.9 Hz), 6.01 (1H, d, J=2.5 Hz), 5.46-5.42 (1H, m), 5.26 (1H, t, J=10.3 Hz), 4.40 (1H, d, J=10.0 Hz), 4.22-4.14 (1H, m), 3.25 (1H, dd, J=13.1 and 1.8 Hz), 3.12-3.03 (1H, m), 2.79 (1H, dd, J=13.5 and 4.9 Hz), 2.66 (1H, dd, J=13.1 and 10.7 Hz), 2.52 (1H, d, J=13.5 Hz), 2.28-2.20 (1H, m), 1.85 (3H, d, J=1.2 Hz), 1.69-1.38 (4H, m), 1.35-1.10 (4H, m), 0.92-0.81 (6H, m).

DETD-22 (Method A): ($^1$H-NMR, 400 MHz, CDCl$_3$) σ 6.93 (1H, br s), 6.43 (1H, br d, J=3.1 Hz), 6.00 (1H, br d, J=2.5 Hz), 5.47-5.42 (1H, m), 5.24 (1H, t, J=10.0 Hz), 4.41 (1H, d, J=10.0 Hz), 4.18 (1H, ddd, J=10.7, 6.3 and 1.6 Hz), 3.25 (1H, dd, J=13.1 and 2.0 Hz), 3.07 (1H, ddd, J=12.7, 6.4, and 3.1 Hz), 2.79 (1H, dd, J=13.5 and 4.8 Hz), 2.66 (1H, dd, J=13.1 and 10.7 Hz), 2.53 (1H, d, J=13.5 Hz), 2.45-2.34 (1H, m), 1.84 (3H, d, J 1.4 Hz), 1.70-1.54 (2H, m), 143-1.16 (4H, m), 1.13 (3H, d, J=7.0 Hz), 0.88 (3H, t, J=7.0 Hz).

DETD-23 (Method A): ($^1$H-NMR, 400 MHz, CDCl$_3$) σ 6.92 (1H, s), 6.45 (1H, d, J=3.1 Hz), 5.99 (1H, d, J=2.5 Hz), 5.48-5.42 (1H, m), 5.29 (1H, t, J=10.1 Hz), 4.41 (1H, brd, br J=10.1 Hz), 4.19 (1H, ddd, J=10.1, 6.4 and 1.6 Hz), 3.76 (1H, br s), 3.26 (1H, dd, J=13.1 and 2.0 Hz), 3.12-3.04 (1H, m), 2.80 (1H, dd, J=13.4 and 4.8 Hz), 2.66 (1H, dd, J=13.1 and 10.0 Hz), 2.52 (1H, br d, J=13.4 Hz), 2.40 (2H, s), 1.98-1.88 (2H, m), 1.83 (3H, d, J=1.4 Hz), 0.91 (6H, t, J=7.3 Hz), 0.89-0.82 (6H, m).

DETD-24 (Method A): ($^1$H-NMR, 400 MHz, CDCl$_3$) σ 7.01 (1H, dd, J=15.4 and 6.9 Hz), 6.93 (1H, s), 6.39 (1H, d, J=3.1 Hz), 5.94 (1H, d, J=2.7 Hz), 5.83 (1H, dd, J=15.4 and 1.8 Hz), 5.48-5.42 (1H, m), 5.38 (1H, t, J=10.1 Hz), 4.46 (1H, br d, J=10.0 Hz), 4.22 (1H, ddd, J=10.7, 6.6 and 1.6 Hz), 3.26 (1H, dd, J=13.1 and 2.0 Hz), 3.10 (1H, ddd, J=12.8, 6.6 and 3.2 Hz), 2.78 (1H, dd, J=13.4 and 4.9 Hz), 2.67 (1H, dd, J=13.4 and 10.7 Hz), 2.53 (1H, br d, J=13.4 Hz), 1.91 (3H, dd, J=6.9 and 1.8 Hz), 1.85 (3H, d, J=1.4 Hz).

DETD-25 (Method A): ($^1$H-NMR, 400 MHz, CDCl$_3$) σ 7.05 (1H, dt, J=15.6 and 6.4 Hz), 6.93 (1H, s), 6.40 (1H, dd, J=8.5 and 3.0 Hz), 5.96 (1H, dd, J=14.6 and 2.5 Hz), 5.79 (1H, dt, J=15.6 and 1.7 Hz), 5.48-5.42 (1H, m), 5.38 (1H, t, J=10.1 Hz), 4.45 (1H, t, J=10.0 Hz), 4.26-4.15 (1H, m), 3.31-3.20 (1H, m), 3.16-3.00 (2H, m), 2.78 (1H, dd, J=13.7 and 4.9 Hz), 2.54 (1H, br d, J=13.5 Hz), 2.30-2.20 (1H, m), 1.85 (3H, d, J=1.4 Hz), 1.08 (3H, t, J=7.4 Hz).

DETD-26 (Method A): ($^1$H-NMR, 400 MHz, CDCl$_3$) σ 7.66 (1H, d, J=15.9 Hz), 7.47 (2H, d, J=8.9 Hz), 6.92 (1H, s), 6.91 (2H, d, J=8.9 Hz), 6.41 (1H, d, J=2.9 Hz), 6.26 (1H, d, J=15.9 Hz), 6.01 (1H, d, J=2.3 Hz), 5.46 (1H, J=10.1 Hz), 5.47-5.43 (1H, m), 4.50 (1H, d, =10.1 Hz), 4.25 (1H, ddd, J=10.6, 6.7 and 1.7 Hz), 3.85 (3H, s), 3.29 (1H, br d, J=11.3 Hz), 3.14 (1H, ddd, J=12.8, 6.4 and 3.2 Hz), 2.80 (1H, dd J=13.4 and 4.9 Hz), 2.69 (1H, dd, J=13.4 and 10.6 Hz), 2.54 (1H, d, J=13.4 Hz), 1.88 (3H, d, J=1.4 Hz).

DETD-27 (Method A): ($^1$H-NMR, 400 MHz, CDCl$_3$) σ 7.67 (1H, d, J=16.0 Hz), 7.41 (2H, d, J=8.0 Hz), 7.20 (2H, d, J=8.0 Hz), 6.93 (1H, s), 6.41 (1H, d, J=2.9 Hz), 6.34 (1H, d, J=16.0 Hz), 6.00 (1H, d, J=2.3 Hz), 5.46 (1H, t, J=10.0 Hz), 5.48-5.43 (1H, m), 4.50 (1H, d, J=10.0 Hz), 4.25 (1H, ddd, J=10.6, 6.7 and 1.7 Hz), 3.29 (1H, dd, =13.2 and 2.0 Hz), 3.14 (1H, ddd. J=12.7, 6.3 and 3.2 Hz), 2.80 (1H, dd, J=13.4 and 4.8 Hz), 2.69 (1H, dd, J=13.4 and 10.7 Hz), 2.54 (1H, d, J=13.4 Hz), 2.38 (3H, s), 1.88 (3H, d, J=1.4 Hz).

DETD-28 (Method A): ($^1$H-NMR, 400 MHz, CDCl$_3$) σ 7.65 (1H, d, J=15.8 Hz), 7.45 (2H, d, J=8.6 Hz), 7.37 (2H, d, J=8.6 Hz), 6.93 (1H, s), 6.41 (1H, d, J=3.1 Hz), 6.37 (1H, d, J=16.0 Hz), 5.98 (1H, d J=2.1 Hz), 5.46 (1H, t, J=10.1 Hz), 5.48-5.43 (1H, m), 4.50 (1H, d, J=10.0 Hz), 4.25 (1H, ddd, J=10.7, 6.6 and 1.6 Hz), 3.29 (1H, br d, J=11.2 Hz), 3.14 (1H, ddd, J=12.7, 6.4 and 3.2 Hz), 2.80 (1H, dd, J=13.4 and 4.9 Hz), 2.69 (1H, dd, J=13.4 and 10.7 Hz), 2.54 (1H, d, J=13.4 Hz), 2.38 (3H, s), 1.88 (3H, d, J=1.4 Hz).

DETD-29 (Method A): ($^1$H-NMR, 400 MHz, 3% CD$_3$OD in CDCl$_3$) σ 7.51 (1H, s), 7.43 (1H, d, J=16.0 Hz), 6.96 (1H, br s), 6.65 (1H, d, J=3.1 Hz), 6.52-6.48 (1H, m), 6.41 (1H, d, J=3.1 Hz), 6.28 (1H, d, J=16.0 Hz), 6.01 (1H, d, J=2.5 Hz), 5.50-5.41 (2H, m), 5.48-5.44 (1H, m), 4.50 (1H, d, J=10.1 Hz), 4.24 (1H, dd, J=10.5 and 6.4 Hz), 3.27 (1H, d, J=12.8 Hz), 3.19-3.10 (1H, m), 2.80 (1H, dd, J=13.7 and 5.0 Hz), 2.70 (1H, dd, J=12.8 and 11.0 Hz), 2.55 (1H, d, J=13.7 Hz), 1.88 (3H, s).

DETD-30 (Method A): ($^1$H-NMR, 400 MHz, CDCl$_3$) σ 7.81 (1H, dd, J=3.8 and 1.2 Hz), 7.60 (1H, dd, J=5.0 and 1.2 Hz), 7.14 (1H, dd, J=5.0 and 3.8 Hz), 6.94 (1H, br s), 6.41 (1H, d, J=3.1 Hz), 6.08 (1H, d, J=2.5 Hz), 5.51 (1H, t, J=10.1 Hz), 5.48-5.44 (1H, m), 4.55 (1H, br d, J=10.0 Hz), 4.26 (1H, ddd, J=10.7, 6.5 and 1.6 Hz), 3.30 (1H, br d, J=13.2 Hz), 3.23 (1H, ddd, J=12.8, 6.4 and 3.1 Hz), 2.80 (1H, dd, J=13.5 and 4.9 Hz), 2.71 (1H, dd, J=13.1 and 10.7 Hz), 2.54 (1H, d, J=13.5 Hz), 1.90 (3H, d, J=1.4 Hz).

DETD-31 (Method A): ($^1$H-NMR, 400 MHz, CDCl$_3$) σ 8.04-7.99 (2H, m), 7.63-7.58 (1H, m), 7.48 (1H, d, J=8.0 Hz), 7.46 (1H, d, J=7.4 Hz), 6.95 (1H, br s), 6.36 (1H, d, J=3.3 Hz), 5.97 (1H, d, J 2.7 Hz), 5.60 (1H, t, J=10.0 Hz), 5.48-5.44 (1H, m), 4.55 (1H, br d, J=10.0 Hz), 4.26 (1H, ddd, J=10.5, 6.5 and 1.6 Hz), 3.35-3.22 (2H, m), 2.80 (1H, dd, J=13.5 and 4.9 Hz), 2.72 (1H, dd, J=13.3 and 10.7 Hz), 2.53 (1H, d, J=13.3 Hz), 1.92 (3H, d, J=1.4 1-z).

DETD-32 (Method B): ($^1$H-NMR, 400 MHz, CDCl$_3$) σ 7.96 (2H, d, J=8.0 Hz), 6.97-6.92 (3H, m), 6.35 (1H, d, J=2.9 Hz), 5.96 (1H, d, J=2.3 Hz), 5.58 (1H, t, J=10.0 Hz), 5.48-5.43 (1H, m), 4.55 (1H, d, J=10.0 Hz), 4.29 (1H, dd, J=9.4 and 7.1 Hz), 3.31 (1H, d, J=12.7 Hz), 3.28-3.18 (1H, m), 2.80 (1H, dd, J=13.5 and 4.9 Hz), 2.72 (1H, dd, J=12.9 and 10.7 Hz), 2.54 (1H, d, J=13.5 Hz), 1.91 (3H, br s).

DETD-33 (Method B): ($^1$H-NMR, 400 MHz, CDCl$_3$) σ 7.89 (2H, d, J=8.2 Hz), 7.26 (2H, d, J=8.0 Hz), 6.94 (1H, s), 6.35 (1H, d, J=3.1 Hz), 5.96 (1H, d, J=2.7 Hz), 5.58 (1H, t, J=10.0 Hz), 5.49-5.43 (1H, m), 4.55 (1H, d, J=10.0 Hz), 4.29 (1H, ddd, J=10.6, 6.7, and 1.6 Hz), 3.36-3.27 (1H, m), 3.24 (1H, ddd, J=12.8, 6.4, and 3.1 Hz), 2.80 (1H, dd. J=13.6 and 4.8 Hz), 2.72 (1H, dd, J=13.1 and 10.7 Hz), 2.53 (1H, d, J=13.5 Hz), 2.42 (3H, s), 1.91 (3H, d, J=1.4 Hz).

DETD-34 (Method B): ($^1$H-NMR, 400 MHz, CDCl$_3$) σ 7.86 (2H, d, J=8.6 Hz), 7.62 (2H, d, J=8.4 Hz), 6.94 (1H, s), 6.35 (1H, d, J=2.9 Hz), 5.89 (1H, d, J=2.7 Hz), 5.59 (1H, t, J=10.1 Hz), 5.48-5.44 (1H, m), 4.54 (1H, d, J=10.1 Hz), 4.29 (1H, dd, J=9.5 and 6.7 Hz), 3.31 (1H, br d, J=13.5 Hz), 3.28-3.20 (1H, m), 2.81 (1H, dd, J=13.5 and 4.7 Hz), 2.72 (1H, dd, J=13.1 and 10.9 Hz), 2.53 (1H, d, J=13.3 Hz), 1.91 (3H, d, J=1.0 Hz).

DETD-35 (Method A): ($^1$H-NMR, 400 MHz CDCl$_3$) σ 7.91-7.84 (2H, m), 7.81 (1H, d, J=8.0 Hz), 7.51 (1H, d, J=9.6 Hz), 7.53-7.50 (1H, m), 7.44 (1H, t, J=8.0 Hz), 7.37 (1H, d, J=6.4 Hz), 6.85 (1H, s), 5.88 (1H, d, J=3.1 Hz), 5.44-5.38 (1H, m), 5.20 (1H, t, J=10.0 Hz), 5.06 (1H, d, J=2.7 Hz), 4.33 (1H, d, J=10.0 Hz), 4.13-4.00 (1H, m), 4.07 (2H, d, J=10.8 Hz), 3.18 (1H, br d, J=12.9 Hz), 2.93-2.86 (1H, m), 2.77 (1H, dd, J=13.4 and 4.8 Hz), 2.55 (1H, dd, J=12.9 and 10.8 Hz), 2.50 (1H, d, J=13.4 Hz), 1.81 (3H, d, J=1.0 Hz).

DETD-36 (Method B): ($^1$H-NMR, 400 MHz, CDCl$_3$) σ 6.92 (1H, s), 6.44 (1H, d, J=3.1 Hz), 6.04 (1H, d, J=2.7 Hz), 5.49-5.41 (1H, m), 5.31 (1H, t, J=10.0 Hz), 4.46 (1H, d, J=10.0 Hz), 4.24-4.15 (1H, m), 3.26 (1H, br d, J=11.7 Hz), 3.14-3.03 (1H, m), 2.78 (1H, dd, J=13.5 and 4.7 Hz), 2.66 (1H, dd, J=13.1 and 10.7 Hz), 2.54 (1H, d, J=13.5 Hz), 1.81 (3H, d, J=1.4 Hz), 1.64-1.52 (1H, m), 1.05-0.86 (4H, m).

DETD-37 (Method B): ($^1$H-NMR, 400 MHz, CDCl$_3$) σ 6.92 (1H, s), 6.43 (1H, dd, J=3.1 and 0.8 Hz), 6.00 (1H, dd, J=2.7 and 0.8 Hz), 5.46-5.41 (1H, m), 5.24 (1H, t, J=10.0 Hz), 4.42 (1H, d, J=10.0 Hz), 4.18 (1H, ddd, J=10.7, 6.4 and 1.6 Hz), 3.26 (1H, dd, J=13.1 and 2.2 Hz), 3.10-3.02 (1H, m), 2.79 (1H, dd, J=13.5 and 4.9 Hz), 2.74-2.66 (1H, m), 2.65 (1H, dd, J=13.1 and 10.6 Hz), 2.54 (1H, d, J=13.1 Hz), 1.84 (3H, d, J=1.6 Hz), 1.93-1.84 (1H, m), 1.80-1.63 (4H, m), 1.63-1.55 (2H, m).

DETD-38 (Method B): ($^1$H-NMR, 400 MHz, CDCl$_3$) σ 6.91 (1H, s), 6.43 (1H, dd, J=2.9 and 0.8 Hz), 5.98 (1H, dd, J=2.5 and 0.8 Hz), 5.46-5.41 (1H, m), 5.25 (1H, t, J=10.0 Hz), 4.40 (1H, d, J=10.0 Hz), 4.18 (1H, ddd, J=10.7, 6.4 and 1.6 Hz), 3.30-3.22 (1H, m), 3.06 (1H, dd, J=13.1, 6.4 and 3.0 Hz), 2.78 (1H, dd, J=13.5 and 4.7 Hz), 2.65 (1H, dd, J=13.1 and 10.7 Hz), 2.53 (1H, d, J=13.1 Hz), 2.32-2.21 (1H, m), 1.92-1.80 (2H, m), 1.83 (3H, d, J=1.4 Hz), 1.80-1.71 (2H, m), 1.49-1.18 (6H, m).

DETD-39 (Method A): ($^1$H-NMR, 400 MHz, CDCl$_3$) σ 7.66 (1H, d, J=15.9 Hz), 7.32 (1H, t, J=8.0 Hz), 7.11 (1H, d, J=7.8 Hz), 7.05-7.01 (1H, m), 6.96 (1H, dd. J=8.0 and 2.5 Hz), 6.93 (1H, br s), 6.41 (1H, d, J=2.9 Hz), 6.38 (1H, d, J=15.9 Hz), 6.00 (1H, d, J=2.9 Hz), 5.45 (1H, t, J=10.1 Hz), 4.50 (1H, d, J=10.1 Hz), 4.25 (1H, ddd, J=10.5, 6.6 and 1.6 Hz), 3.84 (3H, s), 3.29 (1H, br d, J=13.0 Hz), 3.19-3.11 (1H, m), 2.80 (1H, dd, J=13.3 and 4.9 Hz), 2.69 (1H, dd, J=13.3 and 10.5 Hz), 2.54 (1H, d, J=13.3 Hz), 1.89 (3H, d, J=1.2 Hz).

DETD-40 (Method A): ($^1$H-NMR, 400 MHz, CDCl$_3$) σ 7.70 (1H, d, J=7.8 Hz), 7.58 (1H, d, J=8.4 Hz), 7.56 (1H, s), 7.49 (1H, dd, J=8.4 and 7.8 Hz), 7.34 (1H, t, J=7.8 Hz), 6.95 (1H, s), 6.43 (1H, d, J=3.1 Hz), 6.20 (1H, d, J=2.7 Hz), 5.58 (1H, t, J=10.1 Hz), 5.49-5.44 (1H, m), 4.59 (1H, d, J=10.1 Hz), 4.33-4.24 (1H, m), 3.36-3.24 (2H, m), 2.82 (1H, dd, J=13.5 and 4.9 Hz), 2.72 (1H, dd, J=13.1 and 10.7 Hz), 2.56 (1H, d, J=13.5 Hz), 1.93 (3H, br s).

DETD-41 (Method A): ($^1$H-NMR, 400 MHz, CDCl$_3$) σ 8.07 (1H, s), 7.89 (1H, d, J=7.8 Hz), 7.87 (1H, d, J=7.8 Hz), 7.50 (1H, dt, J=7.8 and 1.2 Hz), 7.42 (1H, dt, J=7.8 and 1.2 Hz), 6.96 (1H, s), 6.43 (1H, d, J=3.1 Hz), 6.14 (1H, d, J=2.5 Hz), 5.56 (1H, t, J=10.0 Hz), 5.49-5.44 (1H, m), 4.58 (1H, d, J=10.0 Hz), 4.27 (1H, ddd, J=10.7, 6.4 and 1.5 Hz), 3.35-3.23 (2H, m), 2.82 (1H, dd, J=13.7 and 4.9 Hz), 2.72 (1H, dd, J=13.1 and 10.7 Hz), 2.56 (1H, d, J=13.5 Hz), 1.92 (3H, d, J=1.4 Hz).

DETD-42 (Method A): ($^1$H-NMR, 400 MHz, CDCl$_3$) σ 7.79 (1H, d, J=15.7 Hz), 7.41 (1H, d, J=5.1 Hz), 7.27 (1H, d, J=5.1 Hz), 7.07 (1H, dd, J=5.1 and 3.7 Hz), 6.93 (1H, br s), 6.41 (1H, d, J=3.1 Hz), 6.18 (1H, d, J=15.7 Hz), 5.99 (1H, t, J=2.7 Hz), 5.45 (1H, t, J=10.0 Hz), 5.47-5.42 (1H, m), 4.48 (1H, d, J=10.0 Hz), 4.24 (1H, dd, J=9.3 and 6.5 Hz), 3.27 (1H, br d, J=13.3 Hz), 3.17-3.08 (1H, m), 2.80 (1H, dd, J=13.5 and 5.0 Hz), 2.69 (1H, dd, J=13.3 and 10.7 Hz), 2.54 (1H, d, J=13.5 Hz), 1.87 (3H, br s).

DETD-43 (Method A): ($^1$H-NMR, 400 MHz, CDCl$_3$) σ 7.36-7.26 (3H, m), 7.24-7.20 (2H, m), 6.90 (1H, br s), 6.18 (1H, d, J=2.9 Hz), 5.47 (1H, t, J=2.4 Hz), 5.44-5.40 (1H, m), 5.24 (1H, t, J=10.0 Hz), 4.40 (1H, d, J=10.0 Hz), 4.14 (1H, ddd, J=10.6, 6.3 and 1.6 Hz), 3.65 (1H, d, J=15.2 Hz), 3.60 (1H, d, J=15.2 Hz), 3.23 (1H, br d, J=13.1 Hz), 3.01 (1H, ddd, J=12.8, 6.3 and 3.0 Hz), 2.78 (1H, dd, J=13.5 and 4.9 Hz), 2.62 (1H, dd, J=13.1 and 10.7 Hz), 2.52 (1H, d, J=13.5 Hz), 1.83 (3H, d, J=1.5 Hz).

DETD-44 (Method A): ($^1$H-NMR, 400 MHz, CDCl$_3$) σ 7.13 (2H, d, J=8.5 Hz), 6.90 (1H, br s), 6.86 (2H, d, J=8.5 Hz), 6.22 (2H, d, J=3.1 Hz), 5.53 (1H, t, J=2.4 Hz), 5.43 (1H, t, J=2.4 Hz), 5.46-5.41 (1H, m), 5.24 (1H, t, J=10.0 Hz), 4.40 (1H, d, J=10.0 Hz), 4.18-4.11 (1H, m), 3.80 (3H, s), 3.58 (1H, d, J=15.4 Hz), 3.53 (1H, d, J=15.4 Hz), 3.23 (1H, br d, J=13.1 Hz), 3.02 (1H, ddd, J=12.6, 6.3 and 3.1 Hz), 2.77 (1H, dd, J=13.4 and 4.8 Hz), 2.63 (1H, dd, J=13.1 and 10.7 Hz), 2.52 (1H, d, J=13.4 Hz), 1.82 (3H, br s).

DETD-45 (Method A): ($^1$H-NMR, 400 MHz, CDCl$_3$) σ 7.78 (1H, d, J=10.2 Hz), 7.70 (1H, d, J 8.0 Hz), 7.39 (1H, t, J=8.0 Hz), 7.21 (1H, d, J=7.0 Hz), 7.20-7.15 (2H, m), 6.86 (1H, br s), 5.90 (1H, d, J=2.8 Hz), 5.44-5.39 (1H, m), 5.19 (1H, t, J=10.0 Hz), 5.04 (1H, d, J=2.8 Hz), 4.33 (1H, d, J=10.0 Hz), 4.15-3.99 (3H, m), 3.93 (3H, s), 3.18 (1H, br d J=12.5 Hz), 2.94-2.85 (1H, m), 2.77 (1H, dd, J=13.5 and 4.8 Hz), 2.62-2.46 (2H, m), 1.81 (3H, br s).

DETD-46 (Method A): ($^1$H-NMR, 400 MHz, CDCl$_3$) σ 7.71 (1H, d, =8.4 Hz), 7.68 (1H, d, J=9.1 Hz), 7.60 (1H, br s), 7.29 (1H, d, J=8.4 Hz), 7.18-7.10 (2H, m), 6.89 (1H, br s), 6.09 (1H, d, J=3.1 Hz), 5.46 (1H, d, J=2.5 Hz), 5.45-5.40 (1H, m), 5.26 (1H, t, J=10.0 Hz), 4.40 (1H, d, J=10.0 Hz), 4.14 (1H, dd, J=10.0 and 6.4 Hz), 3.92 (3H, s), 3.77 (1H, d, J=15.1 Hz), 3.72 (1H, d, J=15.1 Hz), 3.22 (1H, d, J=13.1 Hz), 3.05-2.95 (1H, m), 2.77 (1H, dd, J=13.3 and 4.8 Hz), 2.60 (1H, dd, J=13.1 and 10.8 Hz), 2.51 (1H, d, J=13.3 Hz), 1.83 (3H, br s).

DETD-47 (Method A): ($^1$H-NMR, 400 MHz, CDCl$_3$) σ 7.67 (1H, d, J=16.0 Hz), 7.48-7.42 (2H, m), 7.36 (1H, s), 7.30-7.25 (1H, m), 6.96 (1H, s), 6.42 (1H, d, J=16.0 Hz), 6.42 (1H, d, J=2.5 Hz), 5.99 (1H, d, J=2.5 Hz), 5.49 (1H, t, J=10.11 Hz), 5.47-5.48 (1H, m), 4.51 (1H, d, J=10.8 Hz), 4.25 (1H, dd, J=10.5 and 6.7 Hz), 3.28 (1H, d, J=13.1 Hz), 3.18-3.14 (1H, m), 2.81 (1H, dd, J=13.7 and 4.8 Hz), 2.71 (1H, dd, J=13.1 and 10.5 Hz), 2.56 (1H, d, J=13.7 Hz), 1.90 (3H, s).

DETD-48 (Method A): ($^1$H-NMR, 400 MHz, CDCl$_3$) σ 7.77 (1H, s), 7.72 (1H, d J=16.2 Hz), 7.66 (1H, d, J=7.8 Hz), 7.54 (1H, t, J=7.8 Hz), 6.95 (1H, s), 6.47 (1H, d, J=16.2 Hz), 6.43 (1H, d, J=2.8 Hz), 6.00 (1H, d, J=2.8 Hz), 5.48 (1H, t, J=10.0 Hz), 5.48-5.45 (1H, m), 4.51 (1H, d, J=10.0 Hz), 4.26 (1H, ddd, J=10.5, 6.8 and 2.0 Hz), 3.30 (1H, dd, J=13.2 and 2.0 Hz), 3.19-3.12 (1H, m), 2.82 (1H, dd, J=13.7 and 4.8 i-z), 2.70 (1H, dd, J=13.2 and 10.5 Hz), 2.55 (1H, d, J=13.3 Hz), 1.89 (3H, d, J=1.4 Hz).

DETD-49 (Method A): ($^1$H-NMR, 400 MHz, CDCl$_3$) σ 7.64 (1H, d, J=15.6 Hz), 7.11 (1H, dd, J=8.3 and 1.8 Hz), 7.03 (1H, d, J=1.8 Hz), 6.94 (1H, s), 6.88 (1H, d, J=8.3 Hz), 6.42 (1H, d, J=2.6 Hz), 6.26 (1H, d, J=15.6 Hz), 6.02 (1H, d, J=2.6 Hz), 5.48 (1H, t, J=10.1 Hz), 5.48-5.45 (1H, m), 4.50 (1H, d, J=10.1 Hz), 4.26 (1H, ddd, J=10.5, 6.6 and 1.8 Hz), 3.93 (3H, s), 3.92 (3H, s), J=1.3 Hz), 3.29 (1H, dd, J=13.3 and 1.8 Hz), 3.18-3.10 (1H, m), 2.81 (1H, dd, J=13.3 and 5.0 Hz), 2.70 (1H, dd, J=13.3 and 10.5 Hz), 2.54 (1H, d, J=13.3 Hz), 1.89 (3H, d, J=1.4 Hz).

DETD-50 (Method A): ($^1$H-NMR, 400 MHz, CDCl$_3$) σ 7.66 (1H, d, J=16.0 Hz), 7.30 (1H, t, J=7.7 Hz), 7.10 (1H, d, J=7.7 Hz), 7.04-7.02 (1H, m), 6.97-6.93 (1H, m), 6.94 (1H, s), 6.42 (1H, d, J=3.0 Hz), 6.37 (1H, d, J=16.0 Hz), 6.00 (1H, d, J=3.0 Hz), 5.46 (1H, t, J=10.1 Hz), 5.45-5.44 (1H, m), 4.50 (1H, d, J=10.1 Hz), 4.25 (1H, ddd, J=10.8, 6.8 and 1.4 Hz), 4.06 (2H, q, J=7.0 Hz), 3.29 (1H, dd, J=13.3 and 2.1 Hz), 3.15 (1H, ddd, 12.8, 6.9 and 3.5 Hz), 2.81 (1H, dd, J=13.3 and 4.8 Hz), 2.70 (1H, dd, J=13.3 and 10.8 Hz), 2.55 (1H, d, J=13.3 Hz), 1.89 (3H, d, J=1.4 Hz), 1.43 (3H, t, J=7.0 Hz).

DETD-51 (Method A): ($^1$H-NMR, 400 MHz, CDCl$_3$) σ 7.98 (1H, d, J=7.8 Hz), 7.90-7.85 (1H, m), 7.75 (1H, d, J=7.8 Hz), 7.54 (1H, dt, J=6.8 and 1.3 Hz), 7.50 (1H, dt. J=6.8 and 1.3 Hz), 7.38 (1H, t. J=6.8 Hz), 7.31 (1H, d, J=6.8 Hz), 6.87 (1H, s), 6.19 (1H, d, J=2.8 Hz), 5.65 (1H, d, J=2.8 Hz), 5.43 (1H, dd, J=4.6 and 1.8 Hz), 5.26 (1H, t. J=10.1 Hz), 4.30 (1H, d, =10.1 Hz), 4.15 (1H, ddd, J=10.5, 6.4 and 1.4 Hz), 3.40 (2H, t, J=7.8 Hz), 3.26-3.19 (1H, m), 2.98-2.92 (1H, m), 2.82-2.73 (3H, m), 2.61 (1H, dd, J=13.3 and 10.8 Hz), 2.50 (1H, d, J=13.8 Hz), 1.85 (3H, d, =1.4 Hz).

DETD-52 (Method A): ($^1$H-NMR, 400 MHz, CDCl$_3$) σ 8.84 (1H, dd, J=4.1 and 1.8 Hz), 8.16 (1H, dd, J=8.3 and 1.4 Hz), 7.79 (1H, dd, J=8.3 and 1.4 Hz), 7.62 (1H, d, J=6.7 Hz), 7.51 (1H, dd, J=8.3 and 6.7 Hz), 7.42 (1H, dd, J=8.3 and 4.1 Hz), 6.89 (1H, br s), 6.25 (1H, d, J=2.7 Hz), 5.95 (1H, d, J=2.7 Hz), 5.43 (1H, dd, J=4.8 and 2.1 Hz), 5.28 (1H, t, J=10.1 Hz), 4.43 (1H, d, J=10.1 Hz), 4.36 (1H, d, J=15.6 Hz), 4.17 (1H, ddd, J=10.8, 6.7 and 1.5 Hz), 4.10 (1H, d, J=15.6 Hz), 3.24 (1H, dd, J=13.1 and 2.1 Hz), 3.04 (1H, ddd, J=13.1, 6.7 and 3.3 Hz), 2.78 (1H, dd, J=13.2 and 4.8 Hz), 2.63 (1H, dd, J=13.1 and 10.8 Hz), 2.53 (1H, d, J=13.2 Hz), 1.80 (3H, d, J=1.4 Hz).

DETD-53 (Method A): ($^1$H-NMR, 400 MHz, CDCl$_3$) σ 7.70 (1H, d, J=8.7 Hz), 7.69 (1H, d, J=8.7 Hz), 7.57 (1H, br s), 7.29 (1H, dd, J=8.7 and 1.8 Hz), 7.16 (1H, dd, J=8.7 and 2.5 Hz), 7.12 (1H, d, J=2.3 Hz), 6.80 (1H, br s), 6.26 (1H, d, J=2.8 Hz), 5.69 (1H, d, J=2.5 Hz), 5.40-5.35 (1H, m), 5.23 (1H, t. J=10.0 Hz), 4.21 (1H, d, J=10.0 Hz), 4.18-4.11 (1H, m), 3.94 (3H, s), 3.84 (1H, q, J=7.0 Hz), 3.21 (1H, br d, J=13.3 Hz), 2.95 (1H, ddd, J=13.3, 6.5 and 3.1 Hz), 2.75 (1H, dd, J=13.7 and 4.6 Hz), 2.57 (1H, dd, J=13.3 and 10.7 Hz), 2.41 (1H, d, J=13.3 Hz), 1.85 (3H, d, J=1.4 Hz), 1.55 (3H, d, J=7.0 Hz).

DETD-54 (Method A): ($^1$H-NMR, 400 MHz, CDCl$_3$) σ 7.71 (1H, d, J=8.3 Hz), 7.68 (1H, d, J=9.0 Hz), 7.61 (1H, br s), 7.31-7.26 (1H, m), 7.16 (1H, dd, J=9.0 and 2.3 Hz), 7.12 (1H, d, J=2.3 Hz), 6.80 (1H, br s), 5.56 (1H, d, J=2.7 Hz), 5.47-5.42 (1H, m), 5.20 (1H, t, J=10.1 Hz), 4.78 (1H, d, J=2.7 Hz), 4.41 (1H, d, J=10.1 Hz), 4.12-4.05 (1H, m), 3.94 (3H, s), 3.77 (1H, q, J=7.0 Hz), 3.24-3.16 (1H, m), 2.94 (1H, ddd, J=12.8, 6.1 and 3.1 Hz), 2.81 (1H, dd, J=13.3 and 4.6 Hz), 2.63-2.52 (2H, m), 1.86 (3H, d, J=1.4 Hz), 1.54 (3H, d, J=7.0 Hz).

DETD-55 (Method A): ($^1$H-NMR, 400 MHz. CDCl$_3$) σ 8.25 and 8.02 (1H, d, J=8.7 Hz, 3:5), 7.90-7.82 (3H, m), 7.68 and 7.64 (1H, d, J=6.9 Hz, 5:3), 7.54-7.36 (6H, m), 6.81 and 6.70 (1H, br s, 3:5), 6.01 (5/8H, d, J=2.7 Hz), 5.43-5.25 (27/8H, m), 5.13 and 5.11 (1H, t, J=10.1 Hz, 3:5), 4.30 (3/8H, d, J=2.7 Hz), 4.26-4.20 (5/8H, m), 4.09-4.01 (1H, m), 3.91 (5/8H, d, J=10.1 Hz), 3.17-3.12 (3/8H, m), 3.11 and 3.08 (3H, s, 5:3), 2.84-2.68 (2H, m), 2.54-2.25 (2H, m), 1.95 and 1.92 (3H, s, 5:3), 1.85 and 1.83 (3H, d, J=1.4 Hz, 3:5).

DETD-56 (Method A): ($^1$H-NMR, 400 MHz, CDCl$_3$) σ 7.87-7.80 (4H, m), 7.55-7.49 (2H, m), 7.42 (1H, dd, J=8.5 and 1.4 Hz), 6.81 (1H, br s), 6.22 (1H, d, J=3.2 Hz), 5.78 (1H, d, J=2.7 Hz), 5.40-5.35 (1H, m), 5.28 (1H, t, J=10.1 Hz), 4.92 (1H, s), 4.24 (1H, d, J=10.1 Hz), 4.17-4.10 (1H, m), 3.43 (3H, s), 3.20 (1H, dd, J=13.3 and 1.8 Hz), 3.03 (1H, ddd, J=12.9, 6.5 and 3.2 Hz), 2.72 (1H, dd, J=13.3 and 4.7 Hz), 2.58 (1H, dd, J=12.9 and 10.8 Hz), 2.38 (1H, d, J=13.3 Hz), 1.81 (1H, d, J=1.4 Hz).

DETD-57 (Method A): ($^1$H-NMR, 400 MHz, CDCl$_3$) σ 7.90-7.81 (4H, m), 7.58-7.50 (2H, m), 7.46 (1H, dd, J=8.5 and 1.6 Hz), 6.87 (1H, br s), 5.70 (1H, d, J=3.2 Hz), 5.45-5.40 (1H, m), 5.27 (1H, t, J=10.1 Hz), 5.03 (1H, d, J=2.3 Hz), 4.86 (1H, s), 4.36 (1H, d, J=10.1 Hz), 4.15-4.07 (1H, m), 3.37 (3H, s), 3.20 (1H, br d, J=12.8 Hz), 3.03-2.95 (1H, m), 2.76 (1H, dd, J=13.3 and 4.8 Hz), 2.59 (1H, dd, J=12.8 and 10.8 Hz), 2.48 (1H, d, J=13.3 Hz), 1.84 (1H, d, J=1.4 Hz).

DETD-58 (Method A): ($^1$H-NMR, 400 MHz, CDCl$_3$) σ 7.90-7.85 (1H, m), 7.68-7.64 (1H, m), 7.44-7.36 (2H, m), 7.32 (1H, s), 6.89 (1H, br s), 6.07 (1H, d, J=2.7 Hz), 5.45-5.41 (1H, m), 5.37 (1H, d, J=2.3 Hz), 5.26 (1H, t, J=10.1 Hz), 4.37 (1H, d, J=10.1 Hz), 4.16-4.08 (1H, m), 3.88 (2H, s), 3.24-3.17 (1H, m), 2.97 (1H, ddd, J=13.0, 6.0 and 3.2 Hz), 2.78 (1H, dd, J=13.3 and 4.7 Hz), 2.60 (1H, d, J=13.0 Hz), 2.51 (1H, d, J=13.3 Hz), 1.84 (1H, d, J=1.4 Hz).

DETD-59 (Method A): ($^1$H-NMR, 400 MHz, CDCl$_3$) σ 7.59 (1H, s), 7.47 (2H, t. J=8.7 Hz), 7.34-7.28 (1H, m), 7.25 (1H, m), 6.90 (1H, br s), 6.22 (1H, d, J=3.2 Hz), 5.65 (1H, d, J=2.3 Hz), 5.45-5.41 (1H, m), 5.30 (1H, t. J=10.1 Hz), 4.39 (1H, d, J=10.1 Hz), 4.20-4.09 (1H, m), 3.70 (2H, s), 3.22 (1H, br d, J=12.8 Hz), 3.02 (1H, ddd, J=12.8, 6.4 and 3.2 Hz), 2.79 (1H, dd, J=13.3 and 4.7 Hz), 2.63 (1H, dd, J=13.3 and 10.7 Hz), 2.51 (1H, d, J=13.3 Hz), 1.84 (1H, d, =1.4 Hz).

DETD-60 (Method A): ($^1$H-NMR, 400 MHz, CDCl$_3$) σ 7.65 (1H, d, J=15.6 Hz), 7.46 (2H, d, J=8.7 Hz), 6.94 (1H, br s), 6.89 (2H, d, J=8.7 Hz), 6.41 (1H, d, J=2.5 Hz), 6.25 (1H, d, J=15.6 Hz), 6.01 (1H, d, J=2.5 Hz), 5.46 (1H, t, J=10.1 Hz), 5.48-5.42 (1H, m), 4.50 (1H, d, J=9.6 and 6.5 Hz), 4.07 (2H, q, J=6.9 Hz), 3.28 (1H, br d, J=11.9 z), 3.19-3.10 (1H, m), 2.80 (1H, dd, J=13.3 and 5.0 Hz), 2.69 (1H, dd, J=13.3 and 10.3 Hz), 2.54 (1H, d, J=13.3 Hz), 1.89 (1H, br s), 1.43 (3H, t, J=6.9 Hz).

DETD-61 (Method A): ($^1$H-NMR, 400 MHz, CDCl$_3$) σ 7.60 (1H, d, J=16.0 Hz), 7.06-6.97 (2H, m), 6.94 (1H, br s), 6.82 (1H, d, J=7.7 Hz), 6.41 (1H, d, J=3.2 Hz), 6.21 (1H, d, J=16.0 Hz), 6.02 (2H, s), 6.00 (1H, d, J=2.7 Hz), 5.45 (1H, t, J=10.1 Hz), 5.49-5.43 (1H, m), 4.50 (1H, d, J=10.1 Hz), 4.28-4.22 (1H, m), 3.28 (1H, br d, J=11.6 Hz), 3.02 (1H, ddd, J=13.0, 6.4 and 3.2 Hz), 2.80 (1H, dd, J=13.3 and 4.8 Hz), 2.69 (1H, dd, J=13.0 and 10.7 Hz), 2.54 (1H, d, J=13.3 Hz), 1.88 (1H, d, J=1.4 Hz).

DETD-62 (Method C): ($^1$H-NMR, 400 MHz, CDCl$_3$) σ 7.96-7.91 (1H, m), 7.91-7.85 (1H, m), 7.80 (1H, d, J=8.3 Hz), 7.57-7.47 (2H, m), 7.43 (1H, dd, J=8.3 and 6.9 Hz), 7.37 (1H, d, J=6.9 Hz), 7.03 (1H, br s), 6.20 (1H, d, J=3.4 Hz), 5.84 (1H, d, J=16.0 Hz), 5.45 (1H, d, J=3.4 Hz), 5.27 (1H, dd, J=16.0 and 9.6 Hz), 5.24-5.17 (1H, m), 4.44-4.35 (1H, m), 3.99 (2H, s), 3.57-3.48 (1H, m), 3.21 (1H, br d, J=13.0 Hz), 2.83 (1H, t, J=12.2 Hz), 2.56 (1H, dd, J=14.6 and 6.4 Hz), 2.32 (1H, d, J=14.6 Hz), 2.51 (1H, d, J=13.0 Hz), 1.71 (1H, s).

All of the side-chain structures of synthetic DETD-3 to DETD-61 and the structure of DETD-62 are summarized and listed in Tables 2 and 6.

TABLE 2-continued
| No | R |
|----|---|
| 22 | 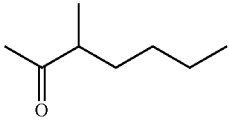 |
| 23 | 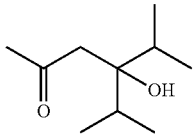 |
| 24 | 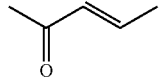 |
| 25 | 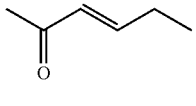 |
| 26 | 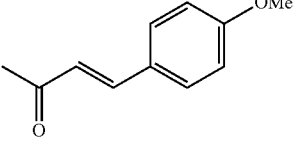 |
| 27 | 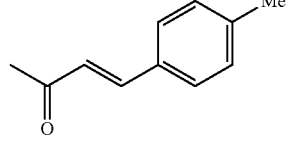 |
| 28 | 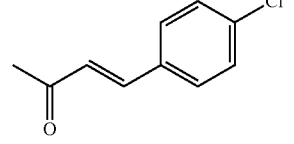 |
| 29 | 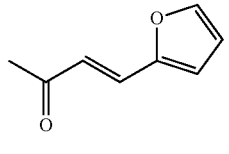 |
| 30 | 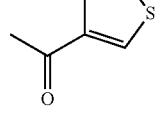 |
| 31 | 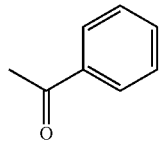 |
| 32 | 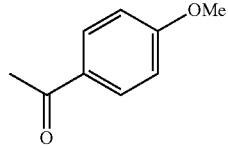 |
| 33 | 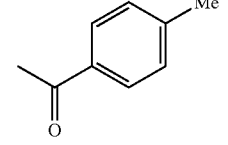 |
| 34 | 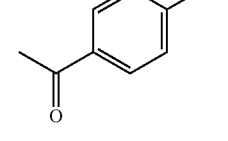 |
| 35 | 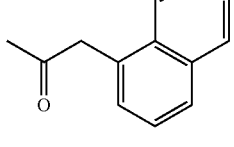 |
| 36 | 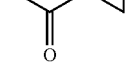 |
| 37 | 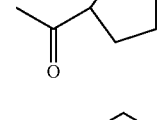 |
| 38 | 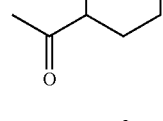 |
| 39 | 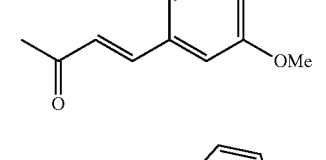 |
| 40 | 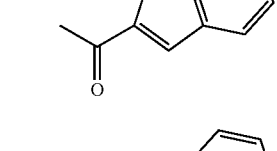 |
| 41 | 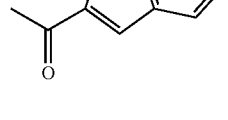 |

TABLE 2-continued
| No | R |
|---|---|
| 42 | 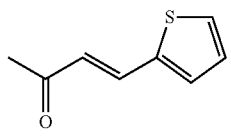 |
| 43 | 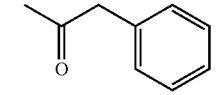 |
| 44 | 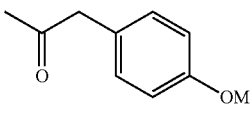 |
| 45 | 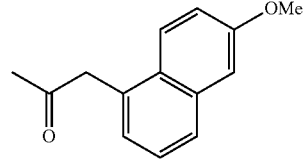 |
| 46 | 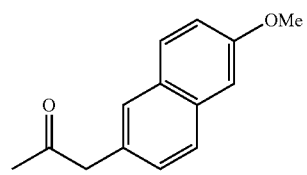 |
| 47 | 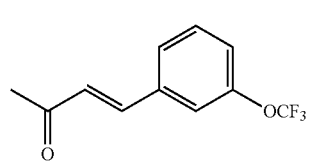 |
| 48 | 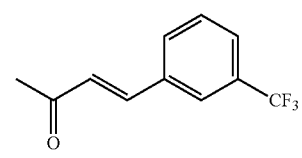 |
| 49 | 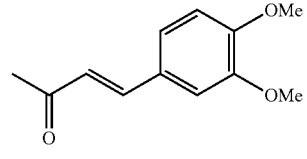 |
| 50 | 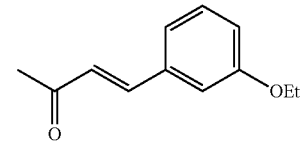 |
| 51 | 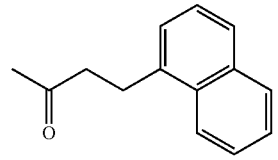 |
| 52 | 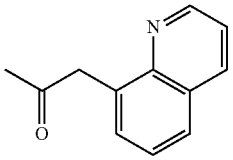 |
| 53 | 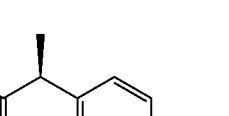 |
| 54 | 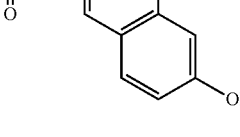 |
| 55 | 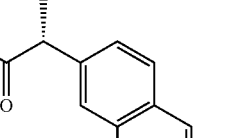 |
| 56 | 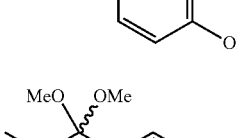 |
| 57 | 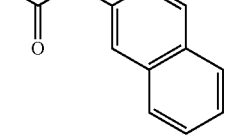 |
| 58 | 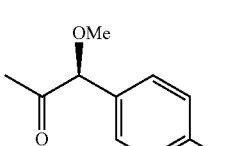 |
| 59 | 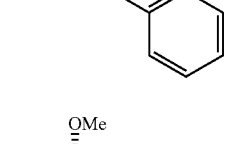 |

TABLE 2-continued

| No | R |
|---|---|
| 60 | (structure: 4-ethoxyphenyl α,β-unsaturated ketone) |
| 61 | (structure: 3,4-methylenedioxyphenyl α,β-unsaturated ketone) |
| 62 | (complex macrocyclic structure with naphthylacetate ester) |

Cell Culture

The murine macrophage RAW 264.7, human normal epithelial cell line M10 and melanocyte, melanoma cell lines including mouse B16-F10 (N-RAS mutation), human MeWo (wild-type for both B-RAF and N-RAS), human A375 and A2058 (B-RAF$^{V600E}$ mutation), and human SK-Mel-2 (N-RAS mutation), breast cancer cell lines including mouse TS/A (ER+), human MDA-MB-231 (ER−, Her2−, PR−), human MCF-7 (ER+, Her2−), human SKBR3 (ER−□, Her2+), human BT474 (ER+, Her2+), brain cancer cell line U-87MG, colon cancer cell line HCT-116, kidney cancer cell line A498, Lung cancer cell line PC6, lymphoma line U937, neuroepithelioma line SK-N-MC, stomach cancer cell line KATO III and uterus cancer cell line NES-SA obtained from the ATCC (Manassas, Va.) were grown in manufactures' suggested medium supplemented with 10% heat-inactivated fetal bovine serum, 100 units/mL penicillin, and 100 µg/mL streptomycin, at 37° C. in a humidified 5% $CO_2$ incubator.

A375-R, acquired vemurafenib resistance melanoma cell was generated from A375 parental cell and grown in same conditions as A375 cell.

Cell Viability Assay

Normal or cancer cells ($2\times10^3$ to $1\times10^4$ cells/well) were seeded in 96-well plate for overnight and treated with different compounds for 24 h to 72 h. Cells growth were determined by MTT-based colorimetric assays according to. Viability of the test cells treated with vehicle (0.5% DMSO) only was defined as 100% viable. Survival of cells after treatment with DETDs was calculated using the following formula: viable cell number (%)=$OD_{570}$ (treated cell culture)/$OD_{570}$ (vehicle control)×100.

Boyden Chamber Assay

To test the anti-migratory and anti-invasive effect of DET. DETD-35 and PTX. Boyden chambers assay was carried out. The lower well of the chamber (6.5 mm diameter, 8 mm pore size; Costar. Cambridge, Mass., USA) was added 10% fetal bovine serum (FBS) as a chemoattractant and filled with DMEM culture medium containing vehicle (DMSO, 0.05%), DET (2.5 and 4 µM). DETD-35 (1.25 and 2.5 µM), or PTX (2.5 and 4 µM). MDA-MB-231 cells were placed into the upper chamber ($5\times10^4$ cells per insert) with the medium containing 0.1% FBS. After 24 h incubation at 37° C. in a 5% $CO_2$ atmosphere, non-migrating cells were scraped from the upper surface of the membrane using a cotton swab, and the migrated cells remaining in the well were fixed and stained with DAPI solution (4,6-diamidino-2-phenylindole, 1 µg/ml). The migrating cells were counted in three fields at 20× original magnifications by inverted fluorescence microscopy. To test the anti-invasive effect of the compounds, 8-µm filters were pre-coating with Matrigel (30 µg per filter) and incubated at 37° C. for 2 h, then followed the protocol of migration assay descried about.

Compound-Drug Combination Assay

Synergistic effects between DETDs and PLX4032 or between DETDs and PTX were determined with a range of indicated concentrations of DETDs and PLX4032 or DETDs and PTX. Briefly, cells ($1.5\times10^3$ to $5\times10^3$ cells/well) were seeded in 96-well plates and treated with compounds or drugs alone or in combination for 24 h to 72 h. Cell proliferation was measured by MTT assay. Isobologram analysis and Chou-Talalay method was used to determine the effects of compound drug combinations. The interaction of DETDs and PLX4032 or PTX was determined by the combination index (CI), and the CI plot was generated using CompuSyn software. The combined effects of two compounds can be categorized as follows: CI=1 indicates additive interaction, CI<1 indicates synergism, and CI>1 indicates antagonism.

Time-Lapse Microscope Analysis

A 12 well cell culture plate was coated with 25 µg/mL fibronectin for 1 h and then seeded with $5\times10^4$ MDA-MB-231 cells in DMEM containing 10% serum. Twelve hours after seeding, time-lapse microscopy experiments were performed on an Inverted Confocal Microscope (LSM 510 META) equipped with an environmental chamber with phase-contrast optics (images taken every 30 min). Using the object-tracking application of Metamorph software (Molecular Devices), an average of 12 subsequent cell centroid displacements/30 min between two consecutive images were evaluated as cell velocities of migration. In total, cell trajectories were recorded for 24 h. These assays were made in treatments with vehicle (DMSO, 0.05%), DET (2.5, 4 and 10 µM), and DETD-35 (1.25, 2.5, 4 µM) added at the beginning of the time-lapse imaging/video taping.

Western Blot Analysis

Total cellular proteins were prepared from test cells as previously described. Protein concentration was determined by the Bradford method (Bio-Rad). Protein samples were resolved by 5% to 20% gradient SDS-PAGE and then underwent immunoblotting. Primary antibodies against ERK1/2 and GAPDH were from Santa Cruz Biotechnology (Santa Cruz, Calif., USA) and MEK, phospho-ERK1/2 and phospho-MEK were from Cell Signaling Technology (Danvers, Mass., USA). Appropriate horseradish peroxidase-conjugated secondary antibodies were used. Protein bands reacting to specific antibody were visualized by use of enhanced chemiluminescence (Amersham) with exposure to chemiluminescence light film (BioMax; Kodak Co.).

Measurement of Nitric Oxide (NO) Production

Marcophages ($2\times10^5$ cells/well in 96-well plate) were treated with compounds for 1 h, then incubated further for 24 h with or without the presence of 100 ng/μL LPS in the cultural medium. Nitrite levels in cell culture medium were determined by the Griess reaction method. In parallel to the Griess assays, macrophage cell viabilities were determined using the MTT based colorimetric assay.

Synergism of Gluthathione Biosynthesis Blockers with DET and DETD-35 Against Cancer Cell Proliferation Synergistic effects of gluthathione biosynthesis blockers, buthionine sulfoximine (BSO) and sulfasalazine, and DET or DETD-35 were determined. Briefly, cells ($5 \times 10^3$ cells/well) were seeded in 96-well plates and treated with BSO at concentrations 100 μM, 45 μM, 18 μM, 7.2 μM, 2.8 μM, 1.15 μM, 461 nM, 184 nM, 74 nM and 29 nM, and sulfasalazine at concentrations 62.75 μM, 25.10 μM, 10 μM, 4 μM, 1.6 μM, 642 nM, 257 nM, 102 nM, 41 nM and 16.4 nM for 30 h, and then 12 μM DET or 3 μM DETD-35 were added in the cultural medium to treat the cells for another 24 h. Cell proliferation was measured by MIT assay.

Animals

Female NOD/SCID mice (NOD.CB17-Prkdcscid/IcrCrl-Bltw) and SCID mice (CB17-Prkdcscid/IcrCrlBltw) were supplied from the Laboratory Animal Core Facility (Bio-LASCO Taiwan Co., Ltd) and given a standard laboratory diet and distilled $H_2O$ ad libitum and kept on a 12 h light/dark cycle at 22±2° C. All experimental protocols were approved by the Institutional Animal Care and Utilization Committee (IACUC), Academia Sinica, Taiwan, R.O.C.

Inhibition of Mammary Tumor Growth in NOD/SCID Mice

Mammary tumor response to DET analog (DETD-35) was studied using MDA-MB-231 cancer cell bearing NOD/SCID mice (6 weeks old). The mammary fat pad regions of mice were injected with $5 \times 10^6$ MDA-MB-231 cells in 100 μL (9.1 mg/mL) matrigel (Basement Membrane Matrix. Phenol Red-free) on day 0. Tumors were allowed to grow in the mice for 7 days, and then the animals were randomly assigned to three groups (n=5 per group): sham, tumor (vehicle) control and 10 mg/kg DETD-35 treatment group. DETD-35 was intraperitoneally (i.v.) injected every three days. The test mice were sacrificed by cervical dislocation at day 71, and the tumor were collected and measured for the volume (V) using calipers and calculated by the formula $V = (L \times W^2)/2$, where L is the length and W is the width of tumor.

Inhibition of Lung Metastasis of MDA-MB-231 Cells in SCID Mice

Female SCID mice (5 weeks old, average body weight 19.59±1.26 g) were assigned to 8 groups: PIX group (5 mg/kg paclitaxel), DETD-35-2 group (2 mg/kg DETD-35), DETD-35-10 group (10 mg/kg DETD-35). PTX-5+DETD-35-2 group (5 mg/kg paclitaxel and 2 mg/kg DETD-35 administration alternatively for eleven doses of paclitaxel (PTX) and ten doses of DETD-35 in total), tumor (vehicle) group (5% DMSO), and sham group (5% DMSO). Pre-DETD-35-10 group was the mice administered 10 mg/kg DETD-35 every two days for three doses before the i.v. injection of $1 \times 10^6$ MDA-MB-231 tumor cells at day 0. All other drug or compounds were administered i.p. every three days starting from day 1. At the end of experiment (day 71), the test mice were sacrificed by cervical dislocation. The lung, liver, kidney, and spleen organs were removed and recorded weights and calculated for organ index (% of organ weight/body weight). The number of tumor colonies on lungs of test mice was counted.

In Vivo Melanoma Xenograft Model

A375 and A375-R melanoma cells ($3 \times 10^6$) were injected subcutaneously to the flanks of the six weeks old NOD/SCID mice. One week after the inoculation, the mice were randomized into treated groups (n=8 per group) and the treatments were started. Body weight and tumor volume of the mice were recorded every three days using formula $a \times b^2 \times 0.5$, where a and b represented the larger and smaller tumor diameters.

Two-Stage Skin Carcinogenesis Model

Dorsal skin of six weeks old female FVB/N mice were shaved and treated with topical application of DMBA (25 μg in 100 μL acetone). One week after DMBA treatment, the same skin area were treated topically twice weekly with 12-O-tetradecanoylphorbol-13-acetate (TPA) (4 μg in 100 μL acetone). The area was regularly shaved and tumor formation was assessed twice weekly, and tumors were defined as raised lesions of a minimum diameter of 1 mm.

Results

Inhibitory Effect of DET and Newly Synthesized DETDs Against Breast Cancer Cell Proliferation Sixty DETDs were derived from parental compound DIET and tested for anti-breast cancer cell activity. Table 3 shows the $IC_{50}$ values (inhibition of 50% cell proliferation) of DET and DETDs analyzed by MIT assay[a] in 24-h treatment against proliferation of murine mammary cancer cells TS/A (ER+, Her2−), human breast cancer cells MCF-7 (ER+, Her2−), MDA-MB-231 (ER−, Her2−, PR−), and normal mammary cells M10, respectively. The $IC_{50}$ of DET for TS/A and MCF-7 cells were determined at 2.3 and 5.0 μM respectively, and a much less effect was observed for MDA-MB-231 cell with $IC_{50}$=14.0 μM. Among the 60 DETDs tested, the top three DETDs with a better activity than DET on 50% inhibition of proliferation of TS/A cells, MCF-7 cells, and MDA-MB-231 cells were DETD-39 (0.8 μM), -26 (1.5 μM), and -35 (1.7 μM), DETD-6 (1.6 μM), -39 (2.1 μM), and -7 (2.3 μM), and DETD-39 (1.9 μM), -34 (2.2 μM), and -35 (3.5 μM), respectively. DETD-6, -26 and -39 also showed some toxicity to normal mammary epithelial M10 cells.

TABLE 3

| Compounds | TS/A (ER+, Her2−) | MDA-MB-231 (ER−, PR−, Her2−) | MCF-7 (ER+, Her2−) | M10 (normal) |
|---|---|---|---|---|
| DET | 2.3 | 14 | 5 | — |
| DETD-1 | 6.2 | — | — | — |
| DETD-3 | 7.5 | — | — | — |
| DETD-4 | 1.8 | 6.2 | 3.4 | — |
| DETD-5 | 1.6 | 4.6 | 2.4 | — |
| DETD-6 | 1.6 | 4.2 | 1.6 | 4.9 |
| DETD-7 | 1.8 | 6.1 | 2.3 | — |
| DETD-8 | 1.9 | 6.7 | 3.4 | — |
| DETD-9 | — | — | — | — |
| DETD-10 | 2.7 | 5.9 | 3.4 | — |
| DETD-11 | 2.9 | — | 4.2 | — |
| DETD-12 | 3.3 | 7.0 | 4.2 | — |
| DETD-13 | 1.9 | 7.5 | 3.7 | — |
| DETD-14 | — | — | — | — |
| DETD-16 | 2.1 | 7.0 | 3.9 | — |
| DETD-17 | 3.5 | — | 6.7 | — |
| DETD-18 | 3.3 | 5.5 | 2.6 | — |
| DETD-19 | 1.7 | 4.6 | 3.5 | — |
| DETD-20 | 2.2 | 5.8 | 3.5 | — |
| DETD-21 | 4.0 | — | 4.5 | — |
| DEED-22 | 1.8 | 4.3 | 2.5 | 4.7 |
| DETD-23 | 2.4 | 5.9 | 2.5 | — |
| DETD-24 | 2.3 | — | 3.9 | — |
| DETD-25 | 4.0 | — | 5.8 | — |
| DETD-26 | 1.5 | 4.1 | 3.7 | 4.7 |
| DETD-27 | 2.4 | 3.6 | 3.7 | — |
| DETD-28 | 1.8 | 4.2 | 3.6 | 4.8 |
| DETD-29 | 2.2 | 4.9 | 4.1 | — |
| DETD-30 | 2.4 | 4.3 | 3.7 | — |
| DETD-31 | 2.0 | 4.5 | 5.9 | — |

TABLE 3-continued

| Compounds | TS/A (ER+, Her2−) | MDA-MB-231 (ER−, PR−, Her2−) | MCF-7 (ER+, Her2−) | M10 (normal) |
|---|---|---|---|---|
| DETD-32 | 1.9 | 3.9 | 4.3 | — |
| DETD-33 | 1.8 | 4.2 | 2.7 | — |
| DETD-34 | 3.0 | 2.2 | 6.1 | — |
| DETD-35 | 1.7 | 3.5 | 3.2 | — |
| DETD-36 | 2.4 | 8.7 | 7.1 | — |
| DETD-37 | 3.0 | 6.7 | 6.2 | — |
| DETD-38 | 2.6 | 5.2 | 4.6 | — |
| DETD-39 | 0.8 | 1.9 | 2.1 | 3.7 |
| DETD-40 | 3.1 | 4.9 | 6.1 | — |
| DETD-41 | 2.8 | 5.0 | 5.3 | — |
| DETD-42 | 2.7 | 6.0 | 4.5 | — |
| DETD-43 | 2.4 | 6.9 | — | — |
| DETD-44 | 2.2 | 7.0 | — | — |
| DETD-45 | 2.0 | 3.1 | 3.1 | 4.7 |
| DETD-46 | 3.8 | 7.3 | — | — |
| DETD-47 | — | >15 | — | — |
| DETD-48 | — | 8.2 | — | — |
| DETD-49 | — | 9.5 | — | — |
| DETD-50 | 4.4 | 7.7 | — | — |
| DETD-51 | — | >15 | — | — |
| DETD-52 | — | >15 | — | — |
| DETD-53 | 4.1 | 3.8 | 4.1 | 4.8 |
| DETD-54 | 3.1 | 4.9 | — | — |
| DETD-55 | 2.8 | 4.1 | — | — |
| DETD-56 | 1.9 | 4.2 | 4.5 | — |
| DETD-57 | — | >15 | — | — |
| DETD-58 | 2.1 | 3.8 | 3.8 | 5.8 |
| DETD-59 | 3.5 | 5.1 | — | — |
| DETD-60 | 2.1 | 2.7 | 3.3 | 4.0 |
| DETD-61 | 2.5 | 3.4 | 3.6 | 4.7 |
| DETD-62 | — | 7.4 | — | — |

[a]: The cells were treated with compounds for 24 h, and the numbers in the table are the 50% inhibitory concentration ($IC_{50}$ in μM) of each compound on cell viability.
"—": $IC_{50}$ is not detectable at the measured concentrations up to 7.5-10 μM.

DET and DETD-35 Inhibits MDA-MB-231 Cell Migration and Invasion

Figure 1B:
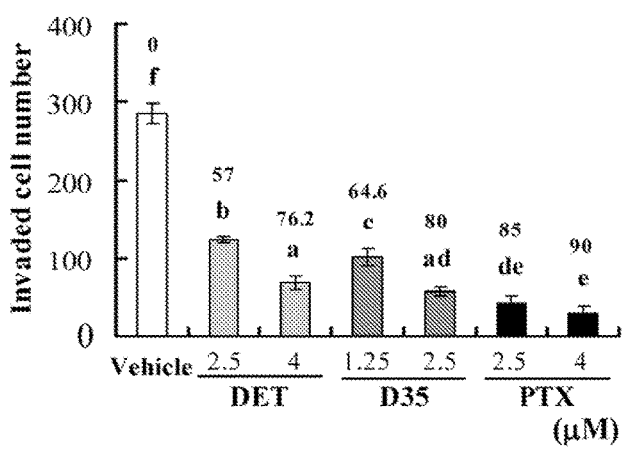

The Boyden chamber assay was used to investigate the effects of DET and DETD-35 on the migration and invasion activity of MDA-MB-231 cells, and PTX was a reference control. FIG. 1A shows that DET (2.5 and 4 μM), DETD-35 (1.25 and 2.5 μM) and PTX (2.5 and 4 μM) significantly inhibited cell migration in a concentration-dependent manner after 24 hrs of treatment. DET, DETD-35 and PTX at higher concentrations greatly reduced 77%, 84% and 88% of cell migration, as compared to the vehicle control group, while at lower concentrations DET, DETD-35 and PTX suppressed 16%, 10% and 87% of cell migration, respectively ($P<0.05$). Trans-well invasion assay further revealed that DET and DETD-35 inhibited invasion of MDA-MB-231 cells through a thin Matrigel matrix. At higher concentrations DET, DETD-35 and PTX significantly inhibited cell invasion by 76%, 80% and 90%, and at lower concentrations the anti-invasion effects were 57%, 64.6% and 85%, respectively ($P<0.05$) (FIG. 1B). These data suggest that DET and its derivative DETD-35 reduced the ability of cancer cells to migrate and invade basement membrane barriers.

Figure 2A:
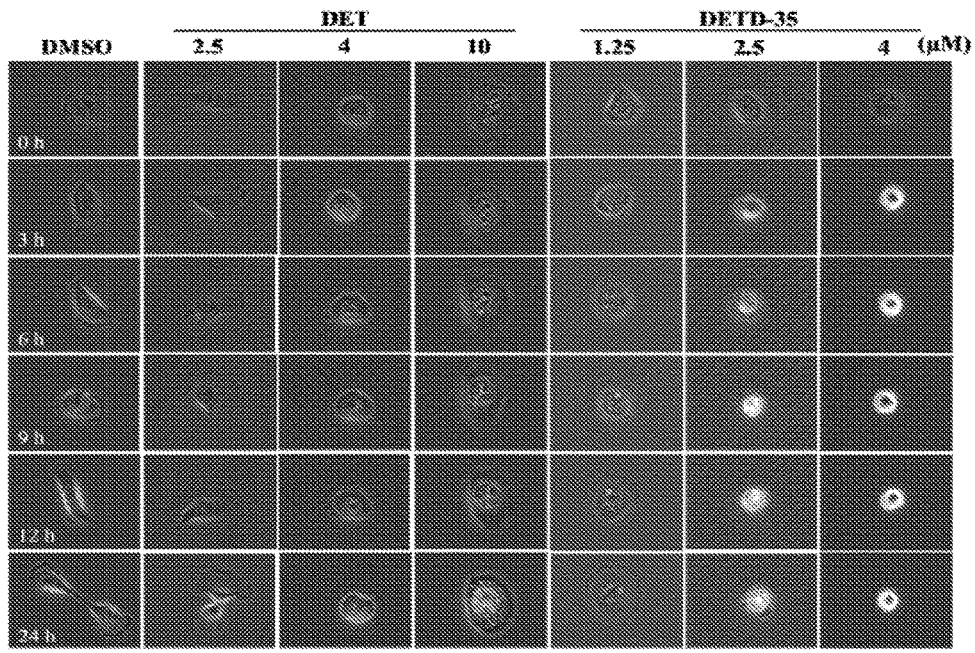
Figure 2C:
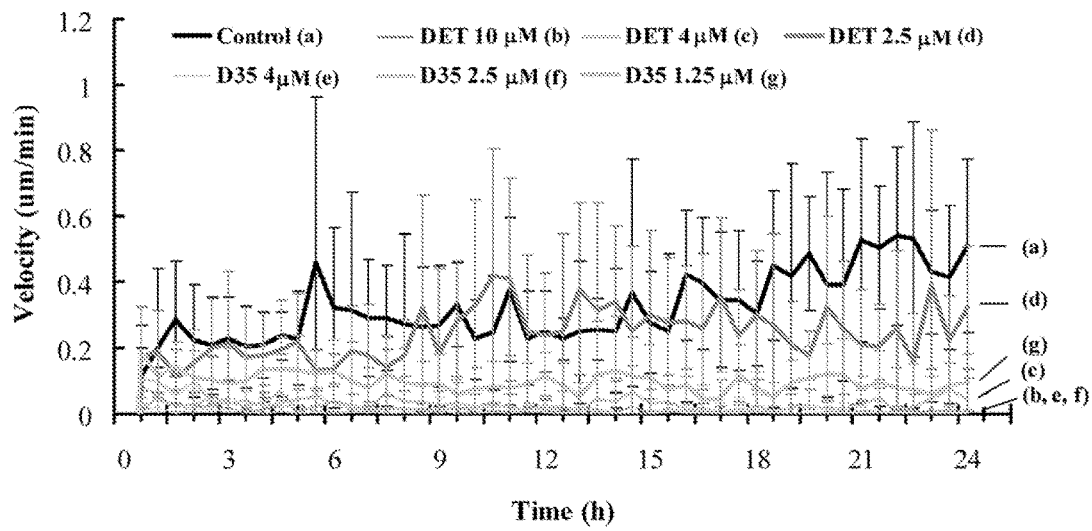
Figure 2D:
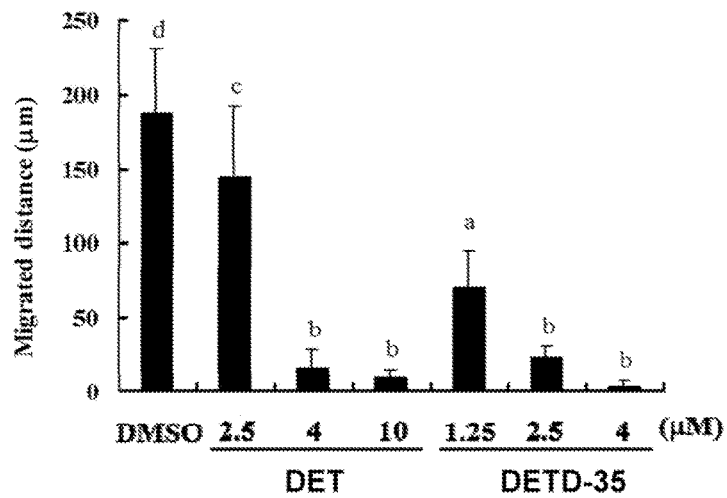

DETD-35 Exhibits Superior Effect than DET on Inhibiting Breast Cancer Cell Motility The effects of DET and DETD-35 on MDA-MB-231 cell motility were investigated and compared using time-lapse microscopy. Trajectories of MDA-MB-231 cells migrated within 24 h under different treatment conditions were monitored and analyzed. Vehicle control cells were observed to move energetically with robust membrane protrusion in a continuous motion (0-24 h), and general cell proliferation was captured at the time point within 24 h (FIG. 2A). As shown in FIG. 2B, the most significant cell dispersion area from the origin was observed in the vehicle control, and a relatively small area from restricted movements was observed in cells treated with 2.5 μM DET for 12 h, while much reduced cell trajectories were observed in cells treated with 4 and 10 μM DET, or 1.25, 2.5 and 4 μM DETD-35. In the cells treated with DETD-35 at 1.25, 2.5 and 4 μM, or treated with higher concentrations of DET at 4 and 10 μM, the suppression of movement became much more prominent with the average motility velocity decreased as compared to vehicle control cells and cells treated with 2.5 μM DET (FIG. 2C). The migration distances were significantly shorter in cells treated with 2.5, 4, 10 μM of DET (144 vs. 15 vs. 9 μm), or 1.25, 2.5, 4 μM of DETD-35 (70 vs. 23 vs. 3 μm) than that of the control (186 μM) (FIG. 2D). These results indicate that DETD-35, a newly synthesized sesquiterpene lactone exhibits potent and better bioactivity than DET in suppressing MDA-MB-231 cell motility.

DETD-35 Reduces Tumor Growth in Orthotopic Mammary Tumors in NOD/SCID Mice

The therapeutic efficacy of DETD-35 in xenograft NOD/SCID mice bearing MDA-MB-231 cancer cells was assessed. The tumor growth was significantly delayed in the DETD-35 (10 mg/kg, i.p.) treated group as compared to the control group at day-56 ($P<0.05$) (FIG. 3A), without affecting the mouse body weight (FIG. 3B). The tumor volume at day-71 decreased 1.8 folds (1268 vs. 712 mm$^3$) in the treated group as compared to the tumor control group (FIG. 3C). The organ index (organ weight/body weight, %) of lung, liver, kidney and spleen were calculated. The kidney index of the tumor control group was higher than the sham and DETD-35 treated groups (FIG. 3D).

DETD-35 Potently Suppresses Lung Metastasis of MDA-MB-231 Cells

The pretreatment and post-treatment effect of DETD-35 on the lung metastasis of triple negative breast tumor MDA-MB-231 in xenograft mice were compared with the reference chemotherapeutic drug PTX. In the pretreatment pre-DETD-35-10 group, the number of tumor foci in mice lungs was significantly reduced by 83% as compared to the tumor control group, while the suppressed effect of post-treatment with DETD-35-10 and PTX-5 were 50% and 62%, respectively. DETD-35-2 treatment had no statistically significant effect on inhibiting lung metastasis by 9%. The PTX-5+DETD-35-2 alternate-treatment group greatly reduced by 71% of lung tumor foci as compared to the alone treatment ($P<0.05$, FIG. 4A). The body weight of DETD-35-2 treatment group was slightly lower than other groups with no statistical difference (data not shown). The organ index of lung, liver, kidney, and spleen were no significantly difference in all tested animals (FIG. 4B).

Synergism Between DETD-35 or DETD-39 and PTX Against MDA-MB-231 Cells

Figure 5A:
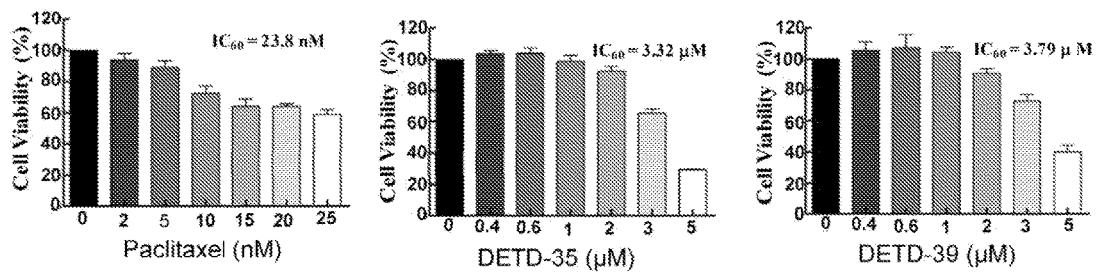
FIGS. 5A-D show compound-drug combination studies of DETD-35 and PTX or DETD-39 and PTX against MDA-MB-231 cells. (A) Inhibition of cell proliferation by PTX, DETD-35 and DETD-39. Cells were treated with indicated concentrations for 24 h. Cell viability was determined by MTT assay. (B) Bar graph showing the combination effect of PTX and DETD-35, and of PTX and DETD-39. (C) Classic isobologram analysis graph and (D) Combination index (CI) plot of DETD-35 or DETD-39 co-treatment with PTX. CI<1 indicates synergy; CI=1 indicates an additive effect; and CI>1 indicates antagonism.
Figure 5B:
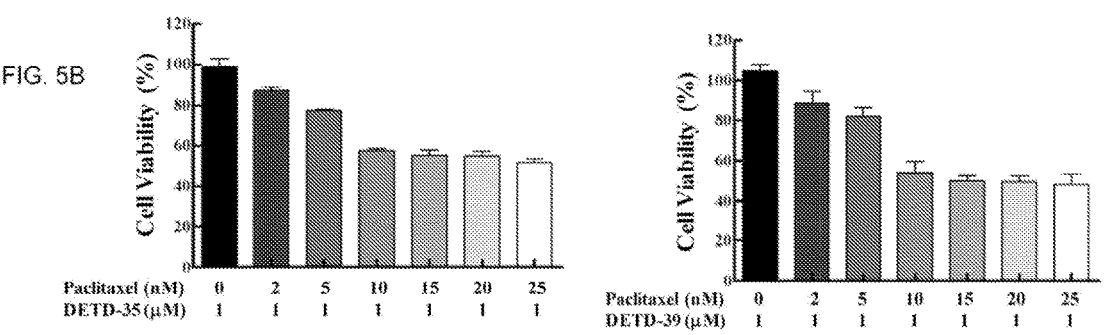
Figure 5C:
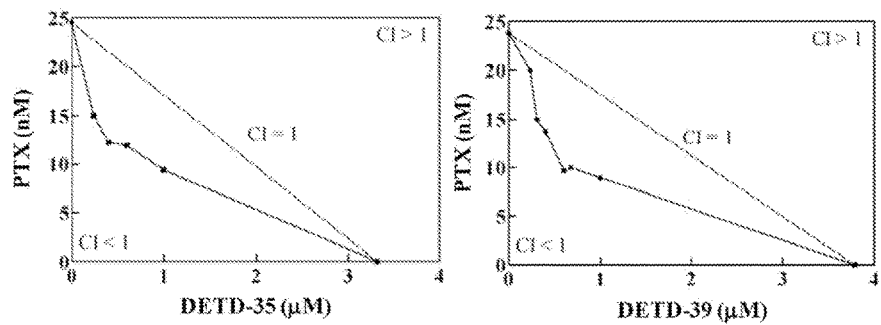
Figure 5D:
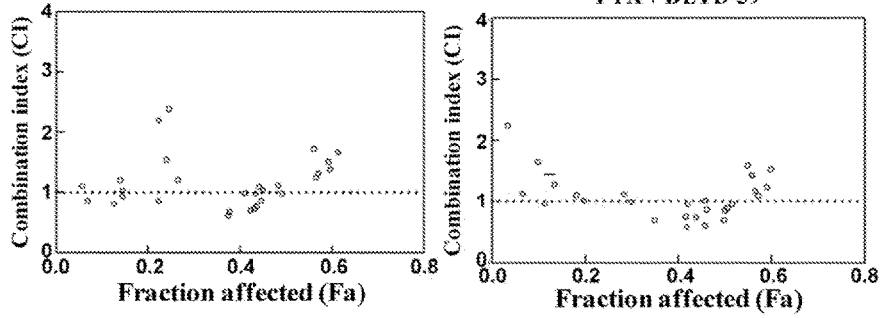

To investigate whether or not DETD-35 and DETD-39 act synergistically with PTX against MDA-MB-231 cell activity, anti-proliferation assay using MTT reagent was performed to obtain the $IC_{60}$ value of each compound. The $IC_{60}$ of PTX. DETD-35 and DETD-39 on MDA-MB-231 cells were 23.8 nM, 3.32 μM and 3.79 μM, respectively (FIG. 5A). Co-treatment with a fixing concentration of DETD-35 or DETD-39 (1 μM) and ascending concentrations of PTX (0, 2, 5, 10, 15, 20 and 25 nM) showed a better inhibition of cancer cell proliferation than PTX treatment alone (FIG. 5B). Based on the $IC_{60}$ values, DETD-35 or DETD-39 ranging from 0 to 4 μM and PIX from 0 to 25 nM were used for compound-drug combination study. Classic isobologram analysis and Chou-Talalay method were conducted to investigate the synergistic effect of compound and drug. Combination index (CI) was calculated with CalcuSyn software (Version 2.0, Biosoft) and expressed as CI vs. Fa (fraction affected). CI<1 indicates synergy; CI=1 indicates additive effect; and CI>1 indicates antagonism. DETD-35 or DETD-39 in combination with PTX acted synergistically to inhibit the growth of MDA-MB-231 cells (FIG. 5C-D).

DET and DETD-35 Enhance the Anti-Proliferative Effect of Gluthathione Synthesis Blockers Against MDA-MB-231 Cells We have observed that transient ROS production induced by DET is one of the upstream factors that trigger a cascade response leading to cancer cell death. Gamma-glutamylcysteine synthetase inhibitor "buthionine sulfoximine (BSO)" and cystine/glutamate transporter (xCT) inhibitor "sulfasalazine" are known for their functions to weaken glutathione-mediated antioxidant defense and were chosen for combination drug effect study. The synergism between DET or its analog (DETD-35) and BSO or sulfasalazine were investigated. If such synergism exists, it will/may have great potential in preventing the resistance and/or increasing the sensitivity of DET/DETD35 and phase II drug BSO or clinical drug sulfasalazine for treating cancers.

Figure 6A:
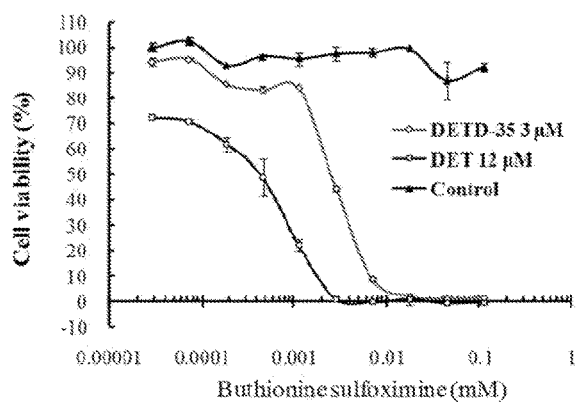
FIGS. 6A-B show that DET and DETD-35 can effectively decrease the viability of MDA-MB-231 cells pre-treated with buthionine sulfoximine and sulfasalazine. (A) Inhibition of MDA-MB-231 cell proliferation by DET and DETD-35 after pretreated with buthione sulfoximine. Cells were pre-treated with indicated concentrations of BSO for 30 h, and followed by 24-h treatment of DET and DETD-35 at the concentration of 12 µM and 3 µM, respectively. Cell viability was determined by MTT assay. (B) Inhibition of MDA-MB-231 cell proliferation by DET and DETD-35 after pretreated with sulfasalazine. Cells were pre-treated with indicated concentrations of sulfasalazine for 30 h, and followed by 24-h treatment of DET and DETD-35 at the concentration of 12 µM and 3 µM, respectively. Cell viability was determined by MTT assay.
Figure 6B:
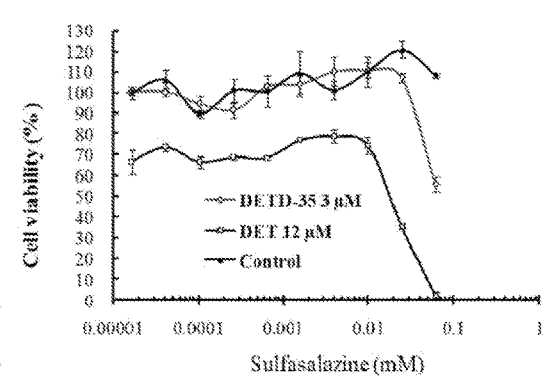

BSO and sulfasalazine did not show any cytotoxicity to MDA-MB-231 cells at an indicated range of concentrations, but DET and DETD-35 can sensitize both drugs' effect. After MDA-MB-231 cells were pretreated with of BSO or sulfasalazine for 30 hours, the viability of the cells treated with a fixed concentration of DET (12 μM) and DETD-35 (3 μM) for 24 h can be further reduced from around 70% and 90% to 1% or undetectable (FIG. 6A-B). The BSO at 0.5 μM, 3 μM, and above, synergistic effects with either DET or DETD-35 were observed (FIG. 6A). Similarly, sulfasalazine at 25 μM, 62 μM, and above, synergistic effects were also observed with either DET or DETD-35 (FIG. 6B). This new discovery show that DET and DETD-35 used in combination with either clinical drug sulfasalazine or phase II drug BSO can sensitize both compound drug efficacy towards inhibiting triple negative breast cancer cell activity.

Inhibitory Effects of DET and Newly Synthesized DETDs Against Melanoma Cell Proliferation Several genes are involved in melanoma development and pathology; specifically, mutation in V-raf murine sarcoma viral oncogene homolog B1 (B-RAF) occurs approximately 50-60% and in neuroblastoma RAS viral oncogene homolog (N-RAS) occurs about 30% of malignant melanomas. A spectrum of wild-type or mutated melanoma cell lines including B16-F10, MeWo, A375, A2058, HTB-68, and melanocyte were used to study anti-melanoma cell proliferation activity of parental phytocompound DET and newly synthesized DETDs. Table 4 shows the $IC_{50}$ values of DET and its derivatives (DETDs) in inhibiting proliferation of different melanoma cell lines, normal melanocytes, macrophages, and LPS-induced nitric oxide (NO) production in RAW 264.7 cells[a], analyzed by MTT assay after 24-h treatment. Different cell lines showed different sensitivities to DET and DETDs. The $IC_{50}$ of DET for B16-F10 and A375 were about 6 μM, but DET did not show detectable activity against other melanoma cell types at tested concentrations up to 10 μM. Among the tested sixty DETDs (DETD-1 to DETD-62), DETD-6, -28, -30, -33, -34, -35, -39, -45, -53, -54, -55, 56, -58, -60, and -61 could inhibit all types of melanoma cell lines, with $IC_{50}$ values within 1.6-9.9 μM. DETD-35 ($IC_{50}$=2.5~6.0 μM) and DETD-39 ($IC_{50}$=1.6~3.5 μM) showed the most potent anti-melanoma cell proliferation effects, but DETD-39 also showed some toxicity to normal human melanocytes with $IC_{50}$ of 9 μM.

TABLE 4

| Cpds | B16-F10[b] (NRAS mutation) | MeWo[c] (No NRAS or BRAF mutation) | HTB-68[c] (NRAS mutation) | A2058[c] (BRAF mutation) | A375[c] (BRAF mutation) | Melanocyte[c] (Normal cells) | RAW264.7[b] (normal macrophage) | NO production |
|---|---|---|---|---|---|---|---|---|
| DET | 6.0 | — | — | — | 5.9 | — | — | 2.9 |
| DETD-1 | — | — | — | — | — | — | — | 5 |
| DETD-3 | — | — | — | — | — | — | — | — |
| DETD-4 | 4.5 | — | — | — | — | — | — | 2.2 |
| DETD-5 | 4.7 | — | 7.8 | 5.8 | 4.1 | — | — | 2.4 |
| DETD-6 | 3.9 | 9.9 | 5.7 | 3.9 | 3.3 | — | — | 2.5 |
| DETD-7 | 4.8 | — | 8.4 | 5.5 | 4.9 | — | — | 2.2 |
| DETD-8 | 6.8 | — | — | — | — | — | — | 2.5 |
| DETD-9 | — | — | — | — | — | — | — | — |
| DETD-10 | 6.0 | — | — | — | — | — | — | 1.8 |
| DETD-11 | — | — | — | — | — | — | — | 2.3 |
| DETD-12 | 7.2 | — | — | — | — | — | — | 3.2 |
| DETD-13 | 7.1 | — | — | — | — | — | — | 2.0 |
| DETD-14 | — | — | — | — | — | — | — | 2.2 |
| DETD-16 | — | — | — | — | — | — | — | 3.2 |
| DETD-17 | — | — | — | — | — | — | — | 2.0 |
| DETD-18 | 8.4 | — | — | — | — | — | — | 3.4 |
| DETD-19 | 7.8 | — | — | — | — | — | — | 3.8 |
| DETD-20 | 9.0 | — | — | — | — | — | — | 4.2 |
| DETD-21 | — | — | — | — | — | — | — | 4.7 |
| DETD-22 | 6.8 | — | — | — | — | — | — | 3.5 |
| DETD-23 | 8.6 | — | — | — | — | — | — | 3.8 |
| DETD-24 | — | — | — | — | — | — | — | 4.4 |
| DETD-25 | — | — | — | — | — | — | — | 4.9 |
| DETD-26 | 5.0 | — | — | — | — | — | — | 1.7 |
| DETD-27 | 4.8 | — | — | — | — | — | — | 1.9 |
| DETD-28 | 3.9 | 6.7 | 6.1 | 4.4 | 3.0 | — | — | 2.1 |
| DETD-29 | 6.7 | — | — | — | — | — | — | 1.6 |
| DETD-30 | 2.5 | 9.1 | 7.6 | 5.2 | 3.4 | — | — | 1.6 |
| DETD-31 | 2.9 | — | — | — | 4.3 | — | — | 3.2 |
| DETD-32 | 4.2 | — | — | — | — | — | — | 2.6 |
| DETD-33 | 2.2 | 6.7 | 5.9 | 4.2 | 2.9 | — | — | 1.9 |

TABLE 4-continued

| Cpds | B16-F10[b] (NRAS mutation) | MeWo[c] (No NRAS or BRAF mutation) | HTB-68[c] (NRAS mutation) | A2058[c] (BRAF mutation) | A375[c] (BRAF mutation) | Melanocyte[c] (Normal cells) | RAW264.7[b] (normal macrophage) | NO production |
|---|---|---|---|---|---|---|---|---|
| DETD-34 | 2.0 | 7.3 | 6.8 | 4.4 | 3.1 | — | — | 2.3 |
| DETD-35 | 2.7 | 6.0 | 3.9 | 3.1 | 2.5 | — | — | 1.5 |
| DETD-36 | 9.4 | — | — | — | 9.2 | — | — | 1.8 |
| DETD-37 | 3.8 | — | — | — | — | — | — | 2.0 |
| DETD-38 | 3.9 | — | 9.5 | — | 5.1 | — | — | 1.7 |
| DETD-39 | 1.7 | 3.5 | 3.2 | 2.4 | 1.6 | 9.0 | 3.5 | 1.0 |
| DETD-40 | 4.3 | — | — | — | — | — | — | 4.5 |
| DETD-41 | 5.5 | — | — | — | — | — | — | 3.5 |
| DETD-42 | 5.5 | — | — | — | — | — | — | 2.9 |
| DETD-43 | 7.4 | — | 8.2 | 8.7 | 3.6 | — | — | 3.5 |
| DETD-44 | 7.3 | — | 7.6 | 8.5 | 3.5 | — | — | 3.4 |
| DETD-45 | 4.5 | 4.5 | 3.5 | 3.6 | 1.7 | — | — | 2.8 |
| DETD-46 | 5.4 | 6.3 | 4.5 | 5.0 | 2.6 | — | — | 3.1 |
| DETD-47 | — | — | — | — | 8.3 | — | — | — |
| DETD-48 | — | — | — | — | 6.9 | — | — | — |
| DETD-49 | — | — | — | — | 4.9 | — | — | 3.4 |
| DETD-50 | 9.4 | 9.3 | — | 8.7 | 4.6 | — | — | — |
| DETD-51 | — | — | — | — | — | — | — | — |
| DETD-52 | — | — | — | — | — | — | — | — |
| DETD-53 | 5.2 | 6.0 | 5.0 | 5.5 | 2.8 | — | — | 3.5 |
| DETD-54 | 6.6 | 7.9 | 7.0 | 6.6 | 3.4 | — | — | — |
| DETD-55 | 4.8 | 9.0 | 5.3 | 6.1 | 2.6 | — | — | 2.9 |
| DETD-56 | 5.3 | 7.6 | 4.5 | 5.2 | 2.5 | — | — | 3.0 |
| DETD-57 | 8.1 | — | 8.0 | 8.3 | 4.2 | — | — | — |
| DETD-58 | 5.6 | 8.3 | 3.8 | 5 | 2.1 | — | — | 3.6 |
| DETD-59 | 6.3 | — | 4.8 | 6.0 | 2.6 | — | — | — |
| DETD-60 | 4.9 | 4.8 | 4.9 | 4.1 | 2.0 | — | — | 3.0 |
| DETD-61 | 6.0 | 6.6 | 5.5 | 5.2 | 2.6 | — | — | 3.1 |
| DETD-62 | 9.3 | — | 9.0 | 8.7 | 5.0 | — | — | — |

Figure 7A:
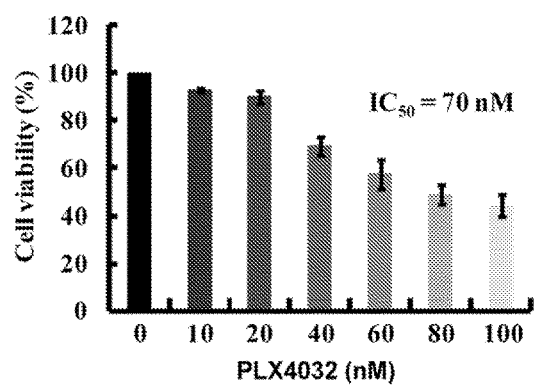
FIGS. 7 A-D show inhibition of A375 melanoma cell proliferation by PLX4032 and DETD-35. Cells were treated with indicated concentration of PLX4032 (A) or DETD-35 (B) for 72 h. Cell viability was determined by MTT assay. (C) Bar graph showing the combination effect of PLX4032 and DETD-35. (D) Combination index (CI) plot of DETD-35 co-treatment with PLX4032. CI<1 indicates synergy; CI=1 indicates an additive effect; and CI>1 indicates antagonism.
Figure 7B:
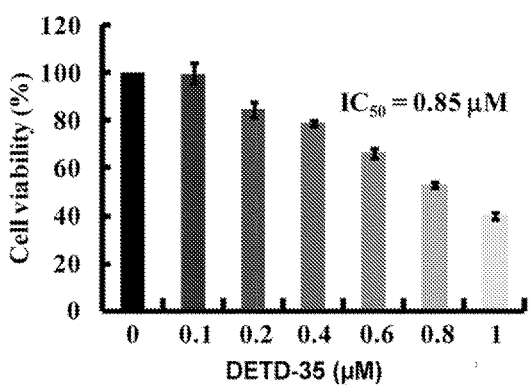
Figure 7C:
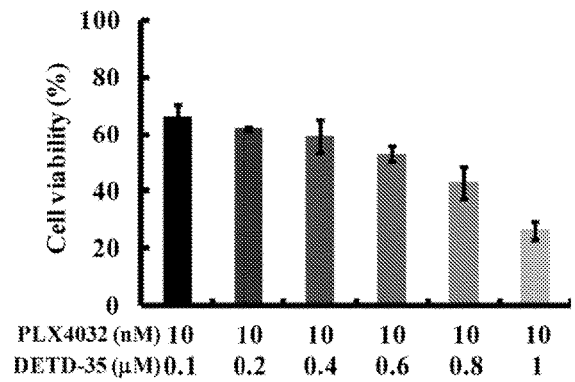
Figure 7D:
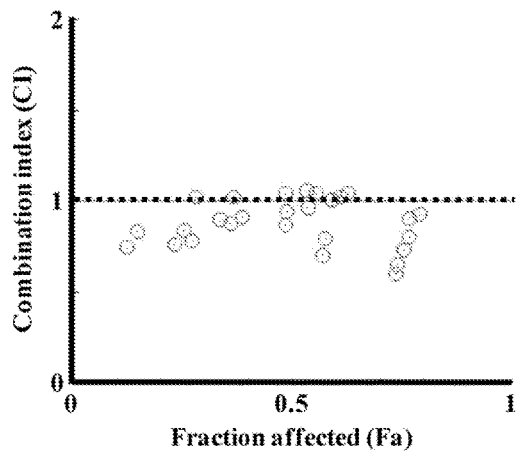

[a]The cells were treated with compounds for 24 h, and the numbers in the table are the 50% inhibitory concentration ($IC_{50}$ in μM) of each compound on cell viability.
[b]mouse cell line;
[c]human cell line
"—": $IC_{50}$ is not detectable at the measured concentrations up to 10 μM Synergism of DETD-35 and PLX4032 Against A375 Melanoma Cells To investigate whether or not DETD-35 show synergism with PLX4032 against A375 melanoma cells, we performed anti-proliferation assay using MTT reagent to obtain $IC_{50}$ of each compound. The $IC_{50}$ of PLX4032 and DETD-35 on A375 cells were 0.07 and 0.85 μM, respectively (FIG. 7A-B). Based on the $IC_{50}$ of each compound, we fixed concentrations of DETD-35 ranging from 0.1 to 1 μM and PLX4032 from 10 to 100 nM for compound-drug combination study. The synergistic effect was quantified by combination index (CI) analysis as stated above. DETD-35 in combination with PLX4032 acted synergistically to inhibit the growth of A375 melanoma cells (FIG. 7C-D).

DETD-35 Overcomes Acquired Resistance to PLX4032 in A375 Melanoma Cells

Figure 8A:
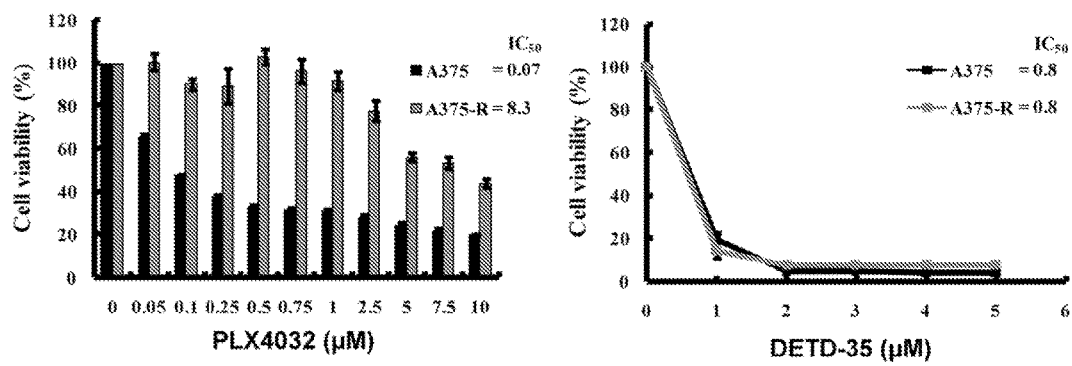
FIGS. 8 A-C show DETD-35 overcomes resistance to PLX4032 in A375 melanoma cell. (A) A375 and A375-R cells were treated with indicated concentrations of PLX4032 and DETD-35, respectively for 72 h. Cell viability was determined by MT assay. (B) Expression profile of key molecules involved in MAPK signaling pathway in parental A375 and resistance A375-R cells treated with PLX4032. The total cellular proteins from both cells treated with PLX4032 for 6 h were subjected to Western blot analysis. (C) Western blot analysis of the effects of PLX4032 (1 µM), DETD-35 (1 µM and 3 µM). MEK inhibitor PD0325901 (1 µM), PLX4032+DETD-35 or PLX4032+PD co-treatment on key molecules involved in MAPK signaling pathway in A375-R cells.
Figure 8B:
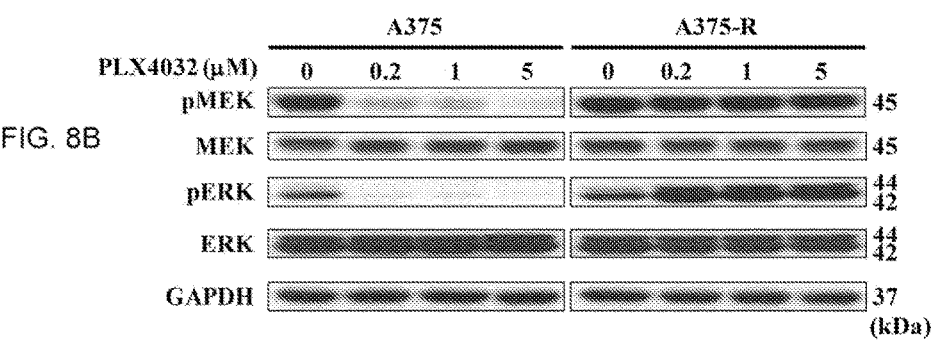
Figure 8C:
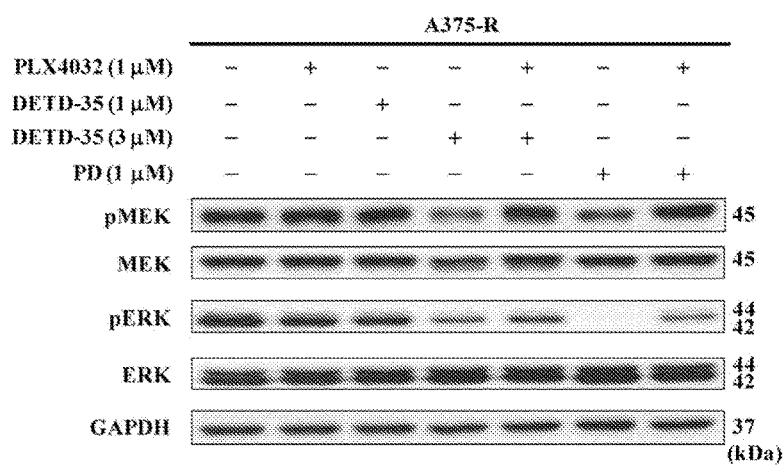

To study the mechanisms underlying how DETD-35 overcomes acquired resistance to BRAF inhibitor, we generated A375 cell line resistant to PLX4032 (designated A375-R). Briefly, A375 melanoma cells were seeded in T75 plate and treated with ascending concentration of PLX4032 (20, 50, 100, 250, 500, 1000, 2000 nM) through approximately 2 months and 20 passages. We have successfully developed acquired resistance cell line A375-R because it was more than 100-fold less sensitive to PLX4032 ($IC_{50}$: 8.3 vs. 0.07 μM; FIG. 8A, left panel) as compared to the parental cell line whereas DETD-35 showed no different effect on A375 and A375-R cell viability in which $IC_{50}$ of DETD-35 was 0.8 μM for both cell lines (FIG. 8A, right panel). Moreover, PLX4032 inhibited MAPK signaling molecules phospho-MEK and phospho-ERK in parental A375 cells but not in A375-R cells (FIG. 8B). These reactivation of MAP kinases in A375-R cell treated with PLX4032 further confirmed the successful generation of the resistance cell line. The results of western blot analysis showed that DETD-35 inhibited reactivation of MAP kinases in A375-R cells (FIG. 8C). DETD-35 also inhibited MAPK signaling molecules while co-treated with PLX40332, suggesting the action of DETD-35 in overcoming acquired resistance to PLX4032.

Structure Activity Relationship of DETDs Against Proliferation of Various Cancer Cell Lines Based on toxicity results of DET and DETDs on different breast cancer and melanoma cell lines, we selected DETD-6, -32, -35 and -39, under the consideration of structure activity relationship for evaluating their suppression effect against other cancer types of cell line with indicated tumor origin in Table 5. In addition to effectively inhibit on breast cancer and melanoma cell growth, the four tested DETDs also show superior inhibition on brain, lung, lymphoma, neuroepithelioma, kidney, prostate, stomach, colon and uterus cancer cell proliferation. The most suppression effect in different cancer types was observed in DETD-35 with no detected toxicity against normal cell lines M10, melanocytes, and macrophages (Tables 3 and 4). Thus, DETD-35 shows a great potential for further development into an anticancer drug. DETD-6 and -39 also showed activity on different cancer types, but they also showed some toxicity in normal cells in vitro. Table 5 shows 50% inhibitory concentrations ($IC_{50}$, μM) of DET and selected DETDs in inhibiting viability of various cancer cell types. The cells were treated with compounds for 24 h and then subjected to MTT assays.

TABLE 5

| Cell name | Tumor origin | DET | DETD-6 | DETD-32 | DETD-35 | DETD-39 |
| --- | --- | --- | --- | --- | --- | --- |
| MCF-7 | Breast | 5.0 | 4.8 | 4.3 | 3.9 | 2.4 |
| MDA-MB-231 | Breast | 14.0 | 4.0 | 3.9 | 3.5 | 1.9 |
| TS/A (mouse) | Breast | 2.6 | 1.8 | 1.9 | 1.7 | 0.8 |
| B16-F10 (mouse) | Skin | 6.00 | 3.90 | 4.20 | 2.70 | 1.70 |
| U-87MG | Brain | 1.00 | 0.35 | 0.42 | 0.34 | 0.15 |
| PC6 | Lung | 0.40 | 0.17 | 0.47 | 0.34 | 0.11 |
| U937 | Lymphoma | 0.48 | 0.18 | 0.39 | 0.18 | 0.10 |
| SK-N-MC | Neuroepithelioma | 0.51 | 0.32 | 0.51 | 0.26 | 0.11 |
| A498 | Kidney | 2.82 | 1.11 | 1.48 | 0.79 | 0.48 |
| PC3 | Prostate | 12.8 | 4.5 | 6.2 | 5.5 | 2.6 |
| KATO III | Stomach | 1.47 | 0.42 | 0.82 | 0.65 | 0.29 |
| HCT-116 | Colon | 0.28 | 0.11 | 0.36 | 0.14 | 0.10 |
| NES-SA | Uterus | 0.90 | 0.42 | 0.50 | 0.34 | 0.14 |

Inhibition of Nitric Oxide (NO) Production in LPS-Stimulated Macrophages

LPS from the outer membrane of Gram-negative bacteria can induce mRNA or protein levels of inducible nitric oxide synthase (iNOS), which catalyzes oxidative deamination of L-arginine to produce nitric oxide (NO). Once NO is predominantly produced, it interacts with superoxide anion and generates highly reactive oxidants resulting in cellular inflammation, DNA, protein and tissue damages, carcinogenesis, and antiapoptosis. We used in vitro LPS stimulated inflammation in RAW264.7 cell system to evaluate the effect of DET and its derivatives DETDs on NO production by determination of nitrite level (equivalent to NO level) in culture medium 24 h after LPS treatment. The DET itself was already a potent NO inhibitor with $IC_{50}$ of 2.9 µM. Most of the DETDs showed inhibition on LPS induced NO production in macrophages. The most potent effect was DETD-35 and DETD-39 with a 2- and 3-fold decrease in $IC_{50}$ values (1.5 and 1.0 µM). DETD-39 also showed detectable toxicity to the normal murine macrophage RAW 264.7 cell with $IC_{50}$ of 3.5 µM (Table 4).

DETD-35 Alone or in Combination with PLX4032 Suppresses Tumor Growth in A375 Orthotopic Xenograft Model We used A375 human melanoma xenograft model to evaluate the in vivo bioefficacy of DET. DETD-35, PLX4032 and compound drug combination. FIG. 9A shows the experimental design of in vivo study. For single compound or drug treatment group, PLX4032 was administered i.p. every day and DET and DETD-35 were administered i.p. every two days. For combination treatment, PLX4032 was administered every two days while DET and DETD-35 were administered every four days. It was found that DET (20 mg/kg), DETD-35 (20 mg/kg) could suppress tumor growth and reduce tumor mass by 47.5% and 70.5%, respectively, as effective as the clinical drug PLX4032 (20 mg/kg) (71.9%) as compared to the tumor control group (100%) with P<0.001 (ANOVA). Compound-drug combinational treatments were carried out with alternative administration of DET (20 mg/kg) or DETD-35 (20 mg/kg) and PLX4032 (20 mg/kg) by which DET or DETD-35 and PLX4032 treatment frequency were only half of the single compound or drug administration alone. All of the treatment did not show deteriorate effect to the mouse body weight (data not shown). The results show that similar tumor mass inhibition efficacy (72.3%) as single agent treatment, representing the synergism of DETD-35 and PLX4032 in mice (FIGS. 9B-D).

DETD-35 Overcomes Acquired PLX4032 Resistance in a Mouse Xenograft Model

Figure 10A:
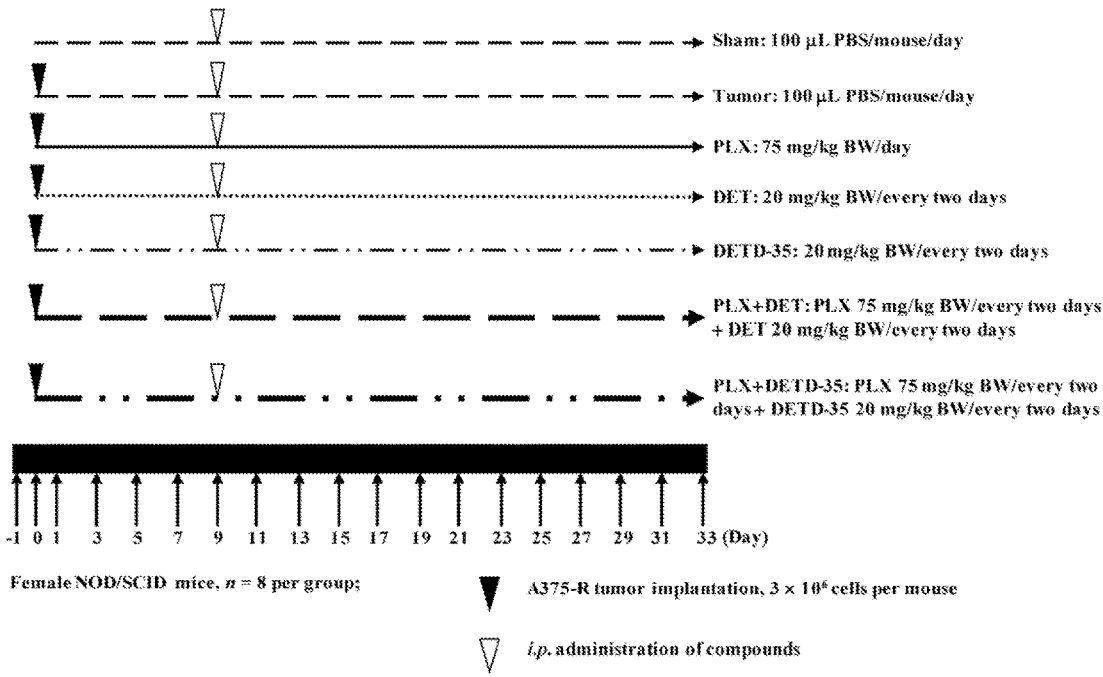
FIGS. 10 A-D show DETD-35 overcomes acquired PLX4032 resistance in a mouse xenograft model. (A) Experimental design of the study. (B) Representative pictures of isolated tumor tissue from each treatment groups. (C) Mean tumor volume after a 33-day of tumor cell implantation with or without compound treatment. (D) Average tumor mass of each treatment groups, data are mean±SEM, n=8. Means without a common letter differ, P<0.05 (ANOVA).
Figure 10B:
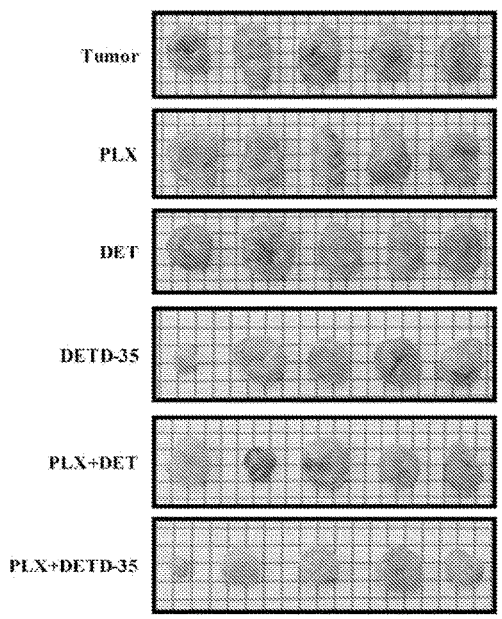
Figure 10C:
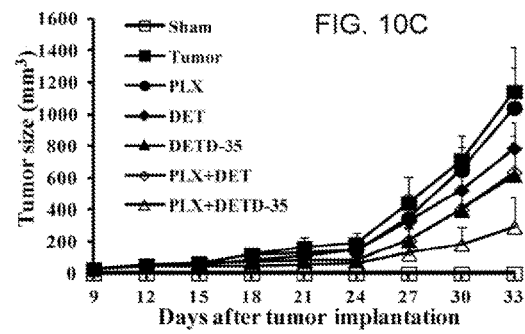
Figure 10D:
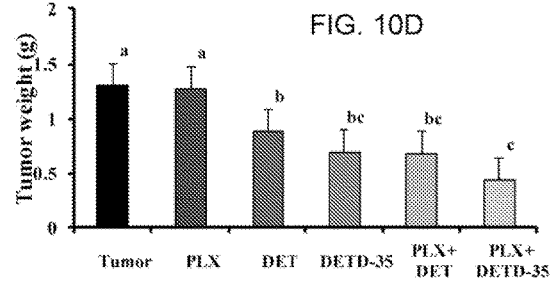

To study whether or not DETD-35 could overcome acquired resistance to BRAF inhibitor, we generated A375 cell line resistant to PLX4032 (designated A375-R) as described above. We then conducted A375-R orthotopic xenograft study. FIG. 10A shows the experimental design. The administration route and dose were identical to that of the study on inhibition of A375 orthotopic tumor growth described above except that PLX4032 was administered 75 mg/kg in a single drug treatment, and DET or DETD-35 alone was administered every two days in a combination treatment. We observed that PLX4032 showed no more anti-tumor activity with tumor growth rate and sizes similar to the tumor control group (100% in control group vs. 98% in PLX4032-treated group), as expected that the cell line is resistant to PLX4032. DET (20 mg/kg) or DETD-35 (20 mg/kg) alone could suppress tumor growth and reduce tumor mass 32% (P<0.01) and 46.9% (P<0.001), respectively. The combination of DETD-35 and PLX4032 exhibited the most effective anti-tumor growth activity against acquired PLX4032 resistance melanoma (65.3% reduce tumor mass, P<0.001) among the treatment groups, suggesting DETD-35 could sensitize PLX4032 effect (FIGS. 10B-D). All of the treatment did not show deteriorate effect to the mouse body weight (data not shown). The results suggested that DET and DETD-35 alone or in combination with PLX4032 could overcome acquired PLX4032 resistance in melanoma in vivo.

Figure 11A:
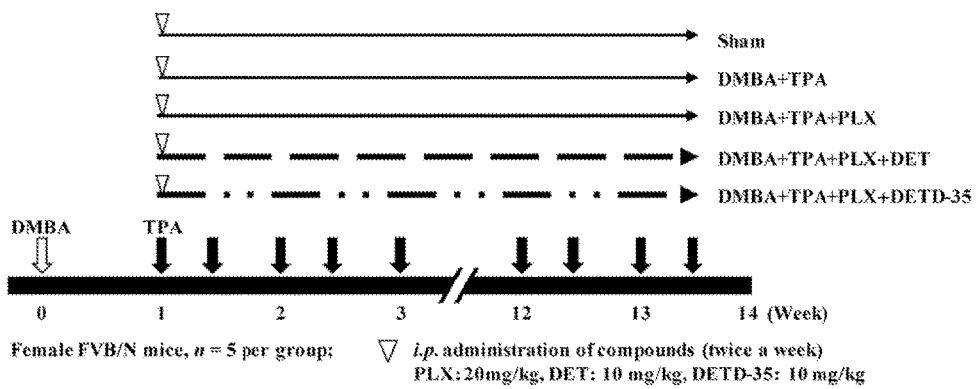
FIGS. 11 A-D show DETD-35 reduces cutaneous side effects of PLX4032 in a two-stage skin carcinogenesis model. (A) Experimental design of the study. (B) Representative pictures of skin papillomas from each treatment group. (C) Average papilloma number from each treatment group after one time of DMBA treatment followed by two times/week TPA treatment for 13 weeks, with or without compound treatment. (D) Average papiloma volume of each treatment group. Data are mean±SEM, n=5. Means without a common letter differ, P<0.05 (ANOVA).
Figure 11B:
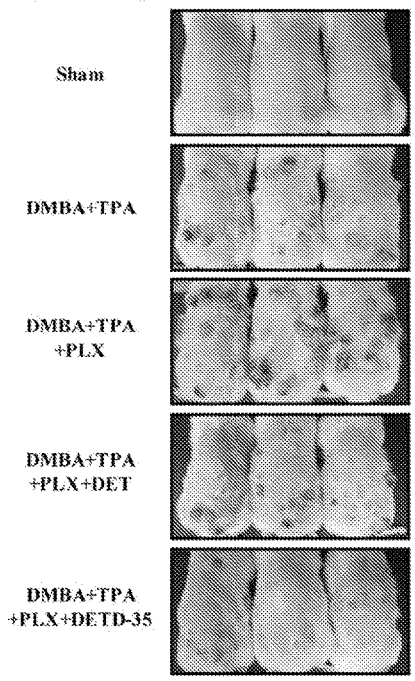
Figure 11C:
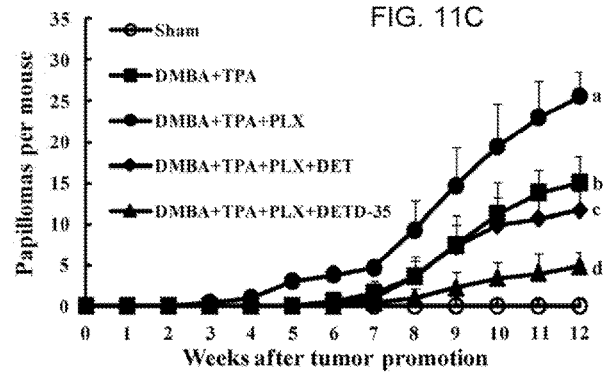
Figure 11D:
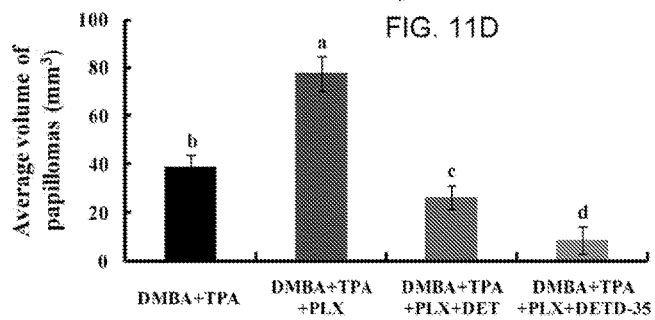

DETD-35 Retards PLX4032-Induced Acceleration of Papillomas Formation and Decreases Total Papillomas Number in Mice Mutations in RAS gene are frequently observed in cutaneous squamous-cell carcinomas and keratoacanthomas that could be developed in patients treated with PLX4032. We used a DMBA/TPA-induced skin carcinogenesis mouse model mimicking cutaneous side effect caused by PLX4032 to evaluate whether DETD-35 could reduce the cutaneous side effect of PLX4032. FIG. 11A illustrates the experimental design. One week after treatment of DMBA to dorsal skin of the mice, TPA was applied two times/week to the same area of the skin along with i.p. administration twice per week of PLX4032 (20 mg/kg), DET (10 mg/kg) and DETD-35 (10 mg/kg), respectively to different groups of mice. Papillomas formation in DMBA-TPA treated mice started between week 6 to 7 and PLX4032 treatment could promote the papillomas formation in DMBA-TPA treated mice earlier starting from weeks 3 to 4. Administration of DET (10 mg/kg) or DETD-35 (10 mg/kg) could retard PLX4032-induced acceleration of skin papillomas formation and also decreased total papillomas number from 25.6 to 11.7 and 4.8, and their sizes in average from 77.6 to 26.3 and 8.9 mm$^3$, respectively in mice (FIGS. 11B-D). All of the treatment did not show deteriorate effect to the mouse body weight (data not shown). The results indicate that both DET and DETD-35 could reduce cutaneous side effect of PLX4032, and DETD-35 is superior to DET at the same dose and scheme.

TABLE 6

Formula (I)

| Compound Number | Compound Structure | Substituents of Formula (I) |
| --- | --- | --- |
| DETD-3 | | $R_1$ = hydrogen |
| DETD-4 | | $R_1$ = —CO—C(CH$_3$)=CH$_2$ |
| DETD-5 | | $R_1$ = —CO—(E)C(CH$_3$)=CHCH$_2$CH$_3$ |
| DETD-6 | | $R_1$ = —CO—(E)CH=CH-phenyl |
| DETD-7 | | $R_1$ = —CO—(E)CH=CH-(3,4,5-trimethoxy)phenyl |
| DETD-8 | | $R_1$ = —CO—CH=C(CH$_3$)$_2$ |

TABLE 6-continued
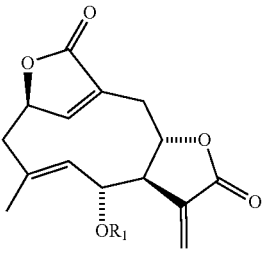
Formula (I)
| Compound Number | Compound Structure | Substituents of Formula (I) |
| --- | --- | --- |
DETD-9
$R_1$ = —CO—CH(Cl)$_2$
DETD-10
$R_1$ = —CO—CH$_2$—CH(CH$_3$)$_2$
DETD-11
$R_1$ = —CO—CH$_2$C(CH$_3$)(CH$_2$CH$_3$)(OCOCH$_3$)
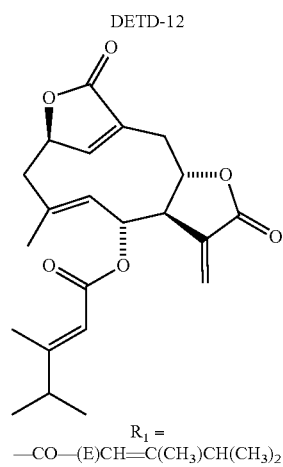
DETD-12
$R_1$ = —CO—(E)CH=C(CH$_3$)CH(CH$_3$)$_2$
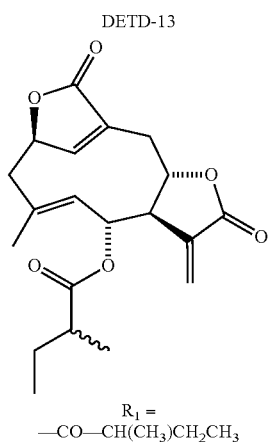
DETD-13
$R_1$ = —CO—CH(CH$_3$)CH$_2$CH$_3$
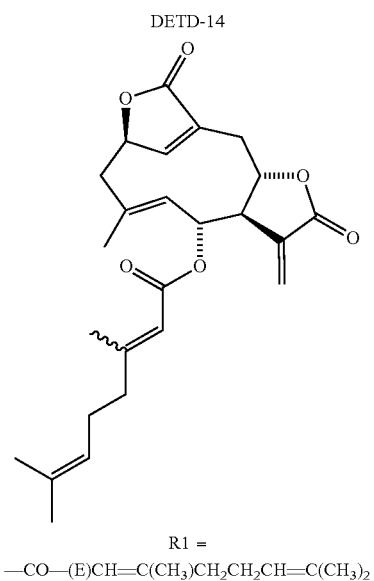
DETD-14
R1 = —CO—(E)CH=C(CH$_3$)CH$_2$CH$_2$CH=C(CH$_3$)$_2$ TABLE 6-continued
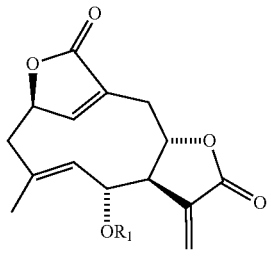
Formula (I)
| Compound Number | Compound Structure | Substituents of Formula (I) |
|---|---|---|
DETD-16
R1 = —CO—CH(CH₂CH₃)₂
DETD-17
R1 = —CO—CH₃
DETD-18
R1 = —CO—CH₂C(CH₃)CH₂CH₃
DETD-19
R1 = —CO—C(CH₂CH₃)=CH₂
DETD-20
R1 = —CO—C(CH₃)(CH₂)₂CH₃
DETD-21
R1 = —CO—C(CH₂CH₃)(CH₂)₃CH₃
DETD-22
DETD-23
R1 = —CO—CH₂C(OH)((CH)(CH₃)₂)₂
DETD-24
R1 = —CO—(E)CH=CHCH₃

TABLE 6-continued
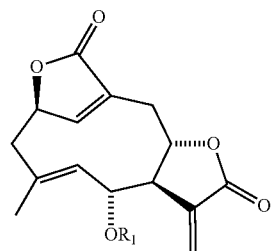
Formula (I)
| Compound Number | Compound Structure | Substituents of Formula (I) |
| --- | --- | --- |
R1 =
—CO—CH(CH₃)(CH₂)₃CH₃
DETD-25
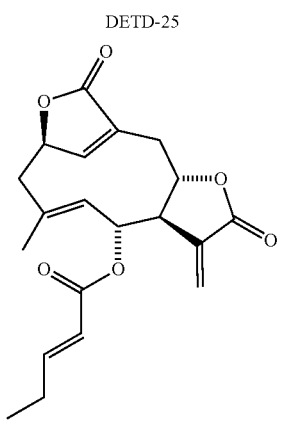
R1 =
—CO—(E)CH=CHCH₂CH₃
DETD-26
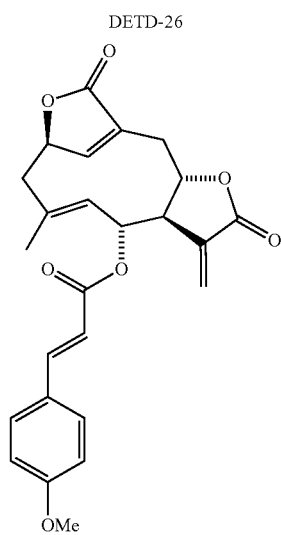
R = —CO—(E)CH=CH-(4-methoxyphenyl)
DETD-27
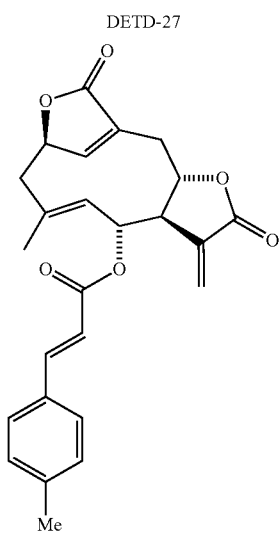
R = —CO—(E)CH=CH-(4-methylphenyl)
DETD-28
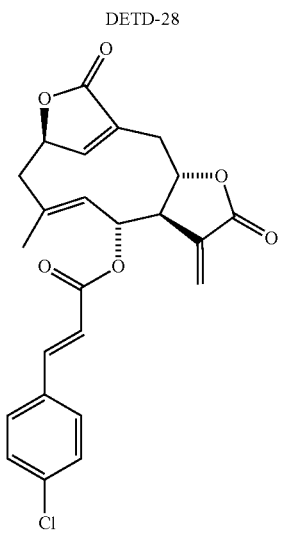
R = —CO—(E)CH=CH-(4-chlorophenyl)
DETD-29
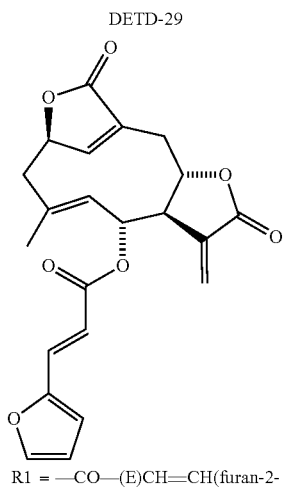
R1 = —CO—(E)CH=CH(furan-2-yl)
DETD-30
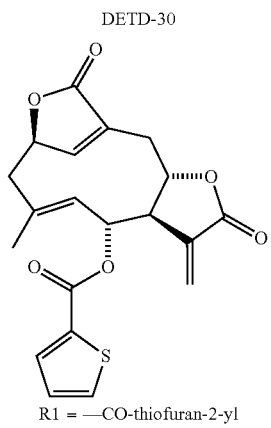
R1 = —CO-thiofuran-2-yl TABLE 6-continued
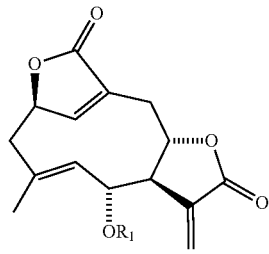
Formula (I)
| Compound Number | Compound Structure | Substituents of Formula (I) |
| --- | --- | --- |
| DETD-31 | | R1 = —CO-phenyl |
| DETD-32 | | R1 = —CO-(4-methoxyphenyl) |
| DETD-33 | | R1 = —CO-(4-methylphenyl) |
| DETD-34 | | R1 = —CO-(4-bromophenyl) |
| DETD-35 | | R1 = —CO—CH$_2$-(naphthalene-1-yl) |
| DETD-36 | | R1 = —CO-cyclopropyl |

TABLE 6-continued

Formula (I)

| Compound Number | Compound Structure | Substituents of Formula (I) |
| --- | --- | --- |
| DETD-37 | | R1 = —CO-cyclopentyl |
| DETD-38 | | R1 = —CO-cyclohexyl |
| DETD-39 | | R1 = —CO—(E)CH=CH(3-methoxyphenyl) |
| DETD-40 | | R1 = —CO-benzofuran-2-yl |
| DETD-41 | | R1 = —CO-benzothiofuran-2-yl |
| DETD-42 | | R1 = —CO-(E)CH=CH-(thiofuran-2-yl) |
| DETD-43 | | |
| DETD-44 | | |
| DETD-45 | | |

TABLE 6-continued

Formula (I)

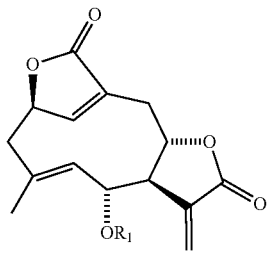

| Compound Number | Compound Structure | Substituents of Formula (I) |
| --- | --- | --- |
| R1 = —CO—CH₂-phenyl | R1 = —CO—CH₂-(4-methoxyphenyl) | R1 = —CO—CH₂-(6-methoxynaphthalene-1-yl) |
| DETD-46 | DETD-47 | DETD-48 |
| R1 = —CO—CH₂-(6-methoxynaphthalene-2-yl) | R1 = —CO-(E)CH=CH-(3-trifluromethoxyphenyl) | R1 = —CO-(E)CH=CH-(3-trifluromethylphenyl) |
| DETD-49 | DETD-50 | DETD-51 |
| R1 = —CO—(E)CH=CH-(3,4-dimethoxyphenyl) | R1 = —CO—(E)CH=CH-(3-ethoxyphenyl) | R1 = —CO—(CH₂)₂-naphthalene-1-yl |

TABLE 6-continued
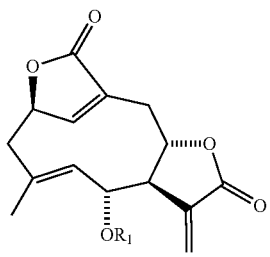
Formula (I)
| Compound Number | Compound Structure | Substituents of Formula (I) |
|---|---|---|
DETD-52
R1 = —CO—(CH₂)₂-(quinolin-8-yl)
DETD-53
R1 = —CO—CH(S—CH₃)(6-methoxynaphthalene-2-yl) (S)
DETD-54
R1 = —CO—CH(R—CH₃)(6-methoxynaphthalene-2-yl) (R)
DETD-55
R1 = —CO—C(CH₃)(OCH₃)-(naphthalene-2-yl)
DETD-56
R1 = —CO—CH(S—OCH₃)-(naphthalene-2-yl) (S)
DETD-57
R1 = —CO—CH(R—OCH₃)-(naphthalene-2-yl) (R)

TABLE 6-continued
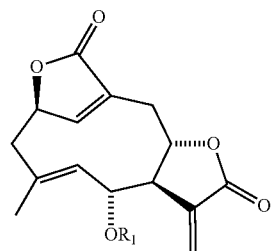
Formula (I)
| Compound Number | Compound Structure | Substituents of Formula (I) |
|---|---|---|
DETD-58
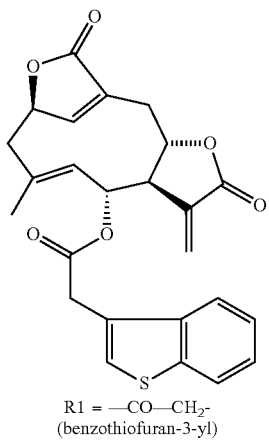
R1 = —CO—CH₂-
(benzothiofuran-3-yl)
DETD-59
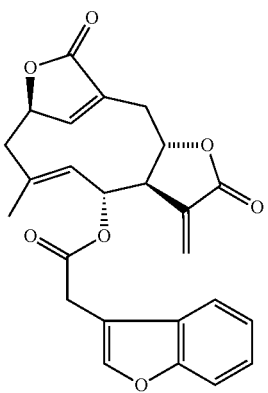
R1 = —CO—CH₂-
(benzofuran-3-yl)
DETD-60
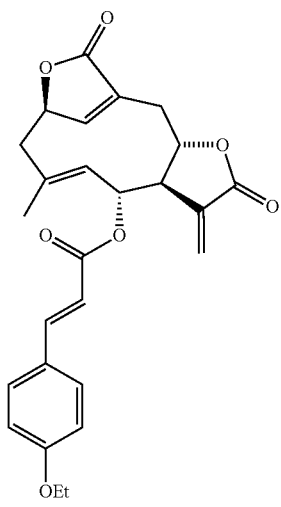
R1 = —CO—(E)CH=CH-(4-
ethoxyphenyl
DETD-61
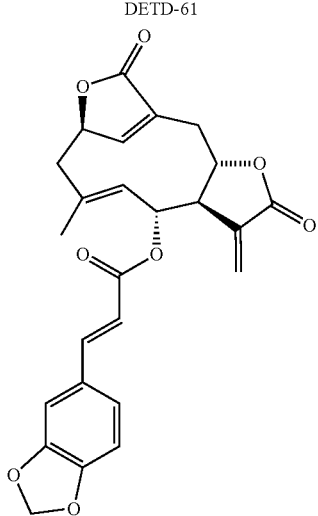
R1 = —CO—(E)(CH=CH-(1,3-
benzodioxane-5-yl)
DETD-62
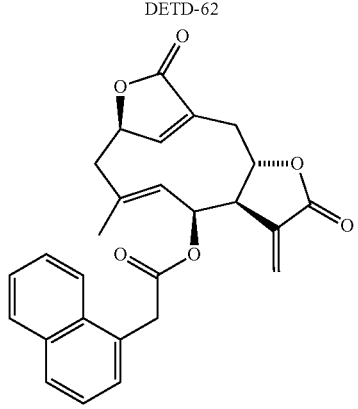
R1 = —CO—CH₂-
(naphthalene-1-yl)

What is claimed is:

1. A compound of Formula (I)

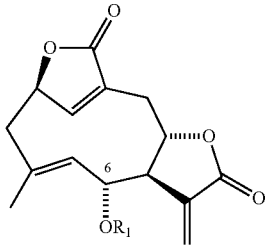

or a pharmaceutically acceptable salt thereof,
wherein $R_1$ is selected from the group consisting of hydrogen, -carbonyl($C_1$-$C_8$)alkyl($C_1$-$C_8$)alkenyl, -carbonyl($C_1$-$C_8$)alkyl($C_1$-$C_8$)alkenyl($C_1$-$C_8$)alkyl, -carbonyl($C_1$-$C_8$)alkenyl($C_6$-$C_{20}$)aryl, -carbonyl($C_1$-$C_8$)alkenyl($C_1$-$C_8$)alkoxy($C_6$-$C_{20}$)aryl, -carbonyl($C_1$-$C_8$)alkenyl, -carbonyl($C_1$-$C_8$)haloalkyl, -carbonyl($C_1$-$C_8$)alkyl, -carbonyl($C_1$-$C_8$)alkylOCO($C_1$-$C_8$)alkyl, -carbonyl($C_1$-$C_8$)alkenyl($C_1$-$C_8$)alkyl($C_1$-$C_8$)alkenyl, -carbonyl($C_1$-$C_8$)alkanol($C_1$-$C_8$)alkyl, -carbonyl($C_1$-$C_8$)alkenyl($C_1$-$C_8$)alkyl($C_6$-$C_{20}$)aryl, -carbonyl($C_1$-$C_8$)alkenyl($C_6$-$C_{20}$)haloaryl, -carbonyl($C_1$-$C_8$)alkenyl($C_3$-$C_8$)heteroaryl, -carbonyl($C_6$-$C_{20}$)aryl, -carbonyl($C_1$-$C_8$)alkoxy($C_6$-$C_{20}$)aryl, -carbonyl($C_1$-$C_8$)alkyl($C_6$-$C_{20}$)aryl, -carbonylhalo($C_6$-$C_{20}$)aryl, -carbonyl($C_3$-$C_8$)cycloalkyl, -carbonyl($C_1$-$C_8$)alkenyl($C_1$-$C_8$)haloalkyl ($C_6$-$C_{20}$)aryl, —CO-(E)C($CH_3$)=CHCH$_2$CH$_3$, —CO-(E)CH=CHCH$_2$CH$_3$, —CO—C(CH$_2$CH$_3$)=CH$_2$, —CO-(E)CH=C(CH$_3$)CH(CH$_3$)$_2$, —CO-2-thiofuranyl, —CO-benzofuran-2-yl, —CO-benzothiofuran-2-yl, —CO-(4-methylphenyl), —CO—CH$_2$-(4-methoxyphenyl), —CO—CH$_2$-(6-methoxynaphthalene-1-yl), —CO—CH$_2$-(6-methoxynaphthalene-2-yl), —CO—CH$_2$-(quinolin-8-yl), —CO—CH$_2$-(benzothiofuran-3-yl), —CO—CH$_2$-(benzofuran-3-yl), —CO—CH$_2$-(napthalene-1-yl), —CO—CH(S—CH$_3$)(6-methoxylnaphthalene-2-yl), and -carbonyl($C_1$-$C_8$)alkyl($C_1$-$C_8$)alkoxy($C_6$-$C_{20}$)aryl.

2. The compound of claim 1, wherein $R_1$ is hydrogen, —CO—C(CH$_3$)=CH$_2$, —CO-(E)C(CH$_3$)=CHCH$_2$CH$_3$, —CO-(E)CH=CH-phenyl, —CO-(E)CH=CH-(3,4,5-trimethoxy)phenyl, —CO—CH=C(CH$_3$)$_2$, —CO—CH(Cl)$_2$, —CO—CH$_2$—CH(CH$_3$)$_2$, —CO—CH$_2$C(CH$_3$)(CH$_2$CH$_3$)(OCOCH$_3$), —CO-(E)CH=C(CH$_3$)CH(CH$_3$)$_2$, —CO—CH(CH$_3$)CH$_2$CH$_3$, —CO-(E)CH=C(CH$_3$)CH$_2$CH$_2$CH=C(CH$_3$)$_2$, —CO—CH(CH$_2$CH$_3$)$_2$, —CO—CH$_3$, —CO—CH$_2$C(CH$_3$)CH$_2$CH$_3$, —CO—C(CH$_2$CH$_3$)=CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$), —CO-(E)CH=CHCH$_3$, —CO-(E)CH=CHCH$_2$CH$_3$, —CO-(E)CH=CH-(4-methoxyphenyl), —CO-(E)CH=CH-(4-methylphenyl), —CO-(E)CH=CH-(4-chlorophenyl), —CO-(E)CH=CH(furan-2-yl), —CO-2-thiofuranyl, —CO-phenyl, —CO-(4-methoxyphenyl), —CO-(4-methylphenyl), —CO-(4-bromophenyl), —CO—CH$_2$-naphthalene-1-yl, —CO-cyclopropyl, —CO-cyclopentyl, —CO-cyclohexyl, —CO-(E)CH=CH(3-methoxyphenyl), —CO-benzofuran-2-yl, —CO-benzothiofuran-2-yl, —CO-(E)CH=CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)CH=CH-(3-trifluromethoxyphenyl), —CO-(E)CH=CH-(3-trifluromethylphenyl), —CO-(E)CH=CH-(3,4-dimethoxyphenyl), —CO-(E)CH=CH-(3-ethoxyphenyl), —CO—(CH$_2$)$_2$-(naphthalene-1-yl), —CO—CH$_2$-(quinolin-8-yl), —CO—CH(S—CH$_3$)(6-methoxylnaphthalene-2-yl), —CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH=CH-(4-ethoxyphenyl), —CO-(E)CH=CH-(1,3-benzodioxane-5-yl), and —CO—CH$_2$-(napthalene-1-yl).

3. The compound of claim 1, which is selected from the group consisting of

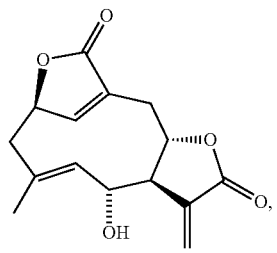

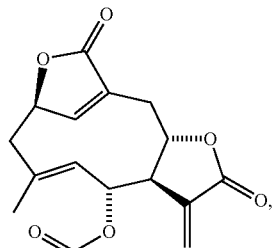

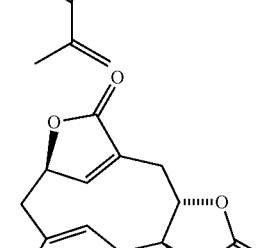

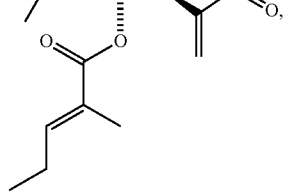

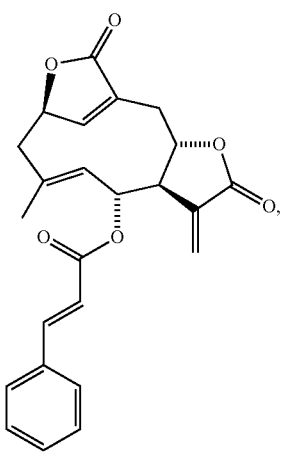
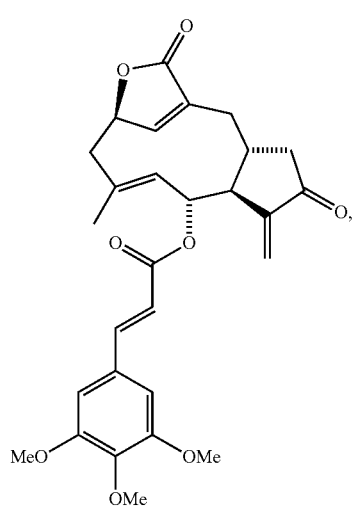
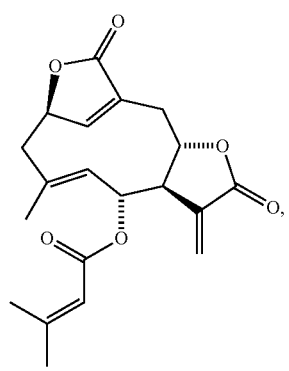
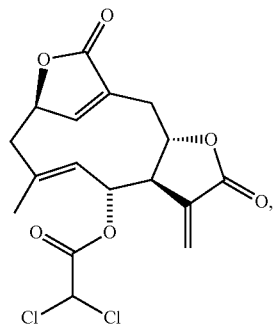
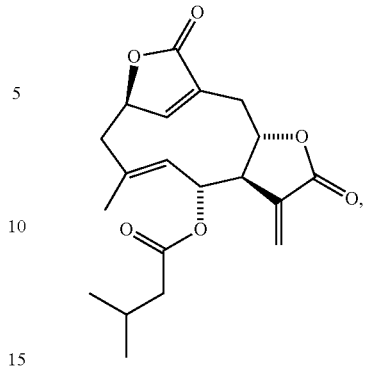
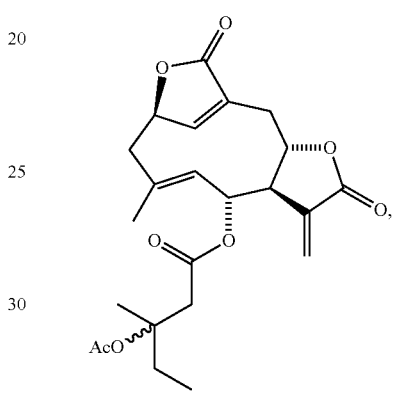
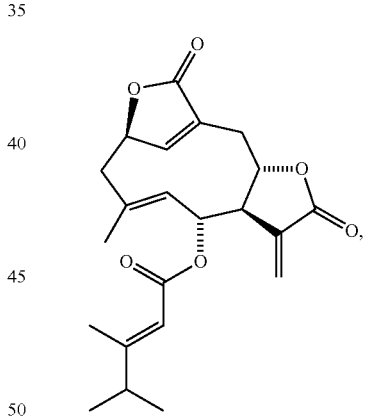
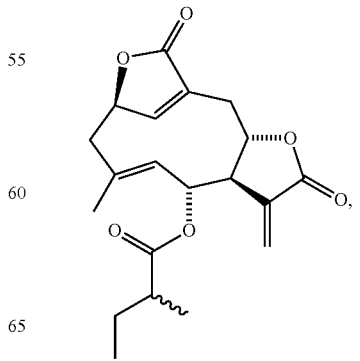

61
-continued
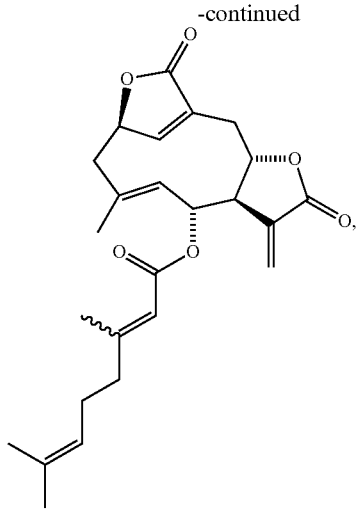
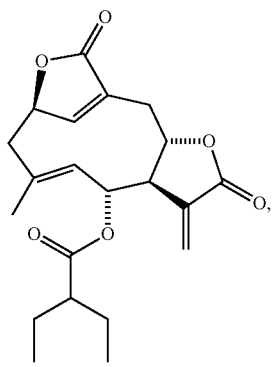
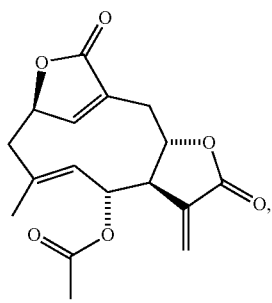
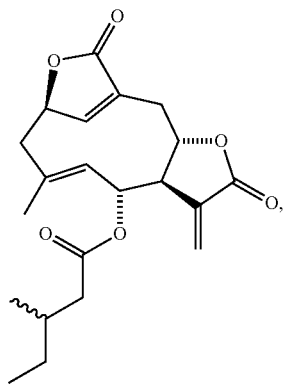
62
-continued
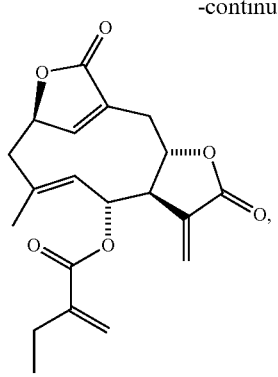
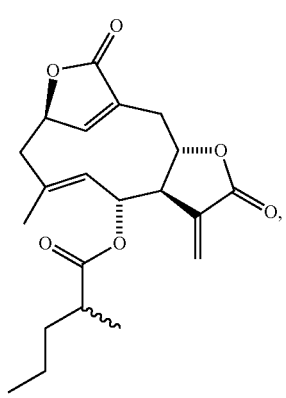
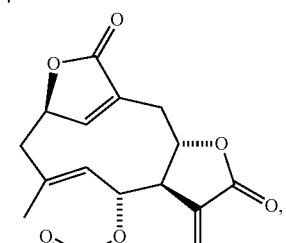

63
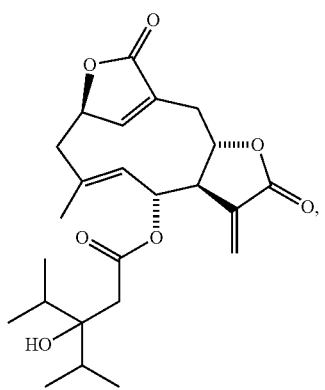
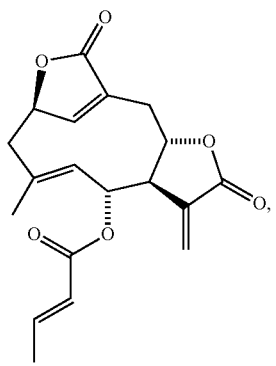
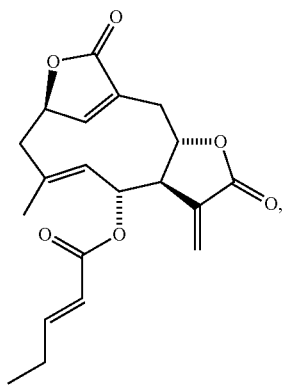
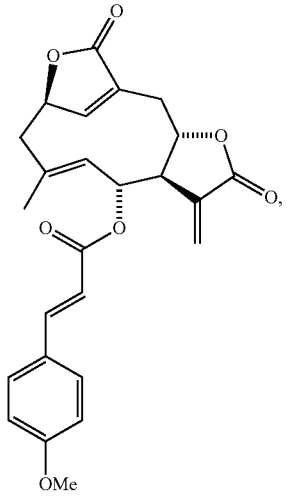
64
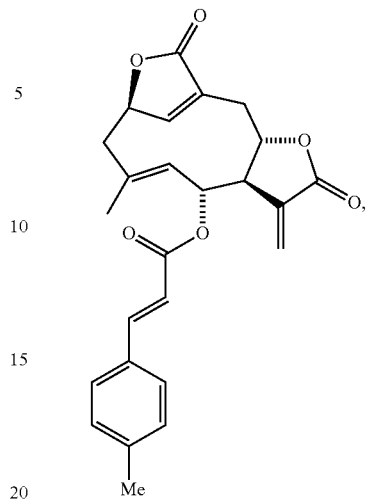
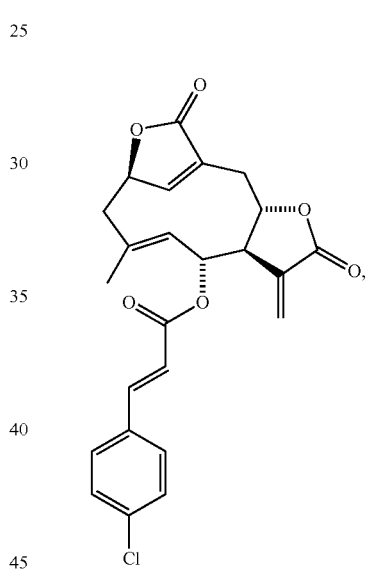
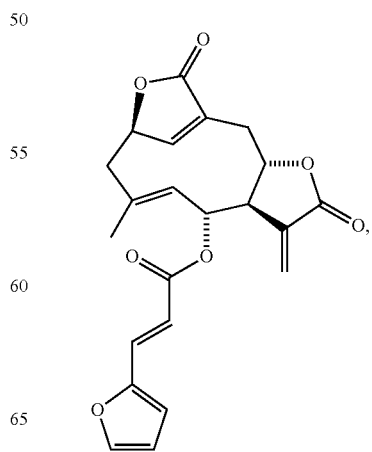

65
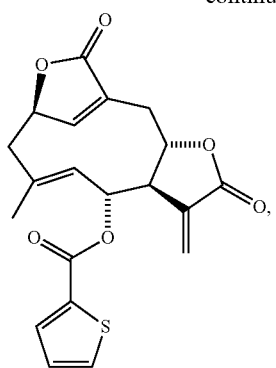
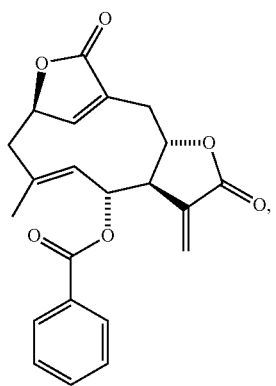
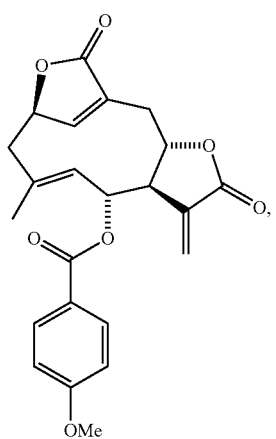
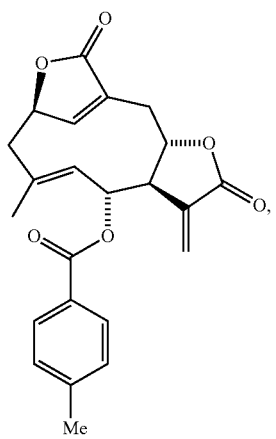
66
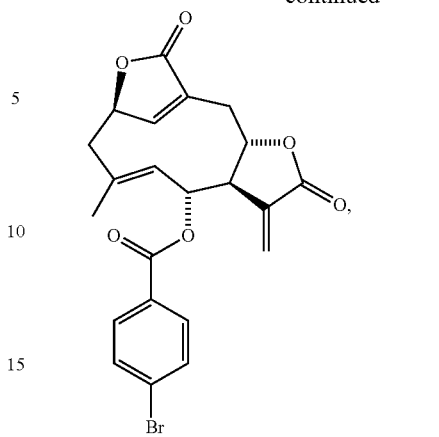
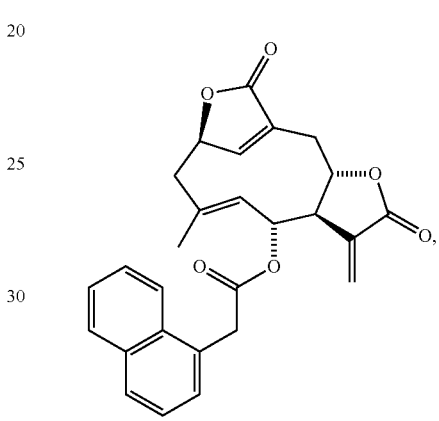
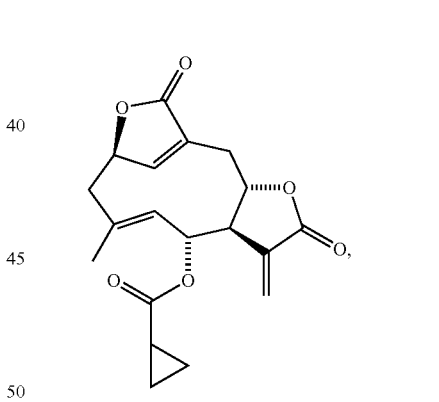
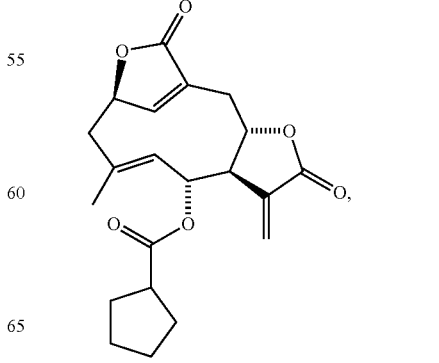

67
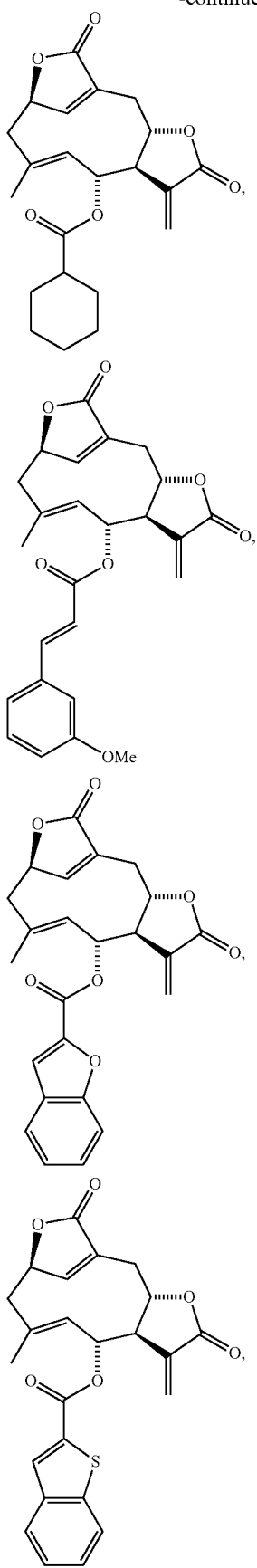
68
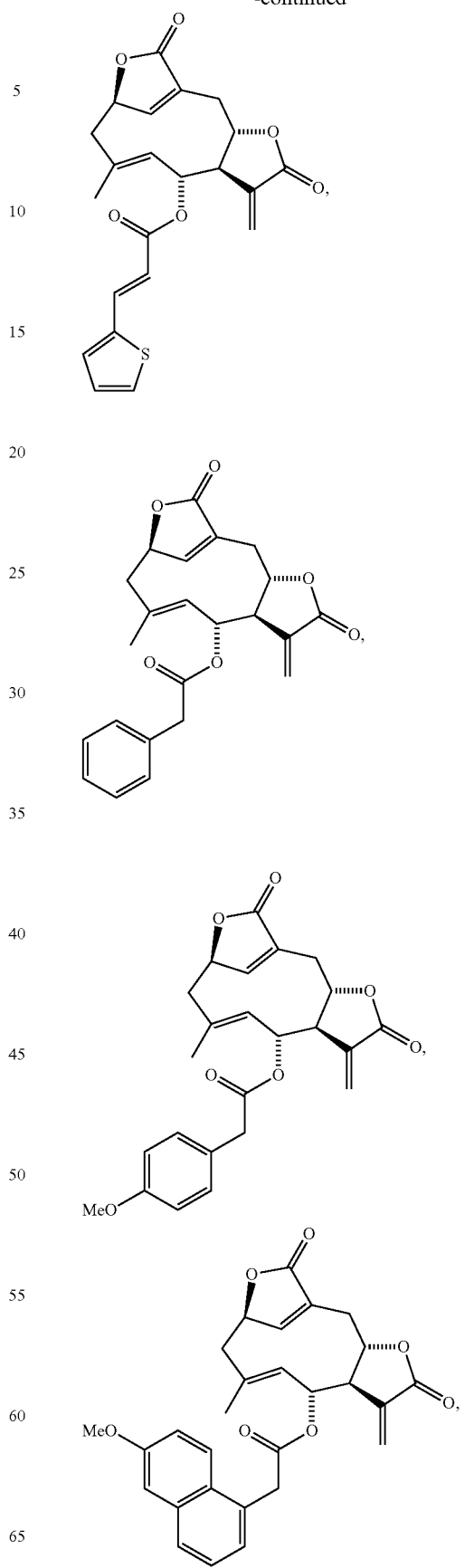

69
-continued
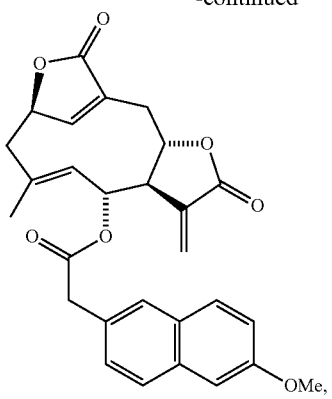
70
-continued
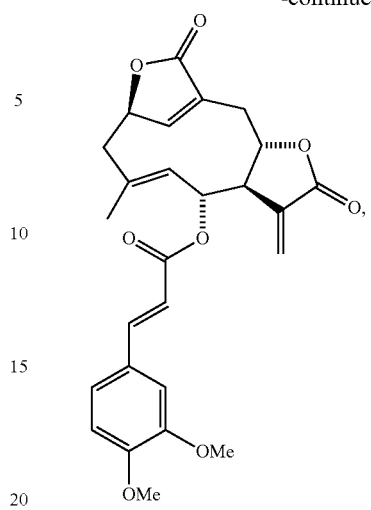
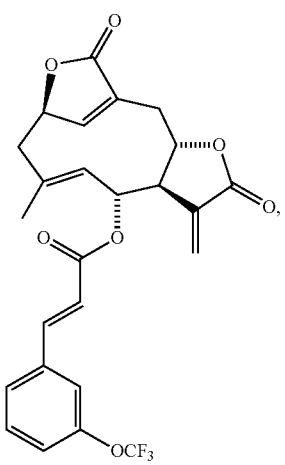
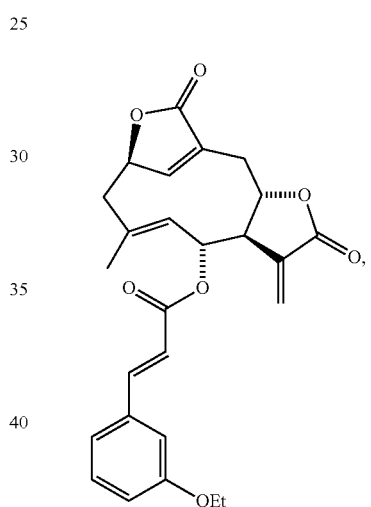
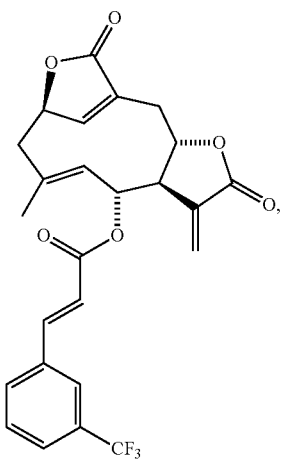
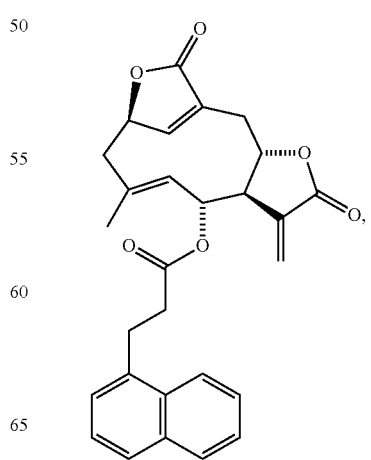

71
-continued
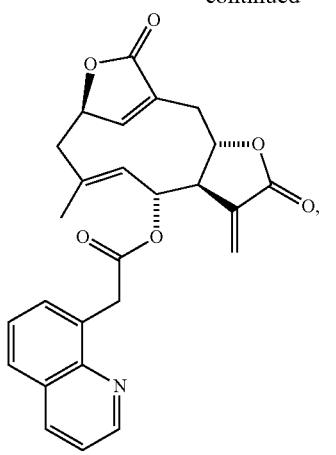
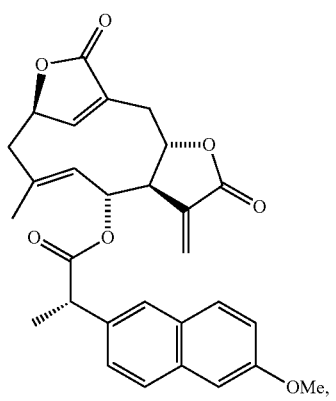
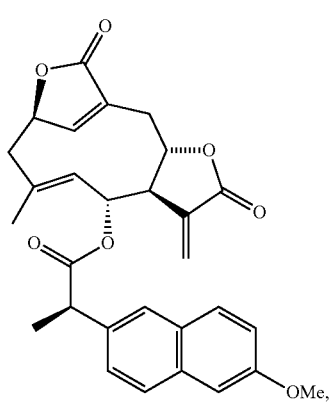
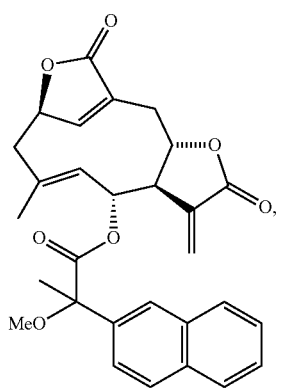
72
-continued
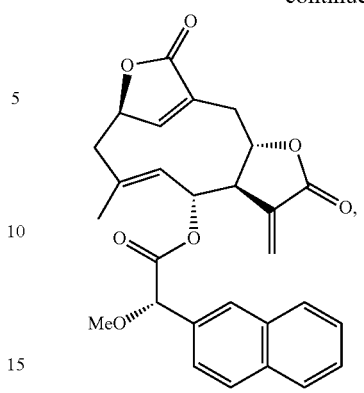
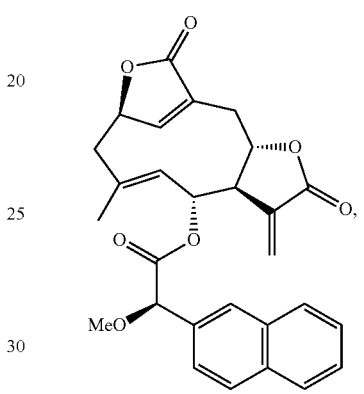
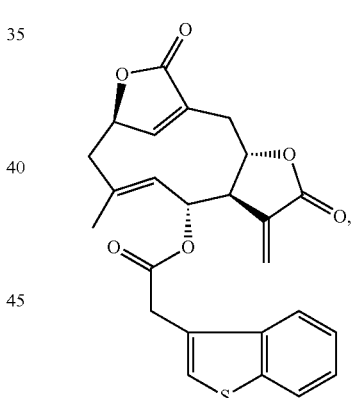
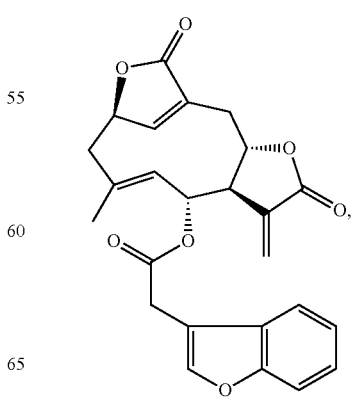

-continued

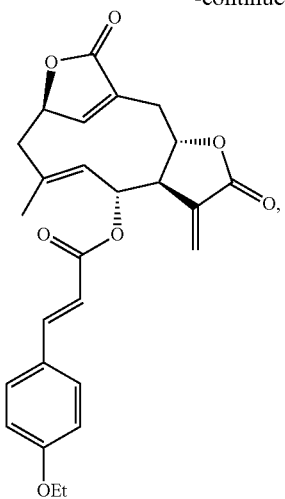

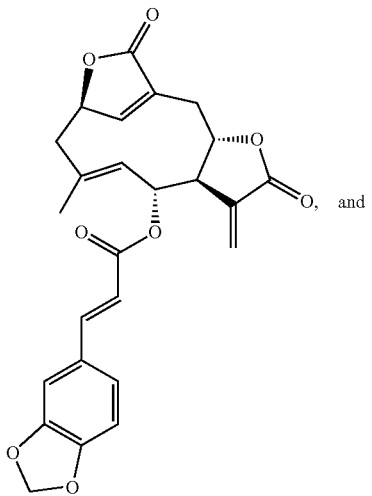, and

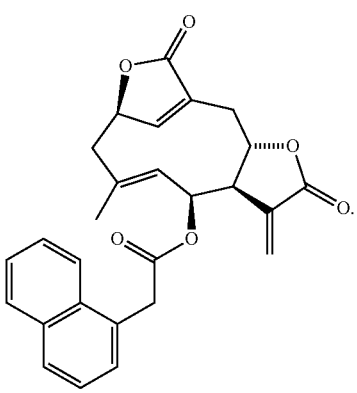

4. A method of preparing the compound of Formula (I)

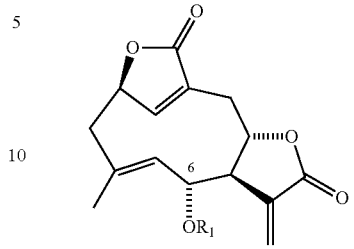

Formula (I)

or a pharmaceutically acceptable salt thereof,
wherein $R_1$ is selected from the group consisting of hydrogen, —CO—C(CH$_3$)=CH$_2$, —CO-(E)C(CH$_3$)=CHCH$_2$CH$_3$, —CO-(E)CH=CH-phenyl, —CO-(E)CH=CH-(3,4,5-trimethoxy)phenyl, —CO—CH=C(CH$_3$)$_2$, —CO—CH(Cl)$_2$, —CO—CH$_2$—CH(CH$_3$)$_2$, —CO—CH$_2$C(CH$_3$)(CH$_2$CH$_3$)(OCOCH$_3$), —CO-(E)CH=C(CH$_3$)CH(CH$_3$)$_2$, —CO—CH(CH$_3$)CH$_2$CH$_3$, —CO-(E)CH=C(CH$_3$)CH$_2$CH$_2$CH=C(CH$_3$)$_2$, —CO—CH(CH$_2$CH$_3$)$_2$, —CO—CH$_3$, —CO—CH$_2$C(CH$_3$)CH$_2$CH$_3$)=CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$), —CO-(E)CH=CHCH$_3$, —CO-(E)CH=CHCH$_2$CH$_3$, —CO-(E)CH=CH-(4-methoxyphenyl), —CO-(E)CH=CH-(4-methylphenyl), —CO-(E)CH=CH-(4-chlorophenyl), —CO-(E)CH=CH(furan-2-yl), —CO-2-thiofuranyl, —CO-phenyl, —CO-(4-methoxyphenyl), —CO-(4-methylphenyl), —CO-(4-bromophenyl), —CO—CH$_2$-naphthalene-1-yl, —CO-cyclopropyl, —CO-cyclopentyl, —CO-cyclohexyl, —CO-(E)CH=CH(3-methoxyphenyl), —CO-benzofuran-2-yl, —CO-benzothiofuran-2-yl, —CO-(E)CH=CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)CH=CH-(3-trifluromethoxyphenyl), —CO-(E)CH=CH-(3-trifluromethylphenyl), —CO-(E)CH=CH-(3,4-dimethoxyphenyl), —CO-(E)CH=CH-(3-ethoxyphenyl), —CO—(CH$_2$)$_2$-(naphthalene-1-yl), —CO—CH$_2$-(quinolin-8-yl), —CO—CH(S—CH$_3$)(6-methoxylnaphthalene-2-yl), —CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH=CH-(4-ethoxyphenyl), —CO-(E)CH=CH-(1,3-benzodioxane-5-yl), and —CO—CH$_2$-(napthalene-1-yl), the method comprising the steps of:

(5) reacting the compound of Formula (II)

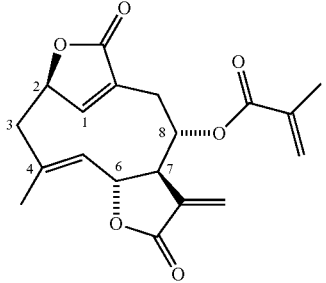

Formula (II)

with aqueous sodium hydroxide to obtain the compound of Formula (I),

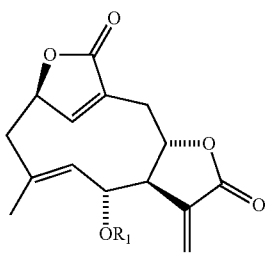

Formula (I)

wherein $R_1$ is hydrogen; and (6) reacting the compound of Formula (I), wherein $R_1$ is hydrogen, with 1-naphthylacetic acid, diethyl azodicarboxylate (DEAD) and triphenylphosphine (PPh3) to afford the compound of Formula (I), wherein $R_1$ is —CO—CH$_2$-(napthalene-1-yl); or (7) reacting the compound of Formula (I), wherein R, is hydrogen, with 1-(3-dimethylaminopropyl)-3-ethylcarbodiimide hydrochloride (EDC) dimethylaminopyridine (DMAP), and a compound of Formula (III)

$R_2COOH$  Formula (III), wherein $R_2$ is selected from the group consisting of —CO—C(CH$_3$)═CH$_2$, —CO-(E)C(CH$_3$)═CHCH$_2$CH$_3$, —CO-(E)CH═CH-phenyl, —CO-(E)CH═CH-(3,4,5-trimethoxy)phenyl, —CO—CH═C(CH$_3$)$_2$, —CO—CH(Cl$_2$), —CO—CH$_2$—CH(CH$_3$)$_2$, —CO—CH$_2$C(CH$_3$)(CH$_2$CH$_3$)(OCOCH$_3$), —CO-(E)CH═C(CH$_3$)CH(CH$_3$)$_2$, —CO—C(CH$_3$)CH$_2$CH$_3$, —CO-(E)CH═C(CH$_3$)CH$_2$CH$_2$CH═C(CH$_3$)$_2$, —CO—CH(CH$_2$CH$_3$)$_2$, —CO—CH$_3$, —CO—CH$_2$C(CH$_3$)CH$_2$CH$_3$, —CO—C(CH$_2$CH$_3$)═CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$, —CO-(E)CH═CHCH$_3$, —CO-(E)CH═CHCH$_2$CH$_3$, —CO-(E)CH═CH-(4-methoxyphenyl), —CO-(E)CH═CH-(4-methylphenyl), —CO-(E)CH═CH(4-chlorophenyl), —CO-(E)CH═CH(furan-2-yl), —CO-2-thiofuranyl, —CO-phenyl, —CO—CH$_2$-naphthalene-1-yl, —CO-(E)CH═CH(3-methoxyphenyl), —CO-benzofuran-2-yl, —CO-benzothiofuran-2-yl, —CO-(E)CH═CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)CH═CH-(3-trifluromethoxyphenyl), —CO-(E)CH═CH-(3-trifluromethylphenyl), —CO-(E)CH═CH-(3,4-dimethoxyphenyl), —CO-(E)CH═CH-(3-ethoxyphenyl), —CO—(CH$_2$)$_2$-(naphthalene-1-yl), —CO—CH$_2$-(quinolin-8-yl), —CO—CH(S—CH$_3$)(6-methoxylnaphthalene-2-yl), —(CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH═CH-(4-ethoxyphenyl), or —CO-(E)CH═CH-(1,3-benzodioxane-5-yl), and —CO—CH$_2$-(napthalene-1-yl), to obtain the compound of Formula (I), wherein $R_1$ is selected from the group consisting of —CO—C(CH$_3$)═CH$_2$, —CO-(E)C(CH$_3$)═CHCH$_2$CH$_3$, —CO-(E)CH═CH-phenyl, —CO-(E)CH═CH-(3,4,5-trimethoxy)phenyl, —CO—CH═C(CH$_3$)$_2$, —CO—CH(Cl$_2$), —CO—CH$_2$—CH(CH$_3$)$_2$, —CO—CH$_2$C(CH$_3$)(CH$_2$CH$_3$)(OCOCH$_3$), —CO-(E)CH═C(CH$_3$)CH(CH$_3$)$_2$, —CO—CH(CH$_3$)CH$_2$CH$_3$, —CO-(E)CH═C(CH$_3$)CH$_2$CH$_2$CH═C(CH$_3$)$_2$, —CO—CH—(CH$_2$CH$_3$)$_2$, —CO—CH$_3$, —CO—CH$_2$C(CH$_3$)CH$_2$CH$_3$, —CO—C(CH$_2$CH$_3$)═CH$_2$, —CO—C(CH$_3$)(CH$_2$)$_2$CH$_3$, —CO—C(CH$_2$CH$_3$)(CH$_2$)$_3$CH$_3$, —CO—CH(CH$_3$)(CH$_2$)$_3$CH$_3$, —CO—CH$_2$C(OH)((CH(CH$_3$)$_2$)$_2$, —CO-(E)CH═CHCH$_3$, —CO-(E)CH═CHCH$_2$CH$_3$, —CO-(E)CH═CH-(4-methoxyphenyl), —CO-(E)CH═CH-(4-methylphenyl), —CO-(E)CH═CH-(4-chlorophenyl), —CO-(E)CH═CH(furan-2-yl), —CO-2-thiofuranyl, —CO-phenyl, —CO—CH$_2$-naphthalene-1-yl, —CO-(E)CH═CH(3-methoxyphenyl), —CO-benzofuran-2-yl, —CO-benzothiofuran-2-yl, —CO-(E)CH═CH-(thiofuran-2-yl), —CO—CH$_2$-phenyl, —CO—CH$_2$-(4-methoxyphenyl), —CO—CH$_2$-(6-methoxynaphthalene-1-yl), —CO—CH$_2$-(6-methoxynaphthalene-2-yl), —CO-(E)CH═CH-(3-trifluromethoxyphenyl), —CO-(E)CH═CH-(3-trifluromethylphenyl), —CO-(E)CH═CH-(3,4-dimethoxyphenyl), —CO-(E)CH═CH-(3-ethoxyphenyl), —CO—(CH$_2$)$_2$-(naphthalene-1-yl), —CO—CH$_2$-(quinolin-8-yl), —CO—CH(S—CH$_3$)(6-methoxylnaphthalene-2-yl), —CO—CH(R—CH$_3$)(6-methoxylnaphthalene-2-yl), —CO—C(CH$_3$)(OCH$_3$)-(naphthalene-2-yl), —CO—CH(S—OCH$_3$)-(naphthalene-2-yl), —CO—CH(R—OCH$_3$)-(naphthalene-2-yl), —CO—CH$_2$-(benzothiofuran-3-yl), —CO—CH$_2$-(benzofuran-3-yl), —CO-(E)CH═CH-(4-ethoxyphenyl), —CO-(E)CH═CH-(1,3-benzodioxane-5-yl), and —CO—CH$_2$-(napthalene-1-yl); or (8) reacting the compound of Formula (I), wherein $R_1$ is hydrogen, with triethylamine and a compound of Formula (IV)

$R_3COCl$  Formula (IV), wherein $R_3$ is -(4-methoxyphenyl), -(4-methylphenyl), -(4-bromophenyl), -cyclopropyl, -cyclopentyl, or cyclohexyl to obtain the compound of Formula (I), wherein $R_1$ is —CO-(4-methoxyphenyl), —CO-(4-methylphenyl), —CO-(4-bromophenyl), —CO-cyclopropyl, —CO-cyclopentyl, or —CO-cyclohexyl.

5. A composition comprising the compound of claim 1 or a pharmaceutically acceptable salt thereof; and a pharmaceutically acceptable diluent or carrier.

6. A method for inhibition of proliferation, migration, mobility, invasion, growth, and/or metastasis of cancer cells in a patient, comprising:
   administering to the patient a therapeutically effective amount of the compound or the pharmaceutically acceptable salt thereof of claim 1.

7. The method of claim 6, wherein the cancer is selected from the group consisting of breast cancer, melanoma, drug-resistant melanoma, brain tumor, lung cancer, lymphoma, neuroepithelioma, kidney cancer, prostate cancer, stomach cancer, colon cancer, and uterus cancer.

8. A method for enhancement of an anti-proliferative effect of another anti-cancer drug on cancer cells when treating a patient, comprising:
   administering to the patient a therapeutically effective amount of the compound or the pharmaceutically acceptable salt thereof of claim 1.

9. The method of claim 8, wherein the another anti-cancer drug is selected from the group consisting of PLX4032, buthionine sulfoximine, sulfasalazine paclitaxel, docetaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-PD-1 drug, ipilimumab, doxorubicin, MEK inhibitor, capecitabine, PARP inhibitor, and tamoxifen.

10. The method of claim 8, wherein the compound or the pharmaceutically acceptable salt thereof exhibits synergism with the another anti-cancer drug.

11. A method for sensitizing and/or enhancing an anti-cancer effect of a gluthathione synthesis blocker on inhibition of triple negative breast cancer cell activity in a patient, comprising:
    administering to the patient a therapeutically effective amount of the compound or the pharmaceutically acceptable salt thereof of claim 1.

12. The method of claim 11, wherein the gluthathione synthesis blocker is a gamma-glutamylcysteine synthetase inhibitor or a cystine/glutamate transporter inhibitor.

13. A method for treatment and/or prophylaxis of lipopolysaccharide-stimulated inflammatory response in a patient, comprising:
    administering to the patient a therapeutically effective amount of the compound or the pharmaceutically acceptable salt thereof of claim 1.

14. The method of claim 13, wherein the lipopolysaccharide-stimulated inflammatory response is associated with an inflammatory disease selected from the group consisting of inflammatory dermatoses, inflammatory bowel disease, hypersensitivity lung disease, asthma, allergic rhinitis, autoimmune diseases, acute and chronic inflammatory diseases, Sjogren's syndrome, human immunodeficiency virus infection, and cancer.

15. A method of combination therapy for inhibition of proliferation, migration, invasion, and/or metastasis of cancer cells in a patient in need thereof, comprising:
    administering to the patient in need thereof a therapeutically effective amount of the compound or the pharmaceutically acceptable salt thereof of claim 1 and a therapeutically effective amount of one other anti-cancer agent selected from the group consisting of PLX4032, buthionine sulfoximine, sulfasalazine paclitaxel, docetaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-PD-1 drug, ipilimumab, doxorubicin, MEK inhibitor, capecitabine, PARP inhibitor, and tamoxifen.

16. A method for inhibition of proliferation, migration, mobility, invasion, growth, and/or metastasis of cancer cells in a patient, comprising:
    administering to the patient a therapeutically effective amount of the compound or pharmaceutically acceptable salt thereof of claim 2.

17. A method for enhancement of an anti-proliferative effect of another anti-cancer drug on cancer cells when treating a patient, comprising:
    administering to the patient a therapeutically effective amount of the compound or the pharmaceutically acceptable salt thereof of claim 2.

18. A method for sensitizing and/or enhancing an anti-cancer effect of a gluthathione synthesis blocker on inhibition of triple negative breast cancer cell activity in a patient, comprising:
    administering to the patient a therapeutically effective amount of the compound or the pharmaceutically acceptable salt thereof of claim 2.

19. A method for treatment and/or prophylaxis of lipopolysaccharide-stimulated inflammatory response in a patient, comprising:
    administering to the patient a therapeutically effective amount of the compound or the pharmaceutically acceptable salt thereof of claim 2.

20. A method of combination therapy for inhibition of proliferation, migration, invasion, and/or metastasis of cancer cells in a patient in need thereof, comprising:
    administering to the patient in need thereof a therapeutically effective amount of the compound or the pharmaceutically acceptable salt thereof of claim 2 and a therapeutically effective amount of one other anti-cancer agent selected from the group consisting of PLX4032, buthionine sulfoximine, sulfasalazine paclitaxel, docetaxel, cisplatin, oxaliplatin, betulinic acid, 4-S-cysteaminyl catechol, 4-S-cysteaminyl phenol, everolimus, bortezomib, carboplatin, dacarbazine, celecoxib, temozolomide, sorafenib, thalidomide, lenalidomide, valproic acid, vinblastine, imatinib mesylate, bosentan, apomine, arsenic trioxide, carmustine, lambrolizuma, anti-CTLA-4 drug, anti-PD-1 drug, ipilimumab, doxorubicin, MEK inhibitor, capecitabine, PARP inhibitor, and tamoxifen.

* * * * *